(12) United States Patent
Petolino et al.

(10) Patent No.: US 10,836,804 B2
(45) Date of Patent: Nov. 17, 2020

(54) PLANT TRANSACTIVATION INTERACTION MOTIFS AND USES THEREOF

(71) Applicant: DOW AGROSCIENCES, LLC, Indianapolis, IN (US)

(72) Inventors: Joseph Petolino, Zionsville, IN (US); Jianquan Li, Zionsville, IN (US); Steven L. Evans, Zionsville, IN (US); Ryan C. Blue, Fishers, IN (US)

(73) Assignee: Dow Agrosciences LLC, Indianapolis, IN (US)

( * ) Notice: Subject to any disclaimer, the term of this patent is extended or adjusted under 35 U.S.C. 154(b) by 14 days.

(21) Appl. No.: 16/401,246

(22) Filed: May 2, 2019

(65) Prior Publication Data

US 2019/0330292 A1    Oct. 31, 2019

Related U.S. Application Data

(63) Continuation of application No. 13/757,674, filed on Feb. 1, 2013, now Pat. No. 10,351,610.
(Continued)

(51) Int. Cl.
  *C07K 14/47* (2006.01)
  *C12N 15/82* (2006.01)
  (Continued)

(52) U.S. Cl.
  CPC ........ *C07K 14/4705* (2013.01); *C07K 14/415* (2013.01); *C12N 15/625* (2013.01);
  (Continued)

(58) Field of Classification Search
  None
  See application file for complete search history.

(56) References Cited

U.S. PATENT DOCUMENTS

| 5,623,054 A | 4/1997 | Zhang et al. |
| 5,880,333 A | 3/1999 | Goff |

(Continued)

FOREIGN PATENT DOCUMENTS

| DK | 2415872 T3 | 12/2006 |
| EP | 0693554 | 1/1996 |

(Continued)

OTHER PUBLICATIONS

Elliott et al. VP16 interacts via its activation domain with VP22, a tegument protein of Herpes Simplix Virus, and is relocated to a novel macromolecular assembly in coexpressing cells. Journal of Virology. 1995. 69(12): 7932-7941.*

(Continued)

*Primary Examiner* — Ashley K Buran

(57) ABSTRACT

This disclosure concerns compositions and methods for increasing the expression of a polynucleotide of interest. Some embodiments concern novel transactivation polypeptides and variants thereof that have been identified in plants, and methods of using the same. Particular embodiments concern the use of at least one DNA-binding polypeptide in a fusion protein to target at least one transactivation polypeptide or variant thereof to a specific binding site on a nucleic acid comprising the polynucleotide of interest, such that its expression may be increased.

23 Claims, 31 Drawing Sheets

Specification includes a Sequence Listing.

Related U.S. Application Data

(60) Provisional application No. 61/594,245, filed on Feb. 2, 2012.

(51) Int. Cl.
    *C12N 15/62*     (2006.01)
    *C07K 14/415*     (2006.01)

(52) U.S. Cl.
    CPC ..... *C12N 15/8216* (2013.01); *C12N 15/8217* (2013.01); *C07K 2319/71* (2013.01)

(56) References Cited

U.S. PATENT DOCUMENTS

| | | |
|---|---|---|
| 5,968,793 A | 10/1999 | Liu et al. |
| 6,087,166 A | 7/2000 | Baron et al. |
| 6,127,606 A | 10/2000 | Bennett et al. |
| 6,271,341 B1 | 8/2001 | Baron et al. |
| 6,432,927 B1 | 8/2002 | Gregory et al. |
| 6,706,866 B1 | 3/2004 | Thomashow et al. |
| 7,393,946 B1 | 7/2008 | Memelink et al. |
| 7,960,616 B2 | 6/2011 | Heinrichs et al. |
| 2003/0044957 A1 | 3/2003 | Jamieson |
| 2006/0063231 A1 | 3/2006 | Sangamo |
| 2008/0104726 A1 | 5/2008 | Ceres |
| 2011/0123509 A1* | 5/2011 | Jantz ............ C12N 9/22 424/94.3 |

FOREIGN PATENT DOCUMENTS

| | | |
|---|---|---|
| EP | 0823480 A1 | 8/1996 |
| EP | 0823480 | 2/1998 |
| EP | 1034267 A1 | 9/2000 |
| JP | 2000515728 | 11/2000 |
| JP | 2001503995 | 3/2001 |
| JP | 2002531096 A | 9/2002 |
| JP | 2010512745 | 4/2010 |
| NZ | 599351 A | 10/2009 |
| WO | WO1997017455 A2 | 5/1997 |
| WO | WO1998059026 | 6/1997 |
| WO | WO2008/076290 | 12/2006 |
| WO | WO2011049627 | 4/2011 |

OTHER PUBLICATIONS

Okanami Masahiro, et al. "Half-1, a bZIP-type protein, interacting with the wheat transcription factor HDP-1a contains a novel transcriptional activation domain." Genes to Cells 1.1 (1996): 87-99.

Shikata, M, et al. "Arabidopsis ZIM, a plant-specific GATA factor, can function as a transcriptional activator." Bioscience, biotechnology, and biochemistry 67.11 (2003): 2495-2497.

Uniprot Accession O80338 "Ethylene-responsive transcription factor 2" from URL: http://www.uniprot.org/uniprot/O80338.

Gu, YQet al. "Tomato transcription factors Pti4, Pti5, and Pti6 activate defense responses when expressed in *Arabidopsis*." The Plant Cell 14.4 (2002): 817-831.

Zhou, J. "The Pto kinase conferring resistance to tomato bacterial speck disease interacts with proteins that bind a cis-element of pathogenesis-related genes." The EMBO Journal 16.11 (1997): 3207-3218.

Takagi, M et al. "Ethylene-inducible DNA binding proteins that interact with an ethylene-responsive element." The Plant Cell 7.2 (1995): 173-182.

Liu, Q, et al. "Two transcription factors, DREB1 and DREB2, with an EREBP/AP2 DNA binding domain separate two cellular signal transduction pathways in drought-and low-temperature-responsive gene expression, respectively, in *Arabidopsis*." The Plant Cell 10.8 (1998): 1391-1406.

Sakuma Y et al. DNA-binding specificity of the ERF/AP2 domain of *Arabidopsis* DREBs, transcription factors involved in dehydration- and cold-inducible gene expression. Biochem Biophys Res Commun. 2002;290(3):998-1009.

Stockinger, E., et al. "*Arabidopsis thaliana* CBF1 encodes an AP2 domain-containing transcriptional activator that binds to the C-repeat/DRE, a cis-acting DNA regulatory element that stimulates transcription in response to low temperature and water deficit." Proceedings of the National Academy of Sciences 943 (1997): 1035-1040.

Yanagisawa, S. "The transcriptional activation domain of the plant-specific Dof1 factor functions in plant, animal, and yeast cells." Plant and Cell Physiology 42.8 (2001): 813-822.

Yanagisawa and Izui, "Molecular cloning of two DNA-binding proteins of maize that are structurally different but interact with the same sequence motif," Journal of Biological Chemistry, vol. 268, No. 21, pp. 16028-16036, 1993.

Yokoi et al., Gene Transfer of an Engineered Zinc Finger Protein Enhances Defense System, Molecular Therapy, Nov. 2007, vol. 15 No. 11 pp. 1917-1923.

Okanami et al., Genes Cells, 1996, vol. 1, No. 1 pp. 87-99.

International Search Report and Written Opinion for PCT Application No. PCT/US2013/024452, dated May 29, 2013.

Walker et al., Molecular and Cellular Biology, Sep. 1993., pp. 5233-5244.

Chantal Langlois et al., Journal of the American Chemical Society. vol. 130, No. 32, (Aug. 1, 2008) pp. 10596-10604.

Fujimoto Sy et al., The Plant Cell., vol. 12 No. 3 (Mar. 1, 2000), pp. 393-404.

Fujita et al., The Plant Cell., vol. 17 No. 12 (Dec. 1, 2005), pp. 3470-3488.

Ohta et al., The Plant Journal., vol. 22 No. 1 (Apr. 1, 2000), pp. 29-38.

Yao et al. Gal4 DNA-binding domain/VP16 activation domain fusion protein. GenBank Accession No. AAN86074. published Dec. 19, 2002. pp. 1-2.

Ohta et al. Repression domains of class II ERF transcritional repressors share an essential motif for active repression. The Plant Cell. 2001. 13: 1959-1968.

He et al. BZR1 is a transcriptional repressor with dual roles in Brassinosteroid homeostasis and growth responses. Science. 2005. 307: 1634-1638.

GenBank Accession No. NM_124093.2. *Arabidopsis thaliana* ethylene-responsive transcription factor 2 mRNA. Published Jan. 22, 2014. pp. 1-2.

GenBank Accession No. BAA32419. Ethylene repsonsive element binding factor 2. Published Aug. 25, 2000. pp. 1.

GenBank Accession AAA45864. VP16. published Aug. 2, 1993. pp. 1-2.

Elliott et al. VP16 interacts via its activation domain with VP22, a tegument protein of herpes simplex virus, and is relocated to a novel macromolecular assembly in coexpressing cells. Journal of Virology. 1995. 69(12):7932-7941.

\* cited by examiner

FIG. 1

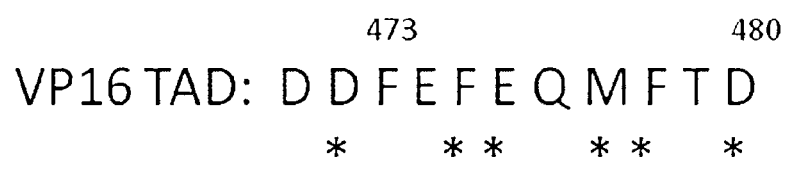

```
                      473                480
VP16 TAD:  D D F E F E Q M F T D
           *   * *   * *   *
```

FIG. 2

```
                                                        *     *  *  **   *
VP16    (SEQ ID NO:1)      GMTHD-PVSYG-A-LDV--D-D-FEF-EQMF-TDALGIDD
ERF2    (SEQ ID NO:2)      NDS-ED-MLVY-GL-L-K-DAFHFDTS-SS---D-LSCLF
PTI4    (SEQ ID NO:3)      CLT-ET-WGDL--P-L-KVDDSE-DMVIYGLLKDALSVGW
AtERF1  (SEQ ID NO:4)      CFT-ES-WGDL--P-L-K-EN-DSE-D---ML-V-YGILN
ORCA2   (SEQ ID NO:5)      -FN-ENC-EEIISPNYAS-EDLS-D--I--ILTDIFKDQD
DREB1A  (SEQ ID NO:6)      GFDMEETLVEAIYTAEQS-ENAFYMHDEAMFEMPSLLANM
CBF1    (SEQ ID NO:7)      ----EQS--EGAFYM----D--E----ETMFGMPTLLDNM
DOF1    (SEQ ID NO:8)      --SAG-K-A-V---LDD--ED-SFVWPAASF--DMGACWA

FGG-----
DFPA----
SPFSFTAG
DAFHGG--
NYEDE---
AEGM----
AEG-----
GAGFAD--
```

FIG. 3

```
ERF2
VP16 motif      (SEQ ID NO:9)
Native ERF2     (SEQ ID NO:10)
vERF2_1         (SEQ ID NO:17)
vERF2_2         (SEQ ID NO:18)
vERF2_3         (SEQ ID NO:19)
vERF2_4         (SEQ ID NO:20)
vERF2_5         (SEQ ID NO:21)
vERF2_6         (SEQ ID NO:22)
vERF2_7         (SEQ ID NO:121)
```

| | | | | | | | |
|---|---|---|---|---|---|---|---|
| D | D | FE | FE | Q | M | F | T | D |
| D | A | FH | FD | T | S | S | S | D |
| D | D | $FX_1$ | FD | $X_2$ | $X_3$ | F | $X_4$ | D |
| D | $X_5$ | $FX_6$ | $FX_7$ | $X_8$ | $X_9$ | F | $X_{10}$ | D |
| D | $X_{11}$ | $FX_{12}$ | $FX_{13}$ | $X_{14}$ | $X_{15}$ | $X_{16}$ | $X_{17}$ | D |
| D | $X_{18}$ | $FX_{19}$ | $FX_{20}$ | $X_{21}$ | $X_{22}$ | $X_{23}$ | $X_{24}$ | D |
| D | $X_{25}$ | $FX_{26}$ | $FX_{27}$ | $X_{28}$ | $X_{29}$ | $X_{30}$ | $X_{31}$ | D |
| D | D | FH | FE | T | M | F | S | D |
| D | $X_{32}$ | FH | $FX_{33}$ | T | $X_{34}$ | $X_{35}$ | S | D |

Where:
$X_1$ = E or H          $X_5$ = D or A          $X_{11}$ = D, or E
$X_2$ = Q or T          $X_6$ = E or H          $X_{12}$ = D, E, or H
$X_3$ = M or S          $X_7$ = D or E          $X_{13}$ = D or E
$X_4$ = T or S          $X_8$ = Q or T          $X_{14}$ = Q or T
                        $X_9$ = M or S          $X_{15}$ = A, V, I, L, or M
                        $X_{10}$ = T or S       $X_{16}$ = F, W, or Y
                                                $X_{17}$ = S, T, N, Q, C, G, or P $X_{18}$ = D or E
$X_{19}$ = H, R, K, D, or E
$X_{20}$ = D or E
$X_{21}$ = S, T, N, Q, C, G, Y, or P
$X_{22}$ = A, V, I, L, M, F, Y, or W
$X_{23}$ = A, V, I, L, M, F, Y, or W
$X_{24}$ = S, T, N, Q, C, G, P, or Y $X_{25}$ = A, D, or E
$X_{26}$ = any
$X_{27}$ = D or E
$X_{28}$ = any
$X_{29}$ = A, V, I, L, M, F, Y, W, or S
$X_{30}$ = A, V, I, L, M, F, Y, W, or S
$X_{31}$ = any $X_{32}$ = D or E
$X_{33}$ = D or E
$X_{34}$ = A, V, I, L, or M
$X_{35}$ = F, W, or Y

FIG. 4

```
PTI4
VP16 motif  (SEQ ID NO:9)      DDF  EF  E    Q   M  -  F  -  T  -  -  D
Native PTI4 (SEQ ID NO:11)     DDS  E-  D    M   V  I  Y  G  L  L  K  D
vPTI4_1    (SEQ ID NO:23)      DDX₁ E-  X₂   X₃  X₄ I  X₅ G  X₆ L  K  D
vPTI4_2    (SEQ ID NO:24)      DDX₇ E-  X₈   X₉  X₁₀X₁₁X₁₂X₁₃X₁₄X₁₅X₁₆D
vPTI4_3    (SEQ ID NO:25)      DDX₁₇EF X₁₈ X₁₉X₂₀-  X₂₁- X₂₂- -  D
vPTI4_4    (SEQ ID NO:26)      DDX₂₃EX₂₄X₂₅X₂₆X₂₇-  X₂₈- X₂₉- -  D
vPTI4_5    (SEQ ID NO:27)      DDX₃₀EX₃₁X₃₂X₃₃X₃₄-  X₃₅- X₃₆- -  D
vPTI4_6    (SEQ ID NO:28)      DDF  EF  E    M   M  -  F  -  T  -  -  D
vPTI4_7    (SEQ ID NO:122)     DDX₃₇EX₃₈X₃₉M     X₄₀- X₄₁- X₄₂- -  D
```

Where:

$X_1$ = F or S       $X_7$ = any                         $X_{17}$ = F or S
$X_2$ = D or E       $X_8$ = D or E                      $X_{18}$ = D or E
$X_3$ = Q or M       $X_9$ = any                         $X_{19}$ = Q or M
$X_4$ = M or V       $X_{10}$ = A, V, I, L, or M         $X_{20}$ = M or V
$X_5$ = F or Y       $X_{11}$ = any                      $X_{21}$ = F or Y
$X_6$ = T or L       $X_{12}$ = F, W, or Y               $X_{22}$ = T or L
                     $X_{13}$ = any
                     $X_{14}$ = any
                     $X_{15}$ = any
                     $X_{16}$ = any $X_{23}$ = any                          $X_{30}$ = any
$X_{24}$ = F, W, or Y                   $X_{31}$ = F, W, Y, A, V, I, L, or M
$X_{25}$ = D or E                       $X_{32}$ = D or E
$X_{26}$ = any                          $X_{33}$ = any
$X_{27}$ = A, V, I, L, or M             $X_{34}$ = A, V, I, L, M, F, W, or Y
$X_{28}$ = F, W, or Y                   $X_{35}$ = F, W, Y, A, V, I, L, or M
$X_{29}$ = any                          $X_{36}$ = any $X_{37}$ = F or S
$X_{38}$ = F, W, or Y
$X_{39}$ = E or D
$X_{40}$ = A, V, I, L, or M
$X_{41}$ = F, W, or Y
$X_{42}$ = T or L

FIG. 5

```
AtERF1
VP16 motif    (SEQ ID NO:9)      D  -  DF  EF  E    Q   MF  T   D
Native AtERF1 (SEQ ID NO:12)     E  N  DS  E-  D    -   ML  V   -
vAtERF1_1     (SEQ ID NO:29)     X1 N  DX2 E-  X3   -   MX4 X5  -
vAtERF1_2     (SEQ ID NO:30)     X6 X7 DX8 E-  X9   -   MX10 X11
vAtERF1_3     (SEQ ID NO:31)     X12-  DX13EF X14 Q    MX15 X16 D
vAtERF1_4     (SEQ ID NO:32)     X17-  DX18EX19X20X21 MX22 X23 X24
vAtERF1_5     (SEQ ID NO:33)     X25-  DX26EX27X28X29 MX30 X31 X32
vAtERF1_6     (SEQ ID NO:34)     E  N  DF  EF  E    -   MF  T   D
vAtERF1_7     (SEQ ID NO:123)    E  N  DX33EX34X35 -   M

FIG. 6

```
ORCA2
VP16 motif (SEQ ID NO:9)      D  DF  E   F   E   Q   M   F   TD
Native ORCA2 (SEQ ID NO:13)   E  DL  S   D   I   -   I   L   TD
vORCA2_1 (SEQ ID NO:35)       X₁ DX₂ X₃  X₄  X₅  -   X₆  X₇  TD
vORCA2_2 (SEQ ID NO:36)       X₈ DX₉ X₁₀ X₁₁ X₁₂ -   X₁₃ X₁₄ TD
vORCA2_3 (SEQ ID NO:37)       X₁₅DX₁₆X₁₇ X₁₈ X₁₉ Q   X₂₀ X₂₁ TD
vORCA2_4 (SEQ ID NO:38)       X₂₂DX₂₃X₂₄ X₂₅ X₂₆ X₂₇ X₂₈ X₂₉ TD
vORCA2_5 (SEQ ID NO:39)       X₃₀DX₃₁X₃₂ X₃₃ X₃₄ X₃₅ X₃₆ X₃₇ TD
vORCA2_6 (SEQ ID NO:40)       E  DF  -   D   L   E   M   L   TD
vORCA2_7 (SEQ ID NO:124)      E  DX₃₈-   X₃₉ X₄₀ X₄₁ X₄₂ X₄₃ TD
```

Where:

$X_1$ = D or E          $X_8$ = any
$X_2$ = F or L          $X_9$ = any
$X_3$ = E or S          $X_{10}$ = any
$X_4$ = F or D          $X_{11}$ = F, L, A, V, I, M, Y, or W
$X_5$ = E or I          $X_{12}$ = D or E
$X_6$ = M or I          $X_{13}$ = F, L, A, V, I, M, Y, or W
$X_7$ = F or L          $X_{14}$ = F, L, A, V, I, M, Y, or W $X_{15}$ = D or E       $X_{22}$ = H, R, K, D, or E
$X_{16}$ = F or L       $X_{23}$ = F, L, A, V, I, M, Y, or W
$X_{17}$ = E or S       $X_{24}$ = S, T, N, Q, C, G, P, R, H, K, D, or E
$X_{18}$ = F or D       $X_{25}$ = F, W, or Y
$X_{19}$ = E or I       $X_{26}$ = D or E
$X_{20}$ = M or I       $X_{27}$ = S, T, N, Q, C, G, P, R, H, K, D, or E
$X_{21}$ = F or L       $X_{28}$ = L, A, V, I, or M
                        $X_{29}$ = F, Y, or W $X_{30}$ = any
$X_{31}$ = any
$X_{32}$ = any
$X_{33}$ = F, L, A, V, I, M, Y, or W
$X_{34}$ = D or E
$X_{35}$ = any
$X_{36}$ = F, L, A, V, I, M, Y, or W
$X_{37}$ = F, L, A, V, I, M, Y, or W $X_{38}$ = F or L
$X_{39}$ = F, Y, W, or D
$X_{40}$ = D, E, I, or L
$X_{41}$ = Q or E
$X_{42}$ = A, V, I, L, or M
$X_{43}$ = F, Y, W, or L

FIG. 7

```
DREB1A
VP16 motif     (SEQ ID NO:9)      D  D  -  FE F  -  -  -  EQ MF-  T  D
Native DREB1A  (SEQ ID NO:14)     E  N  A  F- Y  M  H  D  EA MFE  M  P
vDREB1A_1      (SEQ ID NO:41)     X₁ X₂ A  F- X₃ M  H  D  EX₄ MFE X₅ X₆
vDREB1A_2      (SEQ ID NO:42)     X₇ X₈ X₉ F- X₁₀X₁₁X₁₂X₁₃EX₁₄MFX₁₅X₁₆X₁₇
vDREB1A_3      (SEQ ID NO:43)     X₁₈X₁₉ -  FE X₂₀-  -  -  EX₂₁MF-  X₂₂X₂₃
vDREB1A_4      (SEQ ID NO:44)     X₂₄X₂₅ -  FX₂₆X₂₇-  -  -  EX₂₈MF-  X₂₉X₃₀
vDREB1A_5      (SEQ ID NO:45)     X₃₁X₃₂ -  FX₃₃X₃₄-  -  -  EX₃₅MF-  X₃₆X₃₇
vDREB1A_6      (SEQ ID NO:46)     E  D  -  FE F  -  -  -  EA MF-  M  D
vDREB1A_7      (SEQ ID NO:125)    E  X₃₈ -  FE X₃₉-  -  -  EA MF-  M  X₄₀
```

Where:

$X_1$ = D or E  
$X_2$ = D or E  
$X_3$ = F or Y  
$X_4$ = Q or A  
$X_5$ = T or M  
$X_6$ = D or E $X_7$ = any  
$X_8$ = N, H, R, K, D, or E  
$X_9$ = any  
$X_{10}$ = F, Y, or W  
$X_{11}$ = any  
$X_{12}$ = any  
$X_{13}$ = any  
$X_{14}$ = any  
$X_{15}$ = any  
$X_{16}$ = any  
$X_{17}$ = P, H, R, K, D, or E $X_{18}$ = D or E  
$X_{19}$ = D or E  
$X_{20}$ = F or Y  
$X_{21}$ = Q or A  
$X_{22}$ = T or M  
$X_{23}$ = D or E $X_{24}$ = H, R, K, D, or E  
$X_{25}$ = D or E  
$X_{26}$ = D or E  
$X_{27}$ = F or Y  
$X_{28}$ = S, T, N, Q, C, G, P, A, V, L, I, F, Y, W, or M  
$X_{29}$ = S, T, N, Q, C, G, P, A, V, L, I, F, Y, W, or M  
$X_{30}$ = D or E $X_{31}$ = any  
$X_{32}$ = D, E, or N  
$X_{33}$ = any  
$X_{34}$ = F, Y, or W  
$X_{35}$ = any  
$X_{36}$ = any  
$X_{37}$ = D, E, or P $X_{38}$ = D, E, or N  
$X_{39}$ = F, Y, or W  
$X_{40}$ = D, E, or P

FIG. 8

```
CBF1
VP16 motif (SEQ ID NO:9)      D D  F  E F  E Q  M F -  T  D
Native CBF1 (SEQ ID NO:15)    D -  -  E -  E T  M F G  M  P
vCBF1_1 (SEQ ID NO:47)        D -  -  E -  E X₁ M F G  X₂ X₃
vCBF1_2 (SEQ ID NO:48)        D -  -  E -  E X₄ M F X₅ X₆ X₇
vCBF1_3 (SEQ ID NO:49)        D D  F  E F  E X₈ M F -  X₉ X₁₀
vCBF1_4 (SEQ ID NO:50)        D X₁₁ X₁₂ E X₁₃ E X₁₄ M F - X₁₅ X₁₆
vCBF1_5 (SEQ ID NO:51)        D X₁₇ X₁₈ E X₁₉ E X₂₀ M F - X₂₁ X₂₂
vCBF1_6 (SEQ ID NO:52)        D D  F  E F  E T  M F -  M  D
vCBF1_7 (SEQ ID NO:126)       D X₂₃ F  E X₂₄ E T  M F -  M  X₂₅
```

Where:

| | | |
|---|---|---|
| $X_1$ = Q or T | $X_4$ = any | $X_8$ = Q or T |
| $X_2$ = T or M | $X_5$ = any | $X_9$ = T or M |
| $X_3$ = D or E | $X_6$ = any | $X_{10}$ = D or E |
| | $X_7$ = D, E, or P | |

$X_{11}$ = D or E
$X_{12}$ = F, W, or Y
$X_{13}$ = F, W, or Y
$X_{14}$ = G, S, T, C, N, Q, or Y
$X_{15}$ = G, S, T, C, N, Q, Y, A, V, L, I, F, W, P, or M
$X_{16}$ = D or E $X_{17}$ = D or E
$X_{18}$ = any
$X_{19}$ = F, W, or Y
$X_{20}$ = any
$X_{21}$ = any
$X_{22}$ = D, E, or P $X_{23}$ = D or E
$X_{24}$ = F, W, or Y
$X_{25}$ = D, E, or P

FIG. 9

```
DOF1
VP16 motif (SEQ ID NO:9)      D D- FE F E  Q  M  - FT  D
Native DOF1 (SEQ ID NO:16)    E DS FV W P  A  A  S F-  D
vDOF1_1 (SEQ ID NO:53)        X₁ DS FX₂ X₃ X₄ X₅ X₆ S F- D
vDOF1_2 (SEQ ID NO:54)        X₇ DX₈ FX₉ X₁₀X₁₁X₁₂X₁₃X₁₄F- D
vDOF1_3 (SEQ ID NO:55)        X₁₅D- FX₁₆X₁₇X₁₈X₁₉X₂₀ - FT D
vDOF1_4 (SEQ ID NO:56)        X₂₁D- FX₂₂X₂₃X₂₄X₂₅X₂₆ - FX₂₇D
vDOF1_5 (SEQ ID NO:57)        X₂₈D- FX₂₉X₃₀X₃₁X₃₂X₃₃ - FX₃₄D
vDOF1_6 (SEQ ID NO:58)        E  D- FE F E  A  M  - FT  D
vDOF1_7 (SEQ ID NO:127)       E  D- FX₃₅X₃₆X₃₇A  X₃₈- FT D
```

Where:

$X_1$ = D or E  
$X_2$ = E or V  
$X_3$ = F or W  
$X_4$ = D or E  
$X_5$ = Q or A  
$X_6$ = M or A $X_7$ = any  
$X_8$ = any  
$X_9$ = any  
$X_{10}$ = F, W, or Y  
$X_{11}$ = D, E, or P  
$X_{12}$ = any  
$X_{13}$ = A, V, I, L, M, F, Y, or W  
$X_{14}$ = any $X_{15}$ = D or E  
$X_{16}$ = E or V  
$X_{17}$ = F or W  
$X_{18}$ = D or E  
$X_{19}$ = Q or A  
$X_{20}$ = M or A $X_{21}$ = H, R, K, D, or E  
$X_{22}$ = any  
$X_{23}$ = F, W, or Y  
$X_{24}$ = D or E  
$X_{25}$ = any  
$X_{26}$ = A, V, I, L, or M  
$X_{27}$ = S, T, N, Q, C, G, P, or Y $X_{28}$ = any  
$X_{29}$ = any  
$X_{30}$ = F, W, or Y  
$X_{31}$ = D, E, or P  
$X_{32}$ = any  
$X_{33}$ = A, V, I, L, M, F, Y, or W  
$X_{34}$ = any $X_{35}$ = E or V  
$X_{36}$ = F, W, or Y  
$X_{37}$ = D, E, or P  
$X_{38}$ = A, V, I, L, or M

PLANT TRANSACTIVATION INTERACTION MOTIFS AND USES THEREOF

CROSS-REFERENCE TO RELATED APPLICATION

This application is a continuation application of U.S. patent application Ser. No. 13/757,674 filed Feb. 1, 2013, now allowed, which claims the benefit of U.S. Provisional Patent. Application Ser. No. 61/594,245, filed Feb. 2, 2012, titled "Plant Transactivation Interaction Motifs and Uses Thereof."

FIELD OF THE DISCLOSURE

The present disclosure relates to plant biotechnology. Embodiments relate to polypeptides (e.g., a fusion protein) comprising a novel or synthetic transcription factor interaction motif from a plant transactivator. Some embodiments relate to the use of such a protein to express a nucleic acid of interest or to increase the expression of a nucleic acid of interest. Some embodiments relate to polynucleotides encoding a protein comprising a novel or synthetic transcription factor interaction motif from a plant transactivator. Particular examples relate to host cells, tissues, and/or organisms comprising a polypeptide or polynucleotide of the invention.

BACKGROUND

The introduction of cloned and isolated genes into plant cells (genetic transformation), and the subsequent regeneration of transgenic plants, is widely used to make genetic modifications of plants and plant materials. Genetic transformation of plants to introduce a desirable trait (e.g., improved nutritional quality; increased yield; pest or disease resistance; stress tolerance; and herbicide resistance) is now commonly used to produce new and improved transgenic plants that express the desirable trait. DNA is typically randomly introduced into the nuclear or plastid DNA of a eukaryotic plant cell, and cells containing the DNA integrated into the cell's DNA are then isolated and used to produce stably-transformed plant cells. Often, it is desirable to genetically engineer a single plant variety to express more than one introduced trait by introducing multiple coding sequences, which may comprise similar (or identical) regulatory elements.

The expression of transgenes (as well as endogenous genes) is controlled through mechanisms involving multiple protein-DNA and protein-protein interactions. Through such interactions, nucleic acid regulatory elements (e.g., promoters and enhancers) can impart patterns of expression to a coding sequence that are either constitutive or specific. For example, a promoter may lead to increased transcription of a coding sequence in specific tissues, during specific development periods, or in response to environmental stimuli. Unfortunately, the inherent attributes of conventional promoters for transgene expression limit the range of expression control that they may be used to exert in a host cell. One practical limitation of conventional promoters is that it is difficult to finely tune the expression level of an introduced gene due to limitations in promoter strength and to the silencing of transgene expression by particularly strong promoters or the simultaneous use in the same cell of many copies of the same promoter. It can also be desirable to initiate or increase expression of endogenous or native genes.

Transactivators are proteins that function by recruiting through protein-protein interactions a number of different proteins involved in DNA transcription (e.g., nucleo some-remodeling complexes; the mediator complex; and general transcription factors, such as TFIIB, TBP, and TFIIH) to initiate or enhance the rate of transcription by affecting nucleosome assembly/disassembly, pre-initiation complex formation, promoter clearance, and/or the rate of elongation. The protein-protein interactions of transactivators and their binding partners involve discrete internal structural elements within the transactivators known as "transactivation domains (TADs)." TADs are thought to share little primary sequence homology and adopt a defined structure only upon binding to a target. Sigler (1988) *Nature* 333:210-2. Though acidic and hydrophobic residues within the TADs are thought to be important (see, e.g., Cress and Triezenberg (1991) *Science* 251(4989):87-90), the contribution of individual residues to activity is thought to be small. Hall and Struhl (2002) *J. Biol. Chem.* 277:46043-50.

The Herpes Simplex virion protein 16 (VP16) is a transactivator that functions to stimulate transcription of viral immediate early genes in HSV-infected cells. As with other transactivators, VP16 activates transcription through a series of protein-protein interactions involving its TAD, which is highly acidic. The acidic TAD of VP16 has been shown to interact with several partner proteins both in vitro and in vivo. For example, the TAD of VP16 contains an interaction motif that interacts directly with the Tfb1 subunit of TFIIH (Langlois et al. (2008) *J. Am. Chem. Soc.* 130:10596-604), and this interaction is correlated with the ability of VP16 to activate both the initiation and elongation phase of transcription for viral immediate early genes.

BRIEF SUMMARY OF THE DISCLOSURE

Described herein are novel TAD protein-protein interaction motifs that have been isolated from plant transactivator proteins, and nucleic acids encoding the same. These novel interaction motifs may be utilized in a synthetic TAD to confer gene regulatory properties upon a polypeptide comprising the TAD. For example, some embodiments include a transcriptional activator fusion protein that comprises a DNA-binding domain polypeptide and such a TAD polypeptide. Depending upon the particular DNA-binding domain that is fused to the TAD in the transcriptional activator fusion protein, transactivation may be used to increase the expression of a gene of interest. For example, a heterologous polynucleotide to which the DNA-binding domain binds may be operably linked to the gene of interest, thereby targeting the fusion protein (and its functional TAD), the binding of which will increase the expression of the gene of interest. Alternatively, a DNA-binding domain may be engineered to bind an endogenous polynucleotide that is operably linked to, or proximal to, the gene of interest. Upon binding of a transcriptional activator fusion protein to a target DNA binding site, transcription of a gene operably linked to the target DNA binding site may be stimulated.

Also described herein are synthetic variant TAD protein-protein interaction motifs, and nucleic acids encoding the same. In some examples, a synthetic variant TAD protein-protein interaction motif is engineered by introducing one or more mutations (e.g., a conservative mutation, or a mutation identified in an ortholog of the interaction motif) into the TAD of a transactivator (e.g., a plant transactivator). Surprisingly, a synthetic variant TAD generated in this manner that comprises a variant interaction motif may confer gene regulatory properties different from the unmodified TAD when coupled to a DNA-binding domain in a transcriptional activator fusion protein. For example, particular synthetic variant TADs that comprise a variant interaction motif may enhance the level of transcriptional activation conferred by the naturally-occurring TAD interaction motif when expressed in the same position in a fusion protein comprising a DNA-binding domain.

Some embodiments include a synthetic transcriptional activator fusion protein. In particular embodiments, the fusion protein may increase transcription of a gene of interest, wherein the fusion protein comprises a first polypeptide comprising a DNA-binding domain operatively linked to a second polypeptide comprising a TAD interaction motif. In some examples, the TAD interaction motif may be selected from the group of TAD interaction motifs consisting of SEQ ID NOs:10-16. For example and without limitation, the TAD interaction motif may be comprised within a TAD comprising an amino acid sequence selected from the group consisting of SEQ ID NOs:2-8 and SEQ ID NOs:100-106. In some examples, the TAD interaction motif may be a variant TAD interaction motif having, for example and without limitation, an amino acid sequence selected from the group consisting of SEQ ID NOs:17-58. For example and without limitation, such a variant TAD interaction motif may be comprised within a TAD comprising an amino acid sequence selected from the group consisting of SEQ ID NOs:107-120.

Some embodiments include a polynucleotide that encodes a synthetic transcriptional activator fusion protein comprising a first polypeptide comprising a DNA-binding domain operatively linked to a second polypeptide comprising a TAD interaction motif A DNA-binding domain polypeptide may be any DNA-binding domain that binds specifically to a particular target DNA binding site. For example and without limitation, the DNA-binding domain polypeptide may be a polypeptide selected from the group consisting of a zinc finger DNA-binding domain; UPA DNA-binding domain; GAL4; TAL; LexA; a Tet repressor; LacR; and a steroid hormone receptor. In particular examples, a DNA-binding domain-encoding sequence may be selected from the group consisting of SEQ ID NO:67; SEQ ID NO:68; and SEQ ID NO:99. In particular examples, the polynucleotide may comprise a DNA-binding protein-encoding sequence that is at least 80%, 85%, 90%, 95%, 98%, or 100% identical to a sequence selected from the group consisting of SEQ ID NO:67; SEQ ID NO:68; and SEQ ID NO:99.

In some examples, the polynucleotide may comprise a TAD interaction motif-encoding sequence that encodes a TAD interaction motif or variant TAD interaction motif, e.g., having a sequence selected from SEQ ID NOs:10-58. Particular embodiments include a polynucleotide that encodes a transcriptional activator fusion protein comprising at least one TAD interaction motif. Particular embodiments include a polynucleotide that encodes a transcriptional activator fusion protein comprising at least one DNA-binding domain.

Examples of polynucleotides that encode a synthetic transcriptional activator fusion protein according to some embodiments of the invention include polynucleotides comprising at least one nucleotide sequence encoding a DNA-binding domain and at least one nucleotide sequence encoding a TAD interaction motif (or variant thereof), wherein the polynucleotide comprises, for example and without limitation, at least one nucleotide sequence selected from the group consisting of: SEQ ID NOs:79-93; a nucleotide sequence that is substantially identical to one of SEQ ID NOs:79-93; a nucleotide sequence having at least 80% sequence identity to one of SEQ ID NOs:79-93; a nucleotide sequence having at least 85% sequence identity to one of SEQ ID NOs:79-93; a nucleotide sequence having at least 90% sequence identity to one of SEQ ID NOs:79-93; a nucleotide sequence having at least 95% sequence identity to one of SEQ ID NOs:79-93; a nucleotide sequence having at least 97% sequence identity to one of SEQ ID NOs:79-93; a nucleotide sequence having at least 98% sequence identity to one of SEQ ID NOs:79-93; a nucleotide sequence having at least 99% sequence identity to one of SEQ ID NOs:79-93; the complement of a polynucleotide that is specifically hybridizable to at least one of SEQ ID NOs:79-93; and the reverse complement of a polynucleotide that is specifically hybridizable to at least one of SEQ ID NOs:79-93.

In some embodiments, a polynucleotide that encodes a transcriptional activator fusion protein may be incorporated into a recombinant vector, for example, to provide expression of the protein in a host cell. Accordingly, some examples include a vector comprising at least one polynucleotide of the invention, and/or a host cell into which such a vector has been introduced.

Also described herein are means for transactivation of plant gene expression. As used herein, a "means for transactivation of plant gene expression" includes a polypeptide selected from the group consisting of SEQ ID NO:10; SEQ ID NO:11; SEQ ID NO:14; SEQ ID NO:15; SEQ ID NO:22; SEQ ID NO:28; SEQ ID NO:46; and SEQ ID NO:52. In some embodiments, a synthetic protein comprising at least one means for transactivation of plant gene expression may be used to modulate the expression of a gene of interest in a plant cell.

Additionally, described herein are means for increasing gene expression that are derived from ERF2. As used herein, a "means for increasing gene expression that is derived from ERF2" includes a polypeptide selected from the group consisting of SEQ ID NOs:17-22 and SEQ ID NO:121. Additionally described are means for increasing gene expression that are derived from PTI4. As used herein, a "means for increasing gene expression that is derived from PTI4" includes a polypeptide selected from the group consisting of SEQ ID NOs:23-28 and SEQ ID NO:122. Additionally described are means for increasing gene expression that are derived from AtERF1. As used herein, a "means for increasing gene expression that is derived from AtERF1" includes a polypeptide selected from the group consisting of SEQ ID NOs:29-34 and SEQ ID NO:123. Additionally described are means for increasing gene expression that are derived from ORCA2. As used herein, a "means for increasing gene expression that is derived from ORCA2" includes a polypeptide selected from the group consisting of SEQ ID NOs:35-40 and SEQ ID NO:124. Additionally described are means for increasing gene expression that are derived from DREB1A. As used herein, a "means for increasing gene expression that is derived from DREB1A" includes a polypeptide selected from the group consisting of SEQ ID NOs:41-46 and SEQ ID NO:125. Additionally described are means for increasing gene expression that are derived from CBF1. As used herein, a "means for increasing gene expression that is derived from CBF1" includes a polypeptide selected from the group consisting of SEQ ID NOs:47-52 and SEQ ID NO:126. Additionally described are means for increasing gene expression that are derived from DOF1. As used herein, a "means for increasing gene expression that is derived from DOF1" includes a polypeptide selected from the group consisting of SEQ ID NOs:53-58 and SEQ ID NO:127.

Also described herein are methods for increasing gene expression utilizing a synthetic transcriptional activator fusion protein. In examples, an expression vector comprising a polynucleotide encoding a synthetic transcriptional activator fusion protein may be introduced into a host cell (e.g., a plant cell, yeast cell, mammalian cell, and immortalized cell) comprising a gene of interest operably linked to a target DNA binding site for the fusion protein. Expression of the fusion protein in the host cell, and subsequent binding of the fusion protein to the operably linked target DNA binding site, may result in transcription initiation or increased transcription of the gene of interest. In particular examples, the target DNA binding site may be introduced into the host cell, such that the target DNA binding site is operably linked to the gene of interest. In further examples, a synthetic transcriptional activator fusion protein may comprise a DNA-binding domain polypeptide that is engineered to bind to a target DNA binding site that is operably linked to the gene of interest.

In some embodiments, a vector comprising a polynucleotide encoding a synthetic transcriptional activator fusion protein may be introduced into a host cell, such that the polynucleotide is subsequently integrated into the genomic DNA of the host cell (e.g., via homologous recombination). Thus, a synthetic transcriptional activator fusion protein, and moreover a nucleic acid encoding the same, may be comprised within a transgenic organism (e.g., a transgenic plant). Accordingly, such transgenic organisms are also described herein. In examples, a nucleic acid encoding a synthetic transcriptional activator fusion protein may be either integrated randomly, or at a predetermined location, in the genome of a cell in the transgenic organism.

Further described are methods for expressing a gene of interest utilizing a synthetic transcriptional activator fusion protein and/or a nucleic acid encoding the same. In some embodiments, a vector comprising a polynucleotide encoding a synthetic transcriptional activator fusion protein may be introduced into a host cell comprising a gene of interest operably linked to a target DNA binding site for the fusion protein. In some examples, the synthetic transcriptional activator fusion protein comprises a means for transactivation of plant gene expression. After the vector is introduced into the host cell, expression of the gene of interest may be initiated or increased, thereby producing the expression product of the gene of interest in the host cell, for example, in an amount according to the regulatory control of the fusion protein. Such expression products may be isolated and/or purified from the host cell according to any method known in the art.

The foregoing and other features will become more apparent from the following detailed description of several embodiments, which proceeds with reference to the accompanying figures.

BRIEF DESCRIPTION OF THE FIGURES

FIG. 1 includes an identified interaction motif of the VP16 transactivation domain (TAD), subdomain II (SEQ ID NO:9). The asterisks indicate the amino acids of VP16 transactivation domain, subdomain II, which are proposed to directly contact the Tfb1 subunit of TFIIH as proposed by Langlois et al. (2008) 1 Am. Chem. Soc. 130:10596-604.

FIG. 2 includes an alignment of the VP16 transactivation subdomain II with the identified plant TADs. The listed plant TADs contain an interaction motif. The aligned interaction motifs are highlighted. The residues of the interaction motif of subdomain II from VP16 that have been proposed to contact transcription factors are marked with an asterisk (*).

FIG. 3 includes an alignment showing modifications that may be introduced into the TAD interaction motif of ERF2 to produce a variant ERF2 interaction motif. The sequences of the native ERF2 and VP16 interaction motifs are listed for comparison. The direct contacts are highlighted.

FIG. 4 includes an alignment showing modifications that may be introduced into the TAD interaction motif of PTI4 to produce a variant PTI4 interaction motif. The sequences of the native PTI4 and VP16 interaction motifs are listed for comparison. The direct contacts are highlighted.

FIG. 5 includes an alignment showing modifications that may be introduced into the TAD interaction motif of AtERF1 to produce a variant AtEFR1 interaction motif. The sequences of the native AtERF1 and VP16 interaction motifs are listed for comparison. The direct contacts are highlighted.

FIG. 6 includes an alignment showing modifications that may be introduced into the TAD interaction motif of ORCA2 to produce a variant ORCA2 interaction motif. The sequences of the native ORCA2 and VP16 interaction motifs are listed for comparison. The direct contacts are highlighted.

FIG. 7 includes an alignment showing modifications that may be introduced into the TAD interaction motif of DREB1A to produce a variant DREB1A interaction motif. The sequences of the native DREB1A and VP16 interaction motifs are listed for comparison. The direct contacts are highlighted.

FIG. 8 includes an alignment showing modifications that may be introduced into the TAD interaction motif of CBF1 to produce a variant CBF1 interaction motif. The sequences of the native CBF1 and VP16 interaction motifs are listed for comparison. The direct contacts are highlighted.

FIG. 9 includes an alignment showing modifications that may be introduced into the TAD interaction motif of DOF1 to produce a variant DOF1 interaction motif. The sequences of the native DOF1 and VP16 interaction motifs are listed for comparison. The direct contacts are highlighted.

SEQUENCE LISTING

Figure 10:
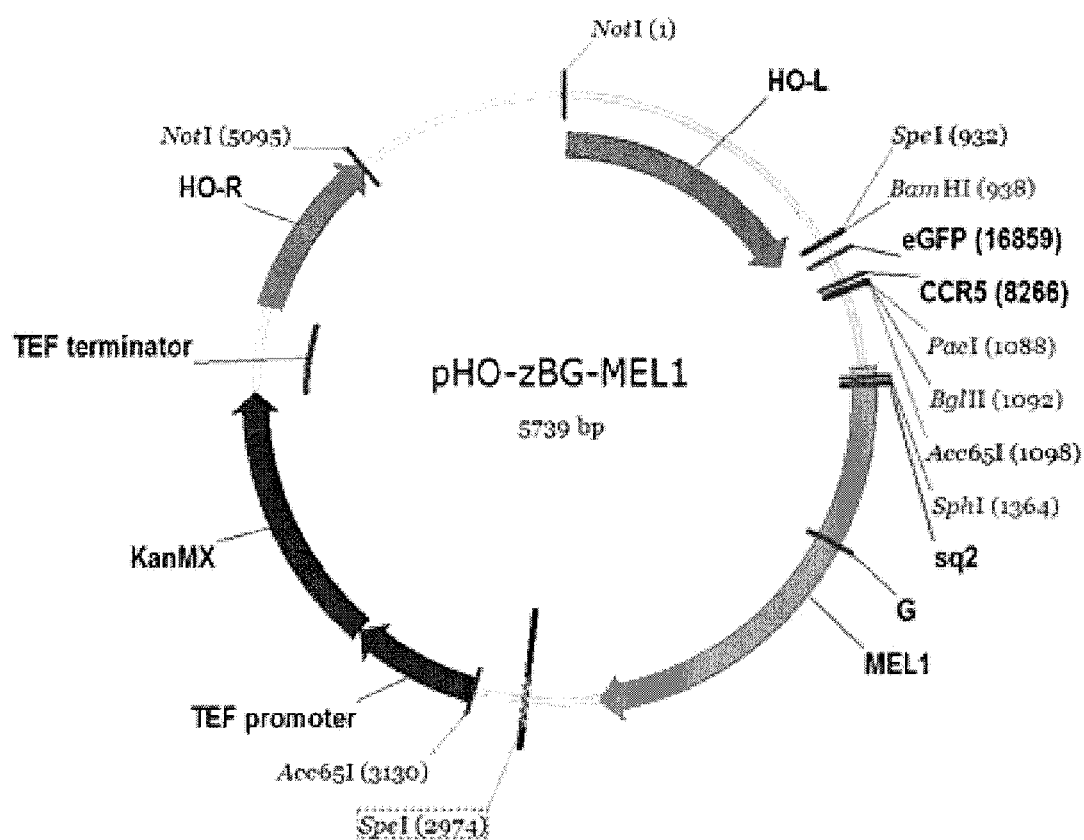
FIG. 10 includes a map of yeast integration vector, pHO-zBG-MEL1, which contains the HAS (High Affinity Site) ZFP binding sites upstream of a MEL1 reporter gene. The vector was targeted to the S. cerevisiae HO locus, and contained a KanMX resistance gene for selection in both yeast and bacteria.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NO:1 shows a VP16 plant transactivation domain containing an interaction motif (underlined):

GMTHDPVSYGALDV<u>DDFEFEQMFTD</u>ALGIDDFGG

SEQ ID NO:2 shows a ERF2 plant transactivation domain containing an interaction motif (underlined):

NDSEDMLVYGLLK<u>DAFHFDTSSSD</u>LSCLFDFPA

SEQ ID NO:3 shows a PTI4 Want transactivation domain containing an interaction motif (underlined):

CLTETWGDLPLKV<u>DDSEDMVIYGLLKD</u>ALSVGWSPFSFTAG

SEQ ID NO:4 shows a AtERF1 plant transactivation domain containing an interaction motif (underlined):

CFTESWGDLPLK<u>ENDSEDMLV</u>YGILNDAFHGG

SEQ ID NO:5 shows a ORCA2 plant transactivation domain containing an interaction motif (underlined):

FNENCEEIISPNYAS<u>EDLSDIILTD</u>IFKDQDNYEDE

SEQ ID NO:6 shows a DREB1A plant transactivation domain containing an interaction motif (underlined):

GFDMEETLVEAIYTAEQS<u>ENAFYMHDEAMFEMPS</u>LLANMAEGM

SEQ ID NO:7 shows a CBF1 plant transactivation domain containing an interaction motif (underlined):

EQSEGAFYM<u>DEETMFGMP</u>TLLDNMAEG

SEQ ID NO:8 shows a DOF1 plant transactivation domain containing an interaction motif (underlined):

SAGKAVLDD<u>EDSFVWPAASFD</u>MGACWAGAGFAD

SEQ ID NO:9 shows subdomain II of a VP16 transactivation domain, which is the interaction motif within SEQ ID NO:1:

DDFEFEQMFTD

SEQ ID NO:10 shows a ERF2 plant transactivation domain interaction motif:

DAFHFDTSSSD

SEQ ID NO:11 shows a PTI4 plant transactivation domain interaction motif:

DDSEDMVIYGLLKD

SEQ ID NO:12 shows a AtERF1 plant transactivation domain interaction motif:

ENDSEDMLV

SEQ ID NO:13 shows a ORCA2 plant transactivation domain interaction motif:

EDLSDIILTD

SEQ ID NO:14 shows a DREB1A plant transactivation domain interaction motif:

ENAFYMHDEAMFEMP

SEQ ID NO:15 shows a CBF1 plant transactivation domain interaction motif:

DEETMFGMP

SEQ ID NO:16 shows a DOF1 plant transactivation domain interaction motif:

EDSFVWPAASFD

SEQ ID NOs:17-22 show variant ERF2 plant transactivation domain interaction motif sequences.
SEQ ID NOs:23-28 show variant PTI4 plant transactivation domain interaction motif sequences.
SEQ ID NOs:29-34 show variant AtERF1 plant transactivation domain interaction motif sequences.

SEQ ID NOs:35-40 show variant ORCA2 plant transactivation domain interaction motif sequences.

SEQ ID NOs:41-46 show variant DREB1A plant transactivation domain interaction motif sequences.

SEQ ID NOs:47-52 show variant CBF1 plant transactivation domain interaction motif sequences.

SEQ ID NOs:53-58 show variant DOF1 plant transactivation domain interaction motif sequences.

SEQ ID NOs:59-66 show primers used for the construction of plasmid, pHO-zBG-MEL1.

SEQ ID NO:67 shows a Z6 DNA binding domain polynucleotide sequence:

TGTGGTGGGAGAGGAGGGTGG

SEQ ID NO:68 shows an 8× tandem repeat sequence of a Z6 DNA binding domain:

GGTGTGGTGGGAGAGGAGGGTGGGAGTGTGGTGGGAGAGGAGGGTGGCTCT
GTGGTGGGAGAGGAGGGTGGAGATGTGGTGGGAGAGGAGGGTGGTCTTGTG
GTGGGAGAGGAGGGTGGGGATGTGGTGGGAGAGGAGGGTGGCCTTGTGGTG
GGAGAGGAGGGTGGAGGTGTGGTGGGAGAGGAGGGTGGCTTAAGCCGC

SEQ ID NOs:69-74 show primers and probes used in pat and pal HP assays.

SEQ ID NOs:75-78 show primers used for PCR analysis of PTUs in tobacco.

SEQ ID NO:79 shows a synthetic nucleotide sequence encoding a native plant transactivation domain interaction motif from VP16 that was fused to a Z6 Zinc Finger binding Protein:

GGCATGACCCATGATCCTGTGTCTTATGGAGCCTTGGATGTTGATGACTT
TGAGTTTGAGCAGATGTTCACAGATGCACTGGGCATCGATGACTTTGGTG
GA

SEQ ID NO:80 shows a synthetic nucleotide sequence (v3) encoding a native plant transactivation domain interaction motif from ERF2 that was fused to a Z6 Zinc Finger binding Protein:

AATGACTCTGAGGACATGCTGGTGTATGGTTTGCTCAAGGATGCCTTTCA
CTTTGACACCTCCAGCTCAGACCTCTCCTGCCTCTTTGACTTCCCAGCC

SEQ ID NO:81 shows a synthetic nucleotide sequence (v3) encoding a native plant transactivation interaction motif from PTI4 that was fused to a Z6 Zinc Finger binding Protein:

TGCCTGACAGAAACTTGGGGAGACTTGCCTCTCAAGGTTGATGACTCTGA
GGACATGGTGATCTATGGTCTGTTGAAGGATGCACTCTCAGTGGGGTGGT
CCCCATTCTCTTTCACGGCTGGT

SEQ ID NO:82 shows a synthetic nucleotide sequence (v3) encoding a native plant transactivation domain interaction motif from AtERF1 that was fused to a Z6 Zinc Finger binding Protein:

TGCTTCACGGAATCCTGGGGAGACCTTCCTTTGAAGGAGAATGACTCTGA
GGACATGTTGGTGTACGGAATCCTCAATGATGCTTTTCATGGTGGC

SEQ ID NO:83 shows a synthetic nucleotide sequence (v3) encoding a native plant transactivation domain interaction motif from ORCA2 that was fused to a Z6 Zinc Finger binding Protein:

TTCAATGAGAATTGTGAAGAAATCATCTCTCCAAACTACGCATCAGAGGA
CTTGTCTGACATCATCTTGACGGACATCTTCAAGGACCAAGACAACTATG
AGGATGAG

SEQ ID NO:84 shows a synthetic nucleotide sequence (v3) encoding a native plant transactivation domain interaction motif from DREB1A that was fused to a Z6 Zinc Finger binding Protein:

GGCTTTGACATGGAAGAAACATTGGTGGAGGCCATCTACACTGCTGAACA
GAGCGAGAATGCCTTCTACATGCATGATGAGGCAATGTTTGAGATGCCAT
CTCTTCTGGCCAACATGGCTGAGGGAATG

SEQ ID NO:85 shows a synthetic nucleotide sequence (v3) encoding a native plant transactivation domain interaction motif from CBF1 that was fused to a Z6 Zinc Finger binding Protein:

GAACAGTCAGAAGGTGCTTTCTACATGGATGAAGAGACCATGTTTGGGAT
GCCAACCCTTCTGGATAACATGGCAGAGGGA

SEQ ID NO:86 shows a synthetic nucleotide sequence (v3) encoding a native plant transactivation domain interaction motif from DOF1 that was fused to a Z6 Zinc Finger binding Protein:

TCAGCTGGGAAGGCAGTCTTGGATGATGAGGACAGCTTTGTTTGGCCTGC
TGCATCCTTTGACATGGGTGCCTGCTGGGCTGGAGCTGGCTTTGCTGAC

SEQ ID NO:87 shows a synthetic nucleotide sequence (v2) encoding an exemplary variant plant transactivation domain interaction motif from ERF2 that was fused to a Z6 Zinc Finger binding Protein:

AATGACTCTGAGGACATGCTGGTGTATGGTTTGCTCAAGGATGATTTCCA
CTTTGAGACAATGTTCTCAGACCTGTCCTGCCTCTTTGACTTCCCAGCC

SEQ ID NO:88 shows a synthetic nucleotide sequence (v2) encoding an exemplary variant plant transactivation domain interaction motif from PTI4 that was fused to a Z6 Zinc Finger binding Protein:

TGCCTGACAGAAACTTGGGGAGACTTGCCTCTCAAGGTTGATGACTTTGA
GTTTGAGATGATGTTCACAGATGCACTCTCAGTGGGGTGGTCCCCATTCT
CTTTCACGGCTGGT

SEQ ID NO:89 shows a synthetic nucleotide sequence (v2) encoding an exemplary variant plant transactivation domain interaction motif from AtERF1 that was fused to a Z6 Zinc Finger binding Protein:

TGCTTCACGGAATCCTGGGGAGACCTTCCTTTGAAGGAGAATGACTTTGA
GTTTGAAATGTTCACAGATTACGGAATCCTCAATGATGCTTTTCATGGTG
GC

SEQ ID NO:90 shows a synthetic nucleotide sequence (v2) encoding an exemplary variant plant transactivation domain interaction motif from ORCA2 that was fused to a Z6 Zinc Finger binding Protein:

TTCAATGAGAATTGTGAAGAAATCATCTCTCCAAACTACGCATCAGAGGA
CTTTGATCTTGAGATGTTGACGGACATCTTCAAGGACCAAGACAACTATG
AGGATGAG

SEQ ID NO:91 shows a synthetic nucleotide sequence (v2) encoding an exemplary variant plant transactivation domain interaction motif from DREB1A that was fused to a Z6 Zinc Finger binding Protein:

GGCTTTGACATGGAAGAAACATTGGTGGAGGCCATCTACACTGCTGAACA
GAGCGAGGACTTTGAGTTTGAAGCAATGTTCATGGATTCTCTTCTGGCCA
ACATGGCTGAGGGAATG

SEQ ID NO:92 shows a synthetic nucleotide sequence (v2) encoding an exemplary variant plant transactivation domain interaction motif from CBF1 that was fused to a Z6 Zinc Finger binding Protein:

GAACAGTCAGAAGGTGCTTTCTACATGGATGACTTTGAGTTCGAGACAAT
GTTCATGGACACCCTTCTGGATAACATGGCAGAGGGA

SEQ ID NO:93 shows a synthetic nucleotide sequence (v2) encoding an exemplary variant plant transactivation domain interaction motif from DOF1 that was fused to a Z6 Zinc Finger binding Protein:

TCAGCTGGGAAGGCAGTCTTGGATGATGAGGACTTTGAGTTTGAAGCCAT
GTTCACGGACATGGGTGCCTGCTGGGCTGGAGCTGGCTTTGCTGAC

SEQ ID NOs:94-98 show primers and probes used in gus and BYEEF HP assays.

SEQ ID NO:99 shows a tandem repeat sequence taken from the consensus binding sequence of AVRBS3-inducible genes, and termed the UPA DNA binding domain:

TATATAAACCTNNCCCTCT

SEQ ID NO:100 shows an exemplary synthetic transactivation domain comprising a ERF2 plant transactivation domain interaction motif (underlined):

GMTHDPVSYGALDV<u>DAFHFDTSSSD</u>ALGIDDFGG

SEQ ID NO:101 shows an exemplary synthetic transactivation domain comprising a PTI4 plant transactivation domain interaction motif (underlined):

GMTHDPVSYGALDV<u>DDSEDMVIYGLLKD</u>ALGIDDFGG

SEQ ID NO:102 shows an exemplary synthetic transactivation domain comprising a AtERF1 plant transactivation domain interaction motif (underlined):

GMTHDPVSYGALDV<u>ENDSEDMLV</u>ALGIDDFGG

SEQ ID NO:103 shows an exemplary synthetic transactivation domain comprising a ORCA2 plant transactivation domain interaction motif (underlined):

GMTHDPVSYGALDV<u>EDLSDIILTD</u>ALGIDDFGG

SEQ ID NO:104 shows an exemplary synthetic transactivation domain comprising a DREB1A plant transactivation domain interaction motif (underlined):

GMTHDPVSYGALDV<u>ENAFYMHDEAMFEMP</u>ALGIDDFGG

SEQ ID NO:105 shows an exemplary synthetic transactivation domain comprising a CBF1 plant transactivation domain interaction motif (underlined):

GMTHDPVSYGALDV<u>DEETMFGMP</u>ALGIDDFGG

SEQ ID NO:106 shows an exemplary synthetic transactivation domain comprising a DOF1 plant transactivation domain interaction motif (underlined):

GMTHDPVSYGALDV<u>EDSFVWPAASFD</u>ALGIDDFGG

SEQ ID NO:107 shows an exemplary synthetic transactivation domain comprising a variant ERF2 plant transactivation domain interaction motif (underlined):

GMTHDPVSYGALDV<u>DDFHFETMFSD</u>ALGIDDFGG

SEQ ID NO:108 shows a further exemplary synthetic transactivation domain comprising a variant ERF2 plant transactivation domain interaction motif (underlined):

NDSEDMLVYGLLK<u>DDFHFETMFSD</u>LSCLFDFPA

SEQ ID NO:109 shows an exemplary synthetic transactivation domain comprising a variant PTI4 plant transactivation domain interaction motif (underlined):

GMTHDPVSYGALDV<u>DDFEFEMMFTD</u>ALGIDDFGG

SEQ ID NO:110 shows a further exemplary synthetic transactivation domain comprising a variant PTI4 plant transactivation domain interaction motif (underlined):

CLTETWGDLPLKV<u>DDFEFEMMFTD</u>ALSVGWSPFSFTAG

SEQ ID NO:111 shows an exemplary synthetic transactivation domain comprising a variant AtERF1 plant transactivation domain interaction motif (underlined):

GMTHDPVSYGALDV<u>ENDFEFEMFTD</u>ALGIDDFGG

SEQ ID NO:112 shows a further exemplary synthetic transactivation domain comprising a variant AtERF1 plant transactivation domain interaction motif (underlined):

CFTESWGDLPLK<u>ENDFEFEMFTD</u>YGILNDAFHGG

SEQ ID NO:113 shows an exemplary synthetic transactivation domain comprising a variant ORCA2 plant transactivation domain interaction motif (underlined):

GMTHDPVSYGALDV<u>EDFDLEMLTD</u>ALGIDDFGG

SEQ ID NO:114 shows a further exemplary synthetic transactivation domain comprising a variant ORCA2 plant transactivation domain interaction motif (underlined):

FNENCEEIISPNYAS<u>EDFDLEMLTDI</u>FKDQDNYEDE

SEQ ID NO:115 shows an exemplary synthetic transactivation domain comprising a variant DREB1A plant transactivation domain interaction motif (underlined):

GMTHDPVSYGALDV<u>EDFEFEAMFMD</u>ALGIDDFGG

SEQ ID NO:116 shows a further exemplary synthetic transactivation domain comprising a variant DREB1A plant transactivation domain interaction motif (underlined):

GFDMEETLVEAIYTAEQS<u>EDFEFEAMFMD</u>SLLANMAEGM

SEQ ID NO:117 shows an exemplary synthetic transactivation domain comprising a variant CBF1 plant transactivation domain interaction motif (underlined):

GMTHDPVSYGALDV<u>DDFEFETMFMD</u>ALGIDDFGG

SEQ ID NO:118 shows a further exemplary synthetic transactivation domain comprising a variant CBF1 plant transactivation domain interaction motif (underlined):

EQSEGAFYM<u>DDFEFETMFMD</u>TLLDNMAEG

SEQ ID NO:119 shows an exemplary synthetic transactivation domain comprising a variant DOF1 plant transactivation domain interaction motif (underlined):

GMTHDPVSYGALDV<u>EDFEFEAMFTD</u>ALGIDDFGG

SEQ ID NO:120 shows a further exemplary synthetic transactivation domain comprising a variant DOF1 plant transactivation domain interaction motif (underlined):

SAGKAVLDD<u>EDFEFEAMFTD</u>MGACWAGAGFAD

SEQ ID NOs:121-127 show variant plant transactivation domain interaction motif sequences.

DETAILED DESCRIPTION

I. Overview of Several Embodiments

Disclosed herein are novel plant transactivation domains (TADs), TAD interaction motifs, and synthetic variants of the foregoing that may be useful as transcriptional activators, and that may be fused in a synthetic transcriptional activator fusion protein with a DNA-binding polypeptide for transcriptional activation of a gene of interest. Particular novel plant TADs and TAD interaction motifs disclosed herein have been isolated from the plant proteins, ERF2; PTI4; AtERF1; ORCA2; DREB1A; CBF1; and DOF1. Synthetic transcriptional activator fusion proteins comprising novel plant TAD and/or TAD interaction motif as described herein may be utilized in particular embodiments to increase (e.g., initiate) gene expression in a variety of cells (e.g., yeast cells and plant cells), and for virtually any gene.

Transactivation domains are functionally autonomous; i.e., a single TAD can regulate transcription when fused to one of many different heterologous DNA-binding domains, and when tethered at different positions in a promoter region. Hall and Struhl (2002), supra. TADs are believed to share little primary sequence homology and adopt a defined structure only upon binding to a target. Sigler (1988), supra. Though acidic and hydrophobic residues within the TADs are thought to be important (see, e.g., Cress and Triezenberg (1991), supra), the contribution of individual residues to activity is believed to be small. Hall and Struhl (2002), supra.

It is difficult to predict a priori if a synthetic transactivation domain interaction motif will function to initiate or enhance expression in a plant cell. This unpredictability may be at least in part a consequence of the fact that some TADs are very strong transactivators that may result in "squelching" (e.g., by titrating components of the cellular transcriptional machinery) as a function both of its intracellular concentration and the strength of its TADs. See, e.g., U.S. Pat. No. 6,271,341 (mutant VP16 TADs with graded gene regulation).

Disclosed herein is the unexpected finding that certain novel plant TADs and TAD interaction motifs sharing sequence homology with the VP16 TAD confer very different levels of regulation upon genes under their control. Using a generalizable strategy for "swapping" TADs to produce synthetic transcriptional activator fusion proteins, it was surprisingly found that novel TADs and TAD interaction motifs isolated from PTI4, DREB1A, ERF2, and CBF1 are able to provide greater increases in gene transcription in a plant cell than is provided by VP16, which is recognized in the art as being a very good transactivator. It was also found that novel TADs and TAD interaction motifs from AtERF1, ORCA2, and DOF1 provide lesser increases in gene transcription.

Also disclosed herein is the unexpected finding that variant TADs and TAD interaction motifs comprising very few and minor amino acid changes with regard to the native sequence may provide further enhancement or tuning of the gene regulatory properties exhibited by the native TAD. For example, it was surprisingly found that variant ERF2 and CBF1 TAD interaction motifs lead to significantly greater transcription of a gene under its control than the corresponding native interaction motif in plants.

II. Abbreviations chs chalcone synthase gene
HAS high affinity site
HP hydrolysis probe
HSV Herpes Simplex Virus
MS Murashige and Skoog
PNPG p-nitrophenyl-alpha-D-glucopyranoside
PTU plant transcriptional unit
SSC saline-sodium citrate
TAD transactivation domain
TBP TATA-binding protein
T-DNA transfer DNA
TFIIB transcription factor IIB TFIIH transcription factor IIH
T$_i$ tumor-inducing (plasmids derived from *A. tumefaciens*)
UAS upstream activation sequence
VP16 Herpes Simplex Virion Protein 16

III. Terms

In order to facilitate review of the various embodiments of the disclosure, the following explanations of specific terms are provided:

Endogenous: As used herein, the term "endogenous" refers to substances (e.g., nucleic acid molecules and polypeptides) that originate from within a particular organism, tissue, or cell. For example, an "endogenous" polypeptide expressed in a plant cell may refer to a polypeptide that is normally expressed in cells of the same type from non-genetically engineered plants of the same species. Likewise, an "endogenous" nucleic acid comprised in a plant cell may refer to a nucleic acid (e.g., genomic DNA) that is normally found in cells of the same type from non-genetically engineered plants of the same species.

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell (e.g., a protein). Gene expression can be influenced by external signals; for example, exposure of a cell, tissue, or organism to an agent that increases or decreases expression of a gene comprised therein. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations of any of the foregoing. Gene expression can be measured at the RNA level or the protein level by methods known in the art, including, without limitation, Northern blot, RT-PCR, Western blot, and in vitro, in situ, or in vivo protein activity assay(s).

Increase expression: As used herein, the term "increase expression" refers to initiation of expression, as well as to a quantitative increase in the amount of an expression product produced from a template construct. In some embodiments, a polypeptide comprising a TAD may be used to "increase expression" from a nucleic acid. In such embodiments, the increase in expression may be determined by comparison with the amount of expression product produced in a control (e.g., from the construct in the absence of the protein comprising the plant transactivation domain).

Fusion protein: As used herein, the term "fusion protein" refers to a molecule comprising at least two operatively linked polypeptides. In certain examples, the two operatively linked polypeptides may be normally expressed as part of different gene products (e.g., in different organisms). In further examples, the at least two operatively linked polypeptides may be derived from polypeptides normally expressed as part of different gene products. The operatively linked polypeptides present in a fusion protein described herein typically interact with at least one target protein or nucleic acid in a cell wherein the fusion protein is to be expressed. For example, an operatively linked polypeptide may interact with one or more transcription factor(s) or proteinaceous element(s) of the cellular transcription machinery, or it may interact with a specific polynucleotide or structural element of a nucleic acid.

Heterologous: As used herein, the term "heterologous" refers to substances (e.g., nucleic acid molecules and polypeptides) that do not originate from within a particular organism, tissue, or cell. For example, a "heterologous" polypeptide expressed in a plant cell may refer to a polypeptide that is not normally expressed in cells of the same type from non-genetically engineered plants of the same species (e.g., a polypeptide that is expressed in different cells of the same organism or cells of a different organism).

Isolated: An "isolated" biological component (such as a nucleic acid or protein) has been substantially separated, produced apart from, or purified away from other biological components in the cell of the organism in which the component naturally occurs (e.g., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" may include nucleic acid molecules and proteins purified by standard purification methods. The term embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

An "exogenous" molecule is a molecule that is not native to a specified system (e.g., a germplasm, variety, elite variety, and/or plant) with respect to nucleotide sequence and/or genomic location for a polynucleotide, and with respect to amino acid sequence and/or cellular localization for a polypeptide. In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Some embodiments employ a particular form of nucleic acid, an oligonucleotide. Oligonucleotides are relatively short nucleic acid molecules, typically comprising 50 or fewer nucleobases (though some oligonucleotides may comprise more than 50). An oligonucleotide may be formed by cleavage (e.g., restriction digestion) of a longer nucleic acid comprising the oligonucleotide sequence, or it may be chemically synthesized, in a sequence-specific manner, from individual nucleoside phosphoramidites.

An oligonucleotide may be used as a probe sequence to detect a nucleic acid molecule comprising a particular nucleotide sequence. According to the foregoing, an oligonucleotide probe may be prepared synthetically or by cloning. Suitable cloning vectors are known to those of skill in the art. An oligonucleotide probe may be labeled or unlabeled. A wide variety of techniques exist for labeling nucleic acid molecules, including, for example and without limitation, radiolabeling by nick translation; random priming; and tailing with terminal deoxytransferase, where the nucleotides employed are labeled, for example, with radioactive $^{32}P$. Other labels that may be used include, for example and without limitation: fluorophores; enzymes; enzyme substrates; enzyme cofactors; and enzyme inhibitors. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) *Proc. Natl. Acad. Sci. USA* 80:4045-9.

Some embodiments of the invention include a polynucleotide that is "specifically hybridizable" or "specifically complementary" to a nucleotide target sequence. "Specifically hybridizable" and "specifically complementary" are terms that indicate a sufficient degree of complementarity such that stable and specific binding occurs between the polynucleotide and the nucleic acid molecule comprising the particular nucleotide target sequence. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will contribute to the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization for 1 hour at 65° C. in a PerfectHyb™ plus hybridization buffer (Sigma-Aldrich), followed by 40 minute sequential washes at 65° C. in 0.1×SSC/0.1% SDS.

Operably linked nucleotide sequences: A first nucleotide sequence is "operably linked" with or to a second nucleotide sequence when the first nucleotide sequence is in a functional relationship with the second nucleotide sequence. For instance, a promoter is operably linked to a coding sequence if the promoter affects the transcription or expression of the coding sequence. When recombinantly produced, operably linked nucleotide sequences are generally contiguous and, where necessary to join two protein-coding regions, in the same reading frame. However, nucleotide sequences need not be contiguous to be operably linked.

The term, "operably linked," when used in reference to a gene regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Conventional regulatory sequences may include 5' untranslated regions; promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule. Elements that may be "operably linked" to a coding sequence are not limited to promoters or other conventional regulatory sequences. For example, in some embodiments, the DNA-binding domain of a transactivator protein may bind to a nucleotide sequence that is proximal to a promoter or other regulatory region, such that the transactivator protein may interact with the promoter or other regulatory region, or a molecule bound thereto (e.g., a transcription factor) to affect transcription. In such examples, the nucleotide sequence to which the transactivator protein binds through its DNA-binding domain is "operably linked" to the coding sequence under the control of the promoter or other regulatory sequence.

Operatively linked polypeptides: As used herein with regard to polypeptides, the term "operatively linked" refers to at least two polypeptides that are connected in a single molecule (e.g., a fusion protein), and in such a manner that each polypeptide can serve its intended function. Typically, the at least two polypeptides are covalently attached through peptide bonds. A fusion protein comprising operatively linked polypeptides may be produced by standard recombinant DNA techniques. For example, a DNA molecule encoding a first polypeptide may be ligated to another DNA molecule encoding a second polypeptide, and the resultant hybrid DNA molecule may be expressed in a host cell to produce a fusion protein comprising the first and second polypeptides. In particular examples, the two DNA molecules may be ligated to each other in a 5' to 3' orientation, such that, after ligation, the translational frame of the encoded polypeptides is not altered (i.e., the DNA molecules are ligated to each other in-frame).

Promoter: As used herein, the terra "promoter" refers to a region of DNA that may be upstream from the start of transcription, and that may be involved in recognition and binding of RNA polymerase and other proteins to effect transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in a plant cell.

Examples of promoters under developmental control include promoters that preferentially initiate transcription in certain tissues, for example and without limitation, leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily effects transcription in certain cell types in one or more organs, for example and without limitation, in vascular cells in roots or leaves. Exemplary tissue-specific or tissue-preferred promoters include, but are not limited to: A root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

An "inducible" promoter may be a promoter which may be under environmental control. See Ward et al. (1993) *Plant Mol. Biol.* 22:361-366. Examples of environmental conditions that may initiate transcription by inducible promoters include, for example and without limitation, anaerobic conditions and the presence of light. With an inducible promoter, the rate of transcription increases in response to an inducing agent. Exemplary inducible promoters include, but are not limited to: Promoters from the ACEI system that responds to copper; Int gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) *Proc. Natl. Acad. Sci. USA* 88:0421).

Tissue-specific, tissue-preferred, cell type specific, and inducible promoters constitute the class of "non-constitutive" promoters. A "constitutive" promoter is a promoter that may be active under most environmental conditions. Exemplary constitutive promoters include, but are not limited to: Promoters from plant viruses, such as the 35S promoter from CaMV; promoters from rice actin genes; ubiquitin promoters; pEMU; MAS; maize H3 histone promoter; and the ALS promoter, XbaI/NcoI fragment 5' to the *Brassica napus* ALS3 structural gene (or a nucleotide sequence similarity to said XbaI/NcoI fragment) (International PCT Publication No. WO 96/30530).

Any of the foregoing constitutive and non-constitutive promoters may be utilized in some embodiments of the invention. For example, a gene to be regulated by the activity of a synthetic transcriptional activator fusion protein may be provided (e.g., in a host cell), wherein the gene is operably linked to a promoter.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, for example, Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein with regard to nucleotide sequences, the term "substantially identical" may refer to sequences that are more than 85% identical. For example, a substantially identical nucleotide sequence may be at least 85.5%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Conservative substitution: As used herein, the term "conservative substitution" refers to a substitution where an amino acid residue is substituted for another amino acid in the same class. A non-conservative amino acid substitution is one where the residues do not fall into the same class, for example, substitution of a basic amino acid for a neutral or non-polar amino acid. Classes of amino acids that may be defined for the purpose of performing a conservative substitution are known in the art.

In some embodiments, a conservative substitution includes the substitution of a first aliphatic amino acid for a second, different aliphatic amino acid. For example, if a first amino acid is one of Gly; Ala; Pro; Ile; Leu; Val; and Met, the first amino acid may be replaced by a second, different amino acid selected from Gly; Ala; Pro; Ile; Leu; Val; and Met. In particular examples, if a first amino acid is one of Gly; Ala; Pro; Ile; Leu; and Val, the first amino acid may be replaced by a second, different amino acid selected from Gly; Ala; Pro; Ile; Leu; and Val. In particular examples involving the substitution of hydrophobic aliphatic amino acids, if a first amino acid is one of Ala; Pro; Ile; Leu; and Val, the first amino acid may be replaced by a second, different amino acid selected from Ala; Pro; Ile; Leu; and Val.

In some embodiments, a conservative substitution includes the substitution of a first aromatic amino acid for a second, different aromatic amino acid. For example, if a first amino acid is one of His; Phe; Trp; and Tyr, the first amino acid may be replaced by a second, different amino acid selected from His; Phe; Trp; and Tyr. In particular examples involving the substitution of uncharged aromatic amino acids, if a first amino acid is one of Phe; Trp; and Tyr, the first amino acid may be replaced by a second, different amino acid selected from Phe; Trp; and Tyr.

In some embodiments, a conservative substitution includes the substitution of a first hydrophobic amino acid for a second, different hydrophobic amino acid. For example, if a first amino acid is one of Ala; Val; Ile; Leu; Met; Phe; Tyr; and Trp, the first amino acid may be replaced by a second, different amino acid selected from Ala; Val; Ile; Leu; Met; Phe; Tyr; and Trp. In particular examples involving the substitution of non-aromatic, hydrophobic amino acids, if a first amino acid is one of Ala; Val; Ile; Leu; and Met, the first amino acid may be replaced by a second, different amino acid selected from Ala; Val; Ile; Leu; and Met.

In some embodiments, a conservative substitution includes the substitution of a first polar amino acid for a second, different polar amino acid. For example, if a first amino acid is one of Ser; Thr; Asn; Gln; Cys; Gly; Pro; Arg; His; Lys; Asp; and Glu, the first amino acid may be replaced by a second, different amino acid selected from Ser; Thr; Asn; Gln; Cys; Gly; Pro; Arg; His; Lys; Asp; and Glu. In particular examples involving the substitution of uncharged, polar amino acids, if a first amino acid is one of Ser; Thr; Asn; Gln; Cys; Gly; and Pro, the first amino acid may be replaced by a second, different amino acid selected from Ser; Thr; Asn; Gln; Cys; Gly; and Pro. In particular examples involving the substitution of charged, polar amino acids, if a first amino acid is one of His; Arg; Lys; Asp; and Glu, the first amino acid may be replaced by a second, different amino acid selected from His; Arg; Lys; Asp; and Glu. In further examples involving the substitution of charged, polar amino acids, if a first amino acid is one of Arg; Lys; Asp; and Glu, the first amino acid may be replaced by a second, different amino acid selected from Arg; Lys; Asp; and Glu. In particular examples involving the substitution of positively charged (basic), polar amino acids, if a first amino acid is one of His; Arg; and Lys, the first amino acid may be replaced by a second, different amino acid selected from His; Arg; and Lys. In further examples involving the substitution of positively charged, polar amino acids, if a first amino acid is Arg or Lys, the first amino acid may be replaced by the other amino acid of Arg and Lys. In particular examples involving the substitution of negatively charged (acidic), polar amino acids, if a first amino acid is Asp or Glu, the first amino acid may be replaced by the other amino acid of Asp and Glu. In particular examples involving the substitution of polar amino acids other than positively charged polar amino acids, if a first amino acid is one of Ser; Thr; Asn; Gln; Cys; Gly; Pro; Asp; and Glu, the first amino acid may be replaced by a second, different amino acid selected from Ser; Thr; Asn; Gln; Cys; Gly; Pro; Asp; and Glu. In particular examples involving the substitution of polar amino acids other than negatively charged polar amino acids, if a first amino acid is one of Ser; Thr; Asn; Gln; Cys; Gly; Pro; Arg; His; and Lys, the first amino acid may be replaced by a second, different amino acid selected from Ser; Thr; Asn; Gln; Cys; Gly; Pro; Arg; His; and Lys.

In some embodiments, a conservative substitution includes the substitution of a first electrically neutral amino acid for a second, different electrically neutral amino acid. For example, if a first amino acid is one of Gly; Ser; Thr; Cys; Asn; Gln; and Tyr, the first amino acid may be replaced by a second, different amino acid selected from Gly; Ser; Thr; Cys; Asn; Gln; and Tyr.

In some embodiments, a conservative substitution includes the substitution of a first non-polar amino acid for a second, different non-polar amino acid. For example, if a first amino acid is one of Ala; Val; Leu; Ile; Phe; Trp; Pro; and Met, the first amino acid may be replaced by a second, different amino acid selected from Ala; Val; Leu; Ile; Phe; Trp; Pro; and Met.

In many examples, the selection of a particular second amino acid to be used in a conservative substitution to replace a first amino acid may be made in order to maximize the number of the foregoing classes to which the first and second amino acids both belong. Thus, if the first amino acid is Ser (a polar, non-aromatic, and electrically neutral amino acid), the second amino acid may be another polar amino acid (i.e., Thr; Asn; Gln; Cys; Gly; Pro; Arg; His; Lys; Asp; or Glu); another non-aromatic amino acid (i.e., Thr; Asn; Gln; Cys; Gly; Pro; Arg; His; Lys; Asp; Glu; Ala; Ile; Leu; Val; or Met); or another electrically-neutral amino acid (i.e., Gly; Thr; Cys; Asn; Gln; or Tyr). However, it may be preferred that the second amino acid in this case be one of Thr; Asn; Gln; Cys; and Gly, because these amino acids share all the classifications according to polarity, non-aromaticity, and electrical neutrality. Additional criteria that may optionally be used to select a particular second amino acid to be used in a conservative substitution are known in the art. For example, when Thr; Asn; Gln; Cys; and Gly are available to be used in a conservative substitution for Ser, Cys may be eliminated from selection in order to avoid the formation of undesirable cross-linkages and/or disulfide bonds. Likewise, Gly may be eliminated from selection, because it lacks an alkyl side chain. In this case, Thr may be selected, e.g., in order to retain the functionality of a side chain hydroxyl group. The selection of the particular second amino acid to be used in a conservative substitution is ultimately, however, within the discretion of the skilled practitioner.

The term "derivative" as used herein in relation to the amino acid sequence means chemical modification of a fusion protein of the invention.

Transactivating protein: As used herein, the term "transactivating protein" (or "transactivator" or "transcriptional activator protein" or "transcriptional activator fusion protein") refers to a polypeptide that binds to a nucleic acid element and initiates or enhances the transcription of a polynucleotide (e.g., a gene of interest) that is operably linked to the nucleic acid element. Transactivating proteins that are native to certain organisms include, for example and without limitation, zinc finger DNA-binding proteins; UPA DNA-binding domain; GAL4; and TAL. Particular embodiments of the invention include synthetic fusion protein transactivators comprising at least one DNA-binding domain from a DNA-binding protein and an interaction motif from a plant transactivation domain.

Specific binding: As used herein with regard to polypeptides and protein domains, the term "specific binding" refers to a sufficiently strong interaction between the polypeptide or protein domain and its binding partner(s) (e.g., polypeptide(s) comprising a specific amino acid sequence, or nucleic acid(s) comprising a specific nucleotide sequence) such that stable and specific binding occurs with the binding partner(s), but not with other molecules that lack a specific amino acid sequence or specific nucleotide sequence that is recognized by the specifically-binding polypeptide. Stable and specific binding may be ascertained by techniques routine to those in the art; such as "pulldown" assays (e.g., GST pulldowns), yeast-2-hybrid assays, yeast-3-hybrid assays, ELISA, etc. Molecules that have the attribute of "specific binding" to each other may be said to "bind specifically" to each other.

Transformation: As used herein, the term "transformation" refers to the transfer of one or more nucleic acid molecule(s) into a cell. A cell is "transformed" by a nucleic acid molecule transferred into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) *Nature* 319:791-3); lipofection (Felgner et al. (1987) *Proc. Natl. Acad. Sci. USA* 84:7413-7); microinjection (Mueller et al. (1978) *Cell* 15:579-85); *Agrobacterium*-mediated transfer (Fraley et al. (1983) *Proc. Natl. Acad. Sci. USA* 80:4803-7); direct DNA uptake; and microprojectile bombardment (Klein et al. (1987) *Nature* 327:70).

Transgene: An exogenous nucleic acid sequence. In some examples, a transgene may be a sequence that encodes a polypeptide comprising at least one synthetic transcriptional activator fusion protein. In some examples, a transgene may encode a synthetic transcriptional activator fusion protein comprising at least one plant TAD and/or at least one variant TAD. In some examples, a transgene may encode a gene of interest (e.g., a reporter gene; a gene conferring herbicide resistance; and a gene contributing to an agriculturally important plant trait). In these and other examples, a transgene may contain one or more regulatory sequences (e.g., a promoter) operably linked to a coding sequence of the transgene. For the purposes of this disclosure, the term "transgenic," when used to refer to an organism (e.g., a plant), refers to an organism that comprises the exogenous nucleic acid sequence. In some examples, the organism comprising the exogenous nucleic acid sequence may be an organism into which the nucleic acid sequence was introduced via molecular transformation techniques. In other examples, the organism comprising the exogenous nucleic acid sequence may be an organism into which the nucleic acid sequence was introduced by, for example, introgression or cross-pollination in a plant.

Vector: As used herein, the term "vector" refers to a nucleic acid molecule as may be introduced into a cell, for example, to produce a transformed cell. A vector may include nucleic acid sequences that permit it to replicate in a host cell, such as an origin of replication. Examples of vectors include, but are not limited to: plasmids; cosmids; bacteriophages; and viruses that carry exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Unless specifically indicated or implied, the terms "a", "an", and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8).

IV. Interaction Motifs from Plant Transactivation Domains

This disclosure provides novel plant TADs and protein-protein interaction motifs therefrom, as well as nucleic acids encoding the same. TADs that were identified and isolated from the plant proteins, ERF2 (*Arabidopsis thaliana*); PTI4 (*Solanum tuberosum*); AtERF1 (*A. thaliana*); ORCA2 (*Catharanthus roseus*); DREB1A (*A. thaliana*); CBF1 (*A. thaliana*); and DOF1 (*Zea mays*), were used to identify plant TAD interaction motifs that may in some embodiments be "swapped" into a heterologous TAD, or used to produce a variant TAD interaction motif. The newly identified plant TADs, interaction motifs therein, and variant TADs thereof, may be used in particular embodiments (e.g., by inclusion in a synthetic transcriptional activator protein) to confer new and desirable expression regulatory control to a gene of interest.

The TAD of VP16 (V16 TAD) has been characterized, and structural regions of the foregoing novel plant TADs and interaction domains are referred to by analogy to the corresponding structures in VP16 TAD. VP16 TAD can be divided into two subdomains, and each subdomain is capable of independently and autonomously activating transcription when tethered to a DNA-binding domain. The VP16 subdomains are sometimes referred to as the amino subdomain (or "VP16 transactivation subdomain I" or "VP16$_{412\text{-}456}$") and the carboxyl subdomain (or "VP16 transactivation subdomain II" or "VP16$_{456\text{-}490}$") VP16 interacts through its interaction domains with several target proteins involved in transcription, including the p62/Tfb1 subunit of transcription factor IIB (TFIIB).

The activity of VP16 depends not only on acidic residues, but also on hydrophobic and aromatic amino acids within the TAD. See, e.g., Cress and Triezenberg (1991) *Science* 251(4989):87-90. However, the acidic VP16 TAD may be more tolerant to mutagenesis than many other polypeptide sequences, due to the lack of regular secondary structure in acidic TADs. Sigler (1988) *Nature* 333:210-2. The unstructured nature of the VP16 TAD subdomains may help the TAD mediate multiple protein/protein interactions with different binding partners (Dyson and Wright (2002) *Curr. Opin. Struct. Biol.* 12(1):54-60), and the TAD subdomains may adopt a more ordered structure (e.g., a short α-helix (Langlois et al. (2008), supra) when they are bound to target proteins than when free in solution. See, e.g., Garza et al. (2009) *Life Sci.* 84(7-8):189-93; Jonker et al. (2005) *Biochemistry* 44(3):827-39; Langlois et al. (2008), supra.

Some embodiments include a synthetic transcriptional activator protein comprising a plant TAD interaction motif, wherein the plant TAD interaction motif is selected from the group consisting of SEQ ID NOs:10-16. Some exemplary synthetic transcriptional activator proteins comprise a TAD that comprises a plant TAD interaction motif, and such proteins may have a sequence including, for example and without limitation, SEQ ID NOs:2-8 and SEQ ID NOs:100-106. Additional exemplary TADs comprising a plant TAD interaction motif include those engineered by replacing a native TAD interaction motif sequence comprised in a native transactivator TAD with one of SEQ ID NOs:10-16.

Some embodiments of the invention take advantage of the surprising discovery that variant TAD interaction motifs, comprising conservative amino acid substitutions and/or substitutions with amino acids found in the analogous position in a homologous interaction motif (e.g., from an ortholog of the native protein comprising the reference TAD interaction motif), may yield new and particular gene regulatory properties. These particular properties may be desirable for the expression of a polynucleotide, wherein a certain level of expression is desired. For example, a variant TAD interaction motif may provide enhanced expression over a native reference TAD motif that itself enhances expression, and thus may be desirable in protein synthesis and purification reactions, where maximized expression is often a goal. In other examples, a variant TAD interaction motif may provide less expression than a native reference TAD motif where less than maximized expression is desired.

Thus, some embodiments include a synthetic transcriptional activator protein comprising a variant TAD interaction motif. In some examples, a variant TAD interaction motif may be a variant of one of SEQ ID NOs:10-16. Variant TAD interaction motifs include polypeptides having the amino acid sequence of a native TAD interaction sequence, but wherein one or more amino acids in the sequence have been changed to the amino acid found at the corresponding position in a different, homologous TAD. Variant TAD interaction motifs also include polypeptides having the amino acid sequence of a native TAD interaction sequence, but wherein a conservative substitution has been made for one or more amino acids in the sequence. A variant TAD interaction motif may be, for example and without limitation, at least 95% identical to a reference TAD interaction motif sequence (e.g., a sequence selected from SEQ ID NOs:10-16); at least 90% identical to the reference sequence; at least 85% identical to the reference sequence; at least 80% identical to the reference sequence; at least 75% identical to the reference sequence; at least 70% identical to the reference sequence; at least 65% identical to the reference sequence; at least 60% identical to the reference sequence; at least 55% identical to the reference sequence; at least 50% identical to the reference sequence; or less than 50% identical to the reference sequence.

Variant TAD interaction motifs include, for example and without limitation, SEQ ID NOs:17-22 (exemplary variant ERF2 TAD interaction motifs); SEQ ID NOs:23-28 (exemplary variant PTI4 TAD interaction motifs); SEQ ID NOs:29-34 (exemplary variant AtERF1 TAD interaction motifs); SEQ ID NOs:35-40 (exemplary variant ORCA2 TAD interaction motifs); SEQ ID NOs:41-46 (exemplary variant DREB1A TAD interaction motifs); SEQ ID NOs:47-52 (exemplary variant CBF1 TAD interaction motifs); and SEQ ID NOs:53-58 (exemplary variant DOF1 TAD interaction motifs). Exemplary TADs comprising a variant TAD interaction motif include those engineered by replacing a TAD interaction motif sequence comprised in a native transactivator TAD with a variant TAD selected from the group consisting of SEQ ID NOs:17-58. For example, exemplary TADs comprising a variant TAD interaction motif include SEQ ID NOs: 107-120.

Nucleic acids encoding any and all of the foregoing polypeptides are immediately identifiable from the amino acid sequence of the polypeptide. For example, a TAD or TAD interaction motif may be encoded by the native polynucleotide that is transcribed to generate an mRNA that is subsequently translated into the amino acids of the TAD or TAD interaction motif. However, one of skill in the art will appreciate that, due to the degeneracy of the genetic code, many other equivalent polynucleotides exist that will encode an identical polypeptide. Variant TAD interaction motifs (e.g., SEQ ID NOs:17-58) may be encoded by polynucleotides that are readily determinable by reference to an RNA codon table from the amino acid sequence of the particular variant desired. In particular embodiments, it may be desirable for the nucleotide sequence of a polynucleotide encoding a TAD interaction motif (or variant thereof) to be assembled according to the codon usage of the host cell, for example, so as to maximize or optimize expression of a protein (e.g., a fusion protein) comprising the TAD interaction motif.

V. Fusion Protein Transcriptional Activators

This disclosure also provides synthetic transcriptional activator fusion proteins comprising a plant TAD interaction motif and/or a variant TAD interaction motif. In some embodiments, a synthetic transcriptional activator fusion protein further comprises at least one DNA-binding domain. Nucleic acids (e.g., DNA) encoding such synthetic transcriptional activator fusion proteins are also provided.

In some embodiments, a synthetic transcriptional activator fusion protein comprises at least a first polypeptide that binds to DNA in a sequence-specific manner (i.e., a "DNA-binding domain"). The first DNA-binding domain polypeptide of the synthetic transcriptional activator fusion protein may be operatively linked to at least a second polypeptide comprising a plant TAD interaction motif or variant TAD interaction motif. In some examples, a synthetic transcriptional activator fusion protein may comprise additional polypeptides, such as a spacer sequence positioned between the first and second polypeptides in the fusion protein; a leader peptide; a peptide that targets the fusion protein to an organelle (e.g., the nucleus); polypeptides that are cleaved by a cellular enzyme; peptide tags; and other amino acid sequences that do not interfere with the function of the operatively linked first and second polypeptides.

In some embodiments, the first and second polypeptides of a synthetic transcriptional activator fusion protein may be operatively linked by their expression from a single polynucleotide encoding the first and second polypeptides ligated to each other in-frame, so as to create a chimeric gene encoding a fusion protein. Examples of polynucleotides encoding a transcriptional activator fusion protein comprising a DNA-binding domain and a TAD interaction motif include, without limitation, SEQ ID NOs: 79-93. In alternative embodiments, the first and second polypeptides of a synthetic transcriptional activator fusion protein may be operatively linked by other means, such as by cross-linkage of independently expressed first and second polypeptides.

Plant TAD interaction motifs and variant TAD interaction motifs that may be comprised within a synthetic transcriptional activator fusion protein include the TAD interaction motifs and variants thereof described in Section IV, supra. For example, a synthetic transcriptional activator fusion protein may comprise a polypeptide selected from the group consisting of SEQ ID NOs:10-58.

DNA-binding domains that may be comprised in a synthetic transcriptional activator fusion protein include zinc finger DNA-binding domains from zinc finger proteins (e.g., a Z6 DNA-binding domain). Individual zinc finger DNA-binding domains can be designed to target and bind to a large range of DNA sites. See, e.g., Wu et al. (2007) *Cell. Mol. Life Sci.* 64:2933-44. Canonical $Cys_2His_2$, as well as non-canonical $Cys_3His$ zinc finger proteins, bind DNA by inserting an α-helix into the major groove of the double helix. Recognition of DNA by zinc finger domains is modular; each finger contacts primarily three consecutive base pairs in the target, and a few key residues in the protein mediate recognition. By including multiple zinc finger DNA-binding domains in a synthetic transcriptional activator fusion protein, the DNA-binding specificity of the fusion protein may be further increased (and hence the specificity of any gene regulatory effects conferred thereby may also be increased). See, e.g., Urnov et al. (2005) *Nature* 435:646-51. Thus, one or more zinc finger DNA-binding domains may be engineered and utilized such that a synthetic transcriptional activator fusion protein introduced into a host cell interacts with a DNA sequence that is unique within the genome of the host cell.

In some examples, a synthetic transcriptional activator fusion protein comprises a DNA-binding domain from GAL4, a modular transactivator in *Saccharomyces cerevisiae*, but which also operates as a transactivator in many other organisms. See, e.g., Sadowski et al. (1988) *Nature* 335:563-4. In this regulatory system, the expression of genes encoding enzymes of the galactose metabolic pathway in *S. cerevisiae* is stringently regulated by the available carbon source. Johnston (1987) *Microbiol. Rev.* 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 consists of 881 amino acid residues, with a molecular weight of 99 kDa. GAL4 comprises functionally autonomous domains, the combined activities of which account for activity of GAL4 in vivo. Ma & Ptashne (1987) *Cell* 48:847-53); Brent & Ptashne (1985) *Cell* 43(3 Pt 2):729-36. The N-terminal 65 amino acids of GAL4 comprise the GAL4 DNA-binding domain. Keegan et al. (1986) *Science* 231:699-704; Johnston (1987) *Nature* 328:353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) *Nature* 356:408-14. The DNA-binding function of the protein positions C-terminal transcriptional activating domains in the vicinity of the promoter, such that the activating domains can direct transcription.

Additional DNA-binding domains that may be comprised in a synthetic transcriptional activator fusion protein include, for example and without limitation, a binding sequence from a AVRBS3-inducible gene; a consensus binding sequence from a AVRBS3-inducible gene or synthetic binding sequence engineered therefrom (e.g., UPA DNA-binding domain; SEQ ID NO:89); TAL; LexA (see, e.g., Brent & Ptashne (1985), supra); LacR (see, e.g., Labow et al. (1990) *Mol. Cell. Biol.* 10:3343-56; Baim et al. (1991) *Proc. Natl. Acad. Sci. USA* 88(12):5072-6); a steroid hormone receptor (Ellliston et al. (1990) *J. Biol. Chem.* 265: 11517-121); the Tet repressor (U.S. Pat. No. 6,271,341) and a mutated Tet repressor that binds to a tet operator sequence in the presence, but not the absence, of tetracycline (Tc); and components of the regulatory system described in Wang et al. (1994) *Proc. Natl. Acad. Sci. USA* 91(17):8180-4, which utilizes a fusion of GAL4, a hormone receptor, and VP16.

In some examples, a synthetic transcriptional activator fusion protein comprises more than one TAD interaction motif. For example and without limitation, a synthetic transcriptional activator fusion protein may comprise 2, 3, 4, or more TAD interaction domains. In some examples, a synthetic transcriptional activator fusion protein comprises more than one DNA-binding domain. For example and without limitation, a synthetic transcriptional activator fusion protein may comprise 2, 3, 4, 5, 6, 7, 8, 9, 10, or more DNA-binding domains.

VI. Nucleic Acid Molecules Comprising a Polynucleotide Encoding a Fusion Protein Transcriptional Activator In some embodiments, this disclosure provides a nucleic acid molecule comprising at least one polynucleotide sequence encoding a plant TAD interaction motif, variant TAD interaction motif, plant TAD, or variant TAD. Such nucleic acid molecules may further comprise at least one polynucleotide sequence encoding a DNA-binding domain. For example, a nucleic acid in some embodiments comprises a first polynucleotide sequence encoding a plant TAD interaction motif, variant TAD interaction motif, plant TAD, or variant TAD, fused in-frame to a second polynucleotide sequence encoding a DNA-binding domain, such that the two polynucleotide sequences are transcribed as part of a single fusion protein.

In nucleic acid molecules provided in some embodiments of the invention, the last codon of a first polynucleotide sequence encoding a plant TAD interaction motif, variant TAD interaction motif, plant TAD, or variant TAD, and the first codon of a second polynucleotide sequence encoding a DNA-binding domain may be separated by any number of nucleotide triplets, e.g., without coding for an intron or a "STOP." Likewise, the last codon of a nucleotide sequence encoding a first polynucleotide sequence encoding a DNA-binding domain, and the first codon of a second polynucleotide sequence encoding a plant TAD interaction motif, variant TAD interaction motif, plant TAD, or variant TAD, may be separated by any number of nucleotide triplets. In these and further embodiments, the last codon of the last (i.e., most 3' in the nucleic acid sequence) of the first polynucleotide sequence encoding a plant TAD interaction motif, variant TAD interaction motif, plant TAD, or variant TAD, and the second polynucleotide sequence encoding a DNA-binding domain, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating a polynucleotide sequence encoding a plant TAD interaction motif, variant TAD interaction motif, plant TAD, or variant TAD, and a polynucleotide sequence encoding a DNA-binding domain may, for example, consist of any sequence, such that the amino acid sequence encoded is not likely to significantly alter the translation of the fusion protein. Due to the autonomous nature of the TAD interaction domains (and variants thereof) disclosed herein and known DNA-binding domains, intervening sequences will not in examples interfere with the respective functions of these structures.

Some embodiments of the invention also include a nucleic acid molecule comprising a polynucleotide sequence encoding a plant TAD interaction motif, variant TAD interaction motif, plant TAD, or variant TAD, wherein the nucleic acid molecule does not comprise a polynucleotide sequence encoding a DNA-binding domain. Such nucleic acid molecules may be useful, for example, in facilitating manipulation of the TAD interaction motif-encoding sequence in molecular biology techniques. For example, in some embodiments, a TAD interaction motif-encoding sequence may be introduced into a suitable vector for sub-cloning of the sequence into an expression vector, or a TAD interaction motif-encoding sequence may be introduced into a nucleic acid molecule that facilitates the production of a further nucleic acid molecule comprising the TAD interaction motif-encoding sequence operably linked to a nucleotide sequence of interest.

All of the nucleotide sequences that encode, for example, a fusion protein comprising at least one particular plant TAD interaction motif, variant TAD interaction motif, plant TAD, or variant TAD, and further comprising at least one particular DNA-binding domain, will be immediately recognizable by those of skill in the art. The degeneracy of the genetic code provides a finite number of coding sequences for a particular amino acid sequence. The selection of a particular sequence to encode a fusion protein according to embodiments of the invention is within the discretion of the practitioner. Different coding sequences may be desirable in different applications.

In some embodiments, it may be desirable to modify the nucleotides of a polynucleotide sequence encoding a plant TAD interaction motif, variant TAD interaction motif, plant TAD, or variant TAD (and/or nucleotides of a DNA-binding domain-encoding sequence), for example, to enhance expression of the polynucleotide sequence in a particular host. The genetic code is redundant with 64 possible codons, but most organism preferentially use a subset of these codons. The codons that are utilized most often in a species are called optimal codons, and those not utilized very often are classified as rare or low-usage codons. Zhang et al. (1991) *Gene* 105:61-72. Codons may be substituted to reflect the preferred codon usage of a particular host in a process sometimes referred to as "codon optimization." Optimized coding sequences containing codons preferred by a particular prokaryotic or eukaryotic host may be prepared by, for example, to increase the rate of translation or to produce recombinant RNA transcripts having desirable properties (e.g., a longer half-life, as compared with transcripts produced from a non-optimized sequence).

VII. Expression of a Fusion Protein Transcriptional Activator

In some embodiments, at least one fusion protein-encoding nucleic acid molecule(s) comprising at least one polynucleotide sequence encoding a plant TAD interaction motif (or variant TAD interaction motif, plant TAD, or variant TAD), and at least one polynucleotide sequence encoding a DNA-binding domain, may be introduced into a cell, tissue, or organism for expression of the fusion protein therein.

In some embodiments, such a nucleic acid molecule may, for example, be a vector system including, for example and without limitation, a linear plasmid, and a closed circular plasmid. In particular examples, the vector may be an expression vector. Nucleic acid sequences according to particular embodiments may, for example, be inserted into a vector, such that the nucleic acid sequence is operably linked to one or more regulatory sequences. Many vectors are available for this purpose, and selection of the particular vector may depend, for example, on the size of the nucleic acid to be inserted into the vector, the particular host cell to be transformed with the vector, and/or the amount of the fusion protein that is desired to be expressed. A vector typically contains various components, the identity of which depend on a function of the vector (e.g., amplification of DNA and expression of DNA), and the particular host cell(s) with which the vector is compatible.

Some embodiments may include a plant transformation vector that comprises a nucleotide sequence comprising at least one regulatory sequence operably linked to one or more nucleotide sequence(s) encoding a fusion protein comprising at least one plant TAD interaction motif, variant TAD interaction motif, plant TAD, or variant TAD, operatively linked to at least one DNA-binding domain. The one or more nucleotide sequence(s) may be expressed, under the control of the regulatory sequence(s), in a plant cell, tissue, or organism to produce the fusion protein.

In some embodiments, a regulatory sequence operably linked to one or more nucleotide sequence(s) encoding a fusion protein comprising at least one plant TAD interaction motif, variant TAD interaction motif, plant TAD, or variant TAD, operatively linked to at least one DNA-binding domain, may be a promoter sequence that functions in a host cell, such as a bacterial cell, wherein the nucleic acid molecule is to be amplified, or a plant cell wherein the nucleic acid molecule is to be expressed.

Promoters suitable for use in nucleic acid molecules according to some embodiments include those that are inducible, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter).

Additional exemplary promoters include the nopaline synthase (NOS) promoter (Ebert et al. (1987) *Proc. Natl. Acad. Sci. USA* 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) *Plant Mol. Biol.* 9:315-24); the CaMV 35S promoter (Odell et al. (1985) *Nature* 313: 810-2; the figwort mosaic virus 35S-promoter (Walker et al. (1987) *Proc. Natl. Acad. Sci. USA* 84(19):6624-8); the sucrose synthase promoter (Yang and Russell (1990) *Proc. Natl. Acad. Sci. USA* 87:4144-8); the R gene complex promoter (Chandler et al. (1989) *Plant Cell* 1:1175-83); the chlorophyll a/b binding protein gene promoter; CaMV35S (U.S. Pat. Nos. 5,322,938, 5,352,605, 5,359,142, and 5,530, 196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) *J. Mol. Appl. Genet.* 1:561-73; Bevan et al. (1983) *Nature* 304:184-7).

In particular embodiments, nucleic acid molecules of the invention may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Application No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, a developmental stage-specific promoter (e.g., a promoter active at a later stage in development) may be used in a composition or method of the invention.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and *petunia* heat shock protein leaders (U.S. Pat. No. 5,362,865), plant virus coat protein leaders, plant rubisco leaders, and others. See, e.g., Turner and Foster (1995) *Molecular Biotech.* 3(3):225-36. Non-limiting examples of 5' UTRs are provided by: GmHsp (U.S. Pat. No. 5,659,122); PhDnaK (U.S. Pat. No. 5,362,865); AtAnt1; TEV (Carrington and Freed (1990) *J. Virol.* 64:1590-7); and AGRtunos (GenBank Accession No. V00087; and Bevan et al. (1983), supra).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) *Proc. Natl. Acad. Sci. USA* 80:4803-7). An example of the use of different 3' nontranslated regions is provided in Ingelbrecht et al. (1989) *Plant Cell* 1:671-80. Non-limiting examples of polyadenylation signals include one from a *Pisum sativum* RbcS2 gene (Ps.RbcS2-E9; Coruzzi et al. (1984) *EMBO J.* 3:1671-9) and AGRtu.nos (GenBank Accession No. E01312).

Additional information regarding regulatory sequences that may be useful in particular embodiments is described, for example, in Goeddel (1990) "Gene Expression Technology," *Methods Enzymol.* 185, Academic Press, San Diego, Calif.

A recombinant nucleic acid molecule or vector of the present invention may comprise a selectable marker that confers a selectable phenotype on a transformed cell, such as a plant cell. Selectable markers may also be used to select for plants or plant cells that comprise a nucleic acid molecule of the invention. The marker may encode biocide resistance, antibiotic resistance (e.g., kanamycin, Geneticin (G418), bleomycin, and hygromycin), or herbicide resistance (e.g., glyphosate). Examples of selectable markers include, but are not limited to: a neo gene that confers kanamycin resistance and can be selected for using, e.g., kanamycin and G418; a bar gene that confers bialaphos resistance; a mutant EPSP synthase gene that confers glyphosate resistance; a nitrilase gene that confers resistance to bromoxynil; a mutant acetolactate synthase gene (ALS) that confers imidazolinone or sulfonylurea resistance; and a methotrexate-resistant DHFR gene. Multiple selectable markers are available that confer resistance to chemical agents including, for example and without limitation, ampicillin; bleomycin; chloramphenicol; gentamycin; hygromycin; kanamycin; lincomycin; methotrexate; phosphinothricin; puromycin; spectinomycin; rifampicin; streptomycin; and tetracycline. Examples of such selectable markers are illustrated in, e.g., U.S. Pat. Nos. 5,550,318; 5,633,435; 5,780,708 and 6,118,047.

A nucleic acid molecule or vector of the present invention may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) *Plant Mol. Biol. Rep.* 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18*th Stadler Genetics Symposium*, P. Gustafson and R. Appels, eds., Plenum, NY (pp. 263-82); a β-lactamase gene (Sutcliffe et al. (1978) *Proc. Natl. Acad. Sci. USA* 75:3737-41); a gene which encodes an enzyme for which various chromogenic substrates are known (e.g., PADAC, a chromogenic cephalosporin); a luciferase gene (Ow et al. (1986) *Science* 234:856-9); a xylE gene that encodes a catechol dioxygenase that converts chromogenic catechols (Zukowski et al. (1983) *Gene* 46(2-3):247-55); an amylase gene (Ikatu et al. (1990) *Bio/Technol.* 8:241-2); a tyrosinase gene which encodes an enzyme capable of oxidizing tyrosine to DOPA and dopaquinone, which in turn condenses to melanin (Katz et al. (1983) *J. Gen. Microbiol.* 129:2703-14); and an α-galactosidase.

Suitable methods for transformation of host cells include any method by which DNA can be introduced into a cell, for example and without limitation: by transformation of protoplasts (See, e.g., U.S. Pat. No. 5,508,184); by desiccation/ inhibition-mediated DNA uptake (See, e.g., Potrykus et al. (1985) *Mol. Gen. Genet.* 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); and by acceleration of DNA-coated particles (See, e.g., U.S. Pat. Nos. 5,015, 580, 5,550,318, 5,538,880, 6,160,208, 6,399,861, and 6,403, 865). Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely utilized method for introducing an expression vector into plants is based on the natural transformation system of *Agrobacterium*. *A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of *A. tumefaciens* (See, e.g., U.S. Pat. Nos. 4,536,475, 4,693,977, 4,886,937, and 5,501, 967; and European Patent EP 0 122 791) or a $R_i$ plasmid of *A. rhizogenes*. Additional plant transformation vectors include, for example and without limitation, those described by Herrera-Estrella et al. (1983) *Nature* 303:209-13; Bevan et al. (1983), supra; Klee et al. (1985) *Bio/Technol.* 3:637- 42; and in European Patent EP 0 120 516, and those derived from any of the foregoing. Other bacteria, such as *Sinorhizobium, Rhizobium*, and *Mesorhizobium*, that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one fusion protein of the invention) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers that are specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et al. (2002) *Plant J.* 32:243-53), and may be applied to genomic DNA derived from any plant species or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay).

In particular embodiments, copies of at least one synthetic transcriptional activator fusion protein comprising at least one plant TAD interaction motif (and/or variant TAD interaction motif) and at least one DNA-binding domain are produced in a cell, into which has been introduced at least one nucleic acid molecule(s) comprising a nucleotide sequence encoding the at least one synthetic transcriptional activator fusion protein. Each synthetic transcriptional activator fusion protein may be expressed from multiple nucleic acid sequences introduced in different transformation events, or from a single nucleic acid sequence introduced in a single transformation event. In some embodiments, a plurality of such fusion proteins may be expressed under the control of a single promoter. In other embodiments, a plurality of such fusion proteins may be expressed under the control of multiple promoters.

In addition to direct transformation of a plant or plant cell with a nucleic acid molecule of the invention, transgenic plants may be prepared in some embodiments by crossing a first plant having at least one transgenic event with a second plant lacking such an event. For example, a nucleic acid molecule comprising a nucleotide sequence encoding a synthetic transcriptional activator fusion protein comprising at least one plant TAD interaction motif (and/or variant TAD interaction motif) and at least one DNA-binding domain may be introduced into a first plant line that is amenable to transformation, to produce a transgenic plant, which transgenic plant may be crossed with a second plant line to introgress the nucleotide sequence that encodes the synthetic transcriptional activator fusion protein into the second plant line.

VIII. Plant Materials Comprising a Fusion Protein Transcriptional Activator

In some embodiments, a plant is provided, wherein the plant comprises a plant cell comprising a nucleotide sequence encoding a synthetic transcriptional activator fusion protein comprising at least one plant TAD interaction motif (and/or variant TAD interaction motif) and at least one DNA-binding domain. In particular embodiments, such a plant may be produced by transformation of a plant tissue or plant cell, and regeneration of a whole plant. In further embodiments, such a plant may be obtained through introgression of a nucleic acid comprising a nucleotide sequence encoding a synthetic transcriptional activator fusion protein into a germplasm. Plant materials comprising such a plant cell are also provided. Such a plant material may be obtained from a plant comprising the plant cell.

A transgenic plant or plant material comprising a nucleotide sequence encoding a synthetic transcriptional activator fusion protein comprising at least one plant TAD interaction motif (and/or variant TAD interaction motif) and at least one DNA-binding domain may in some embodiments exhibit one or more of the following characteristics: expression of the fusion protein in a cell of the plant; expression of the fusion protein in a plastid of a cell of the plant; expression of the fusion protein in the nucleus of a cell of the plant; localization of the fusion protein in a cell of the plant; integration of the nucleotide sequence in the genome of a cell of the plant; presence of the nucleotide sequence in extra-chromosomal DNA of a cell of the plant; and/or the presence of an RNA transcript corresponding to the nucleotide sequence in a cell of the plant. Such a plant may additionally have one or more desirable traits other than expression of the encoded fusion protein. Such traits may include those resulting from the expression of an endogenous or transgenic nucleotide sequence, the expression of which is regulated by the fusion protein in a cell of the plant, for example and without limitation: resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid molecule of the invention. Accordingly, the plant may be a dicot or monocot. Non-limiting examples of dicotyledonous plants usable in the present methods include *Arabidopsis*, alfalfa, beans, broccoli, cabbage, canola, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, onion, rice, sorghum, wheat, rye, millet, sugarcane, oat, triticale, switchgrass, and turfgrass. Transgenic plants according to the invention may be used or cultivated in any manner.

Some embodiments also provide commodity products containing one or more nucleotide sequences encoding a synthetic transcriptional activator fusion protein comprising at least one plant TAD interaction motif (and/or variant TAD interaction motif) and at least one DNA-binding domain; for example, a commodity product produced from a recombinant plant or seed containing one or more of such nucleotide sequences. Commodity products containing one or more nucleotide sequences encoding a synthetic transcriptional activator fusion protein comprising at least one plant TAD interaction motif (and/or variant TAD interaction motif) and at least one DNA-binding domain include, for example and without limitation: food products, meals, oils, or crushed or whole grains or seeds of a plant comprising one or more nucleotide sequences encoding such a synthetic transcriptional activator fusion protein. The detection of one or more nucleotide sequences encoding a synthetic transcriptional activator fusion protein of the invention in one or more commodity or commodity products is de facto evidence that the commodity or commodity product was at least in part produced from a plant comprising one or more nucleotide sequences encoding a synthetic transcriptional activator fusion protein of the invention. In particular embodiments, a commodity product of the invention comprise a detectable amount of a nucleic acid sequence encoding a synthetic transcriptional activator fusion protein comprising at least one plant TAD interaction motif (and/or variant TAD interaction motif) and at least one DNA-binding domain. In some embodiments, such commodity products may be produced, for example, by obtaining transgenic plants and preparing food or feed from them.

In some embodiments, a transgenic plant or seed comprising a transgene comprising a nucleotide sequence encoding a synthetic transcriptional activator fusion protein of the invention also may comprise at least one other transgenic event in its genome, including without limitation: a transgenic event from which is transcribed an RNAi molecule; a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

In some embodiments, a transgenic plant or seed comprising a transgene comprising a nucleotide sequence encoding a synthetic transcriptional activator fusion protein of the invention may comprise an endogenous or native gene target within the genome of the transgenic plant, including without limitation: an endogenous gene target for an altered fatty acid metabolism trait, an endogenous gene target for a drought tolerance trait, an endogenous gene target for a nitrogen use efficiency trait, or any other endogenous gene target contributing to a desirable phenotype in the transgenic plant (e.g., increased yield, or restoration of cytoplasmic male sterility). The endogenous or native gene target may be operably linked to a nucleotide sequence to which the synthetic transcriptional activator fusion protein binds specifically, thereby affecting transcription of the target gene.

IX. Regulation of Expression by a Fusion Protein Transcriptional Activator

In some embodiments, a synthetic transcriptional activator fusion protein comprising at least one plant TAD interaction motif (and/or variant TAD interaction motif) and at least one DNA-binding domain may be used to increase (e.g., initiate) expression of a nucleotide sequence of interest (e.g., a gene of interest) in a cell. The nucleotide sequence of interest may in some embodiments be endogenous to the genome of the cell. In other embodiments, at least one exogenous nucleic acid molecule(s) comprising the nucleotide sequence of interest has been introduced into the cell. Generally, a second nucleotide sequence operably linked to the nucleotide sequence of interest will be recognized by the DNA-binding domain of the fusion protein, such that stable and specific binding between the second nucleotide sequence and the fusion protein can occur. In some examples, the at least one nucleic acid molecule(s) comprising the nucleotide sequence of interest further comprise such a second nucleotide sequence. In some examples, the at least one nucleic acid molecule(s) comprising the nucleotide sequence of interest are introduced into the host cell, such that the nucleotide sequence of interest is operably linked to a second nucleotide sequence that is endogenous to the host cell. For example, a nucleic acid molecule comprising the nucleotide sequence of interest may facilitate homologous recombination that inserts the nucleotide sequence of interest into the host cell's genome, such that the nucleotide sequence of interest is operably linked to an endogenous sequence that is recognized by a DNA-binding domain. In some examples, the at least one nucleic acid molecule(s) comprising the nucleotide sequence of interest is endogenous or native within the host cell, such that the nucleotide sequence of interest is operably linked to a second nucleotide sequence that is endogenous to the host cell.

Multiple nucleotide sequence(s) of interest that are introduced in different transformation events may be expressed under the regulatory control of a single fusion protein in some examples. In other examples, a single nucleotide sequence of interest (e.g., a single integration event) is regulated and expressed. In some embodiments, a plurality of nucleotide sequences of interest may be regulated by the binding of a fusion protein of the invention to a single nucleic acid binding site; for example, the plurality of nucleotide sequences of interest may all be operably linked to the same second nucleotide sequence to which the DNA-binding domain of the fusion protein specifically binds. The nucleotide sequences of interest comprising such a plurality are not necessarily the same in certain examples. Thus, multiple different gene products may be expressed under the regulatory control of a single fusion protein.

In particular embodiments, the expression product of a nucleotide sequence of interest that is under the regulatory control of a fusion protein of the invention may be a marker gene product; for example and without limitation, a fluorescent molecule. Quantitative and qualitative observations regarding the expression of such an expression product may provide a system to evaluate the particular regulatory properties of a particular TAD interaction motif or TAD interaction motif variant.

Any expression product (e.g., protein, precursor protein, and inhibitory RNA molecule) may be expressed under the regulatory control of a synthetic transcriptional activator fusion protein comprising at least one plant TAD interaction motif (and/or variant TAD interaction motif) and at least one DNA-binding domain. In particular examples, an expression product under the regulatory control of a synthetic transcriptional activator fusion protein may be, without limitation, an endogenous or native polypeptide that is normally expressed in the host cell into which a nucleic acid encoding the fusion protein is introduced. In other examples, an expression product under the regulatory control of a synthetic transcriptional activator fusion protein may be a heterologous polypeptide that is not normally expressed in the host cell. For example and without limitation, an expression product under the regulatory control of a synthetic transcriptional activator fusion protein may be a polypeptide involved in herbicide resistance, virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. An expression product under the regulatory control of a synthetic transcriptional activator fusion protein may alternatively be, for example and without limitation, a polypeptide involved in plant vigor or yield (including polypeptides involved in tolerance for extreme temperatures, soil conditions, light levels, water levels, and chemical environment), or a polypeptide that may be used as a marker to identify a plant comprising a trait of interest (e.g., a selectable marker gene product, and a polypeptide involved in seed color).

Non-limiting examples of polypeptides that may be under the regulatory control of a synthetic transcriptional activator fusion protein comprising at least one plant TAD interaction motif (and/or variant TAD interaction motif) and at least one DNA-binding domain in some embodiments of the invention include: acetolactase synthase (ALS), mutated ALS, and precursors of ALS (see, e.g., U.S. Pat. No. 5,013,659); EPSPS (see, e.g., U.S. Pat. Nos. 4,971,908 and 6,225,114), such as a CP4 EPSPS or a class III EPSPS; enzymes that modify a physiological process that occurs in a plastid, including for example and without limitation, photosynthesis, and synthesis of fatty acids, amino acids, oils, arotenoids, terpenoids, and starch. Other non-limiting examples of polypeptides that may be under the regulatory control of a synthetic transcriptional activator fusion protein in particular embodiments include: zeaxanthin epoxidase, choline monooxygenase, ferrochelatase, omega-3 fatty acid desaturase, glutamine synthetase, starch modifying enzymes, polypeptides involved in synthesis of essential amino acids, provitamin A, hormones, Bt toxin, and proteins. Nucleotide sequences encoding the aforementioned peptides are available in the art, and such nucleotide sequences may be operably linked to a specific binding site for a DNA-binding domain to be expressed under the regulatory control of a synthetic transcriptional activator fusion protein comprising at least one plant TAD interaction motif (and/or variant TAD interaction motif) and at least one DNA-binding domain that specifically binds to the operably linked site.

Furthermore, a variant nucleotide sequence of interest encoding any of the aforementioned polypeptides to be placed under regulatory control may be identified by those of skill in the art (for example, by cloning of genes with high homology to other genes encoding the particular polypeptide, or by in silico sequence generation in view of DNA codon degeneracy). Such variants may be desirable in particular embodiments, for example, to conform to the preferred codon usage of a host organism. Once such a variant nucleotide sequence of interest has been identified, a nucleic acid molecule to provide regulatory control of the sequence by a synthetic transcriptional activator polypeptide according to the invention may be designed, for example by operably linking the variant nucleotide sequence of interest in the nucleic acid molecule to a known binding site for the DNA-binding domain comprised within the particular synthetic transcriptional activator fusion protein to be used. In embodiments described herein, a surprising increase in the expression of such a variant nucleotide sequence of interest may be observed (e.g., in a host plant cell) when the nucleic acid molecule and one of the particular synthetic transcriptional activator fusion proteins described herein are present in a host cell at the same time.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following examples are provided to illustrate certain particular features and/or embodiments. The examples should not be construed to limit the disclosure to the particular features or embodiments exemplified.

EXAMPLES

Example 1: Identification of Plant Transactivation Interaction Motifs

Seven proteins were identified as homologous to the VP16 transactivation domain (SEQ ID NO:1): PTI4 (GenBank Accession No. ACF57857.1), ERF2 (GenBank Accession No. NP_199533.1), AtERF1(GenBank Accession No. NP_567530.4), ORCA2 (GenBank Accession No. CAB93940.1), DREB1A (GenBank Accession No. NP_567720.1), CBF1 (GenBank Accession No. NP_567721.1), and DOF1 (GenBank Accession No. NP_001105709.1). The amino acid sequence of the VP16 transactivation domain (SEQ ID NO:1) shared sequence similarity with regions of these putative plant transcription activators, and the VP16 sequence was used to locate a transactivation domain within each activator. The identified transactivation domains for these plant activator proteins are: SEQ ID NO:2 (PTI4), SEQ ID NO:3 (ERF2), SEQ ID NO:4 (AtERF1), SEQ ID NO:5 (ORCA2), SEQ ID NO:6 (DREB1A), SEQ ID NO:7 (CBF1), and SEQ ID NO:8 (DOF1). Next, the interaction motif of the VP16 transactivation subdomain II (FIG. 1; SEQ ID NO:9) was used to locate an interaction motif from the plant transactivation domains. FIG. 2 shows an alignment of VP16 with the plant transactivation domains, wherein the novel interaction motifs are highlighted.

Example 2: Modification of the Identified Interaction Motifs of Plant Transactivation Domains The interaction motifs of the identified plant transactivation domains were modified. New variants of the interaction motifs that contained the amino acid contact residues of the interaction motif of subdomain II of the VP16 transactivation domain were produced. Langlois et al. (2008) *J. Am. Chem. Soc.* 130:10596. Six amino acid contact residues of the VP16 transactivation domain are proposed to directly interact with Tfb1, a subunit of the transcription factor TFIIH. FIG. 1. Amino acids were introduced within the interaction motifs of the newly-identified plant transactivation domains to produce variant sequences.

We hypothesized that modifying the interaction motifs to contain the six amino acid contact residues identified from the VP16 interaction motif of Subdomain II would produce modified interaction motifs of the plant activators capable of interacting with a greater variety of transcription factors, thereby resulting in higher levels of protein expression.

ERF2 Modifications.

The region from Asn53 to Ala85 in ERF2 aligned to the subdomain II of VP16 transactivation domain (FIG. 2), and was identified as the plant transactivation domain sequence of ERF2. Modifications were introduced into the region that was found to correspond to the interaction motif of the subdomain II of the VP16 transactivation domain; from Asp66 to Asp76. The amino acid residues that were different from the six contact residues of the interaction motif of subdomain II of the VP16 transactivation domain were modified. These alterations resulted in an exemplary modified interaction motif of ERF2 (i.e., a variant interaction motif sequence) that is similar to that of subdomain II of the VP16 transactivation domain. FIG. 3.

Modifications to PTI4, AtERF1, ORCA2, DREB1A, CBF1, and DOF1 Interaction Motifs.

Modifications were introduced into the PTI4, AtERF1, ORCA2, DREB1A, CBF1 and DOF1 interaction motifs that are similar to those introduced into ERF2. The amino acid residues of the native sequences that were different from the six direct contact residues of the interaction motif of subdomain II of the VP16 transactivation domain were modified, thereby producing exemplary variant interaction motifs. These changes were introduced to make the plant variant interaction motifs similar (e.g., functionally similar) to that of subdomain II of the VP16 transactivation domain. Exemplary sequences of these variant or modified interaction motifs, as compared to the native interaction motif sequence of subdomain II of the VP16 transactivation domain, are listed in FIGS. 4-9.

Example 3: Testing the Interaction Motifs of the Plant Activation Domains in a *Saccharomyces cerevisiae* Reporter Strain

*Saccharomyces cerevisiae* Reporter Strain.

A *Saccharomyces cerevisiae* reporter strain was produced to test plant activation domains comprising either native or variant interaction motifs. A three-step cloning procedure resulted in the construction of the yeast integration vector, pHO-zBG-MEL1 (FIG. 10).

First, two separate fragments of the yeast SSA reporter vector, pNorMEL1 (Doyon et al. (2008) *Nat. Biotechnol.* 26(6):702-8), were amplified via PCR. The first fragment contained a yeast KanMX expression cassette, and was amplified from pNorMEL1 using the primers, KanMX-For (SEQ ID NO:59) and KanMX-Rev (SEQ ID NO:60), which add 5' SpeI, BamHI, NheI, PadI, BglII, KpnI, and 3' EcoRI restriction sites, respectively. The second fragment contained outward-facing homology arms to the yeast HO locus (Voth et al. (2001) *Nucleic Acids Res.* 29(12):E59-9) separated by a bacterial origin of replication, and was amplified using primers, HO-For (SEQ ID NO:61) and HO-Rev (SEQ ID NO:62). The two fragments were digested with EcoRI/SpeI and ligated to generate a KanMX selectable HO-targeting vector.

Next, the MEL1 expression cassette from pMEL1α2 (Melcher et al. (2000) *Gene* 247(1-2):53-61) was amplified with MEL1-For (SEQ ID NO:63) and MEL1-Rev (SEQ ID NO:64) primers, and cloned into the KpnI site of the KanMX selectable HO-targeting vector.

Finally, a Zinc Finger Protein (ZFP)-binding site (referred to as "HAS" for High Affinity Site) was synthesized de novo by an external vendor (DNA2.0, Menlo Park, Calif.). This site contained binding sites for Zinc-Finger Proteins (ZFPs) targeting the human CCR5 gene (Perez et al. (2008) *Nat. Biotechnol.* 26:808-16). The HAS fragment was PCR-amplified using the primers, HAS-For-F1 (SEQ ID NO:65) and HAS-For-R1 (SEQ ID NO:66), and cloned into the BamHI-PacI sites of the KanMX HO MEL1 vector, located upstream of the MEL1 reporter gene. This final vector was designated, pHO-zBG-MEL1 (FIG. 10).

pHO-zBG-MEL1 was linearized with NotI to expose the flanking homology arms for targeting to the yeast HO locus and transformed into *S. cerevisiae* strain, BY4741 MATa (Invitrogen, Carlsbad, Calif.), using the manufacturer's suggested protocol. Briefly, 3 mL of a log phase BY4741 culture was pelleted, and washed in TEL buffer (10 mM Tris HCL pH 8.0, 1 mM EDTA, 100 mM Lithium Acetate). The yeast cell pellet was resuspended in 360 µL yeast transformation solution (33.3% PEG-3350 (Sigma-Aldrich, St. Louis, Mo.), 0.1 M Lithium Acetate (Sigma-Aldrich), and 0.2 mg/mL Salmon Sperm DNA (Stratagene, La Jolla, Calif.) in 1×TE) containing 3 µg of linearized pHO-zBG-MEL1, and heat-shocked for 40 minutes at 42° C. Yeast cells were pelleted, washed, and grown in rich medium for 2 hours prior to selection on YPD plates containing 1 mg/L Geneticin® (Life Technologies, Carlsbad, Calif.). Resistant clones were re-streaked on YPD+Geneticin® plates, and used for subsequent transformations.

Yeast ZFP-Transcription Activator Expression Cassette Construction.

DNA constructs containing an in-frame CCR5 Zinc Finger Binding Protein (CCR5-ZFP)—plant transactivation interaction motif were constructed. The native and variant plant transactivation interaction motifs described in SEQ ID NOs:80-93 were mobilized as a BamHI/HindIII restriction enzyme fragment and cloned directly downstream of sequences encoding the CCR5-ZFP domains (Perez et al. (2008), supra). The resulting ZFP-transcription activator expression cassette utilized a GAL1,10 promoter (West et al. (1987) *Genes Dev.* 1:1118-31) and CYC1 terminator (Osborne et al. (1988) *Genes Dev.* 2:766-72), and was based on the yeast pRS315 series vector. The resulting vectors contained native and variant plant transactivation interaction motifs as in-frame fusions with the CCR5-ZFP.

In addition, several controls were included. An empty vector control and two different VP-16 transcription activator expression cassettes, SGMO VP16-CCR5 (SEQ ID NO:79) and VP16v2 CCR5-CCRS, were used in the study. Both of the VP-16 transcription activator expression cassettes were driven by the GAL1,10 promoter, and terminated by the CYC1 terminator. The empty vector control contained only the CCR5-ZFP domains, and did not contain a transactivation interaction motif Yeast Activity Assay.

Overnight cultures of the BY4741 reporter line strain were grown in YPD+Geneticin®, and 1 µg of vector containing a ZFP-transcription activator expression cassette was delivered using a standard yeast transformation protocol in a 96-well format. All transformations were duplicated. Transformed yeast cells were recovered in Synthetic Dextrose medium lacking leucine (SD-Leu) to select for the vector containing the ZFP-transcription activator expression cassette. After 72 hours, the yeast cells were enriched by a 1:10 dilution of the transformants in SD-Leu and grown a further 24 hours. Next, the yeast cells were diluted 1:10 into synthetic raffinose medium lacking leucine (SR-Leu) to de-repress the GAL1,10 promoter. 24 hours later, yeast cells were pelleted, and resuspended in synthetic galactose medium lacking leucine (SG-Leu). At time points of 0, 3, and 6 hours post-galactose induction, 110 µL of yeast cells were harvested for a MEL1 assay.

In the MEL1 assay, 100 µL of the 110 µL of yeast cells were diluted in 100 µL of water and the optical density at 600 nm ($OD_{600}$) was measured using a spectrophotometer. The remaining 10 µL of yeast cells were incubated in 90 µL MEL1 buffer (77 mM $Na_2HPO_4$, 61 mM Citric Acid, 2 mg/mL PNPG (Sigma-Aldrich)) for 1 hour at 30° C. The reaction was stopped by the addition of 100 µL 1M $Na_2CO_3$. MEL1 activity was assessed at $OD_{405}$, and mU were calculated using a formula based on the ratio of the $OD_{405}$ and $OD_{600}$ measurements (Doyon et al. (2008) *Nat. Biotechnol.* 26(6):702-8).

Figure 11:
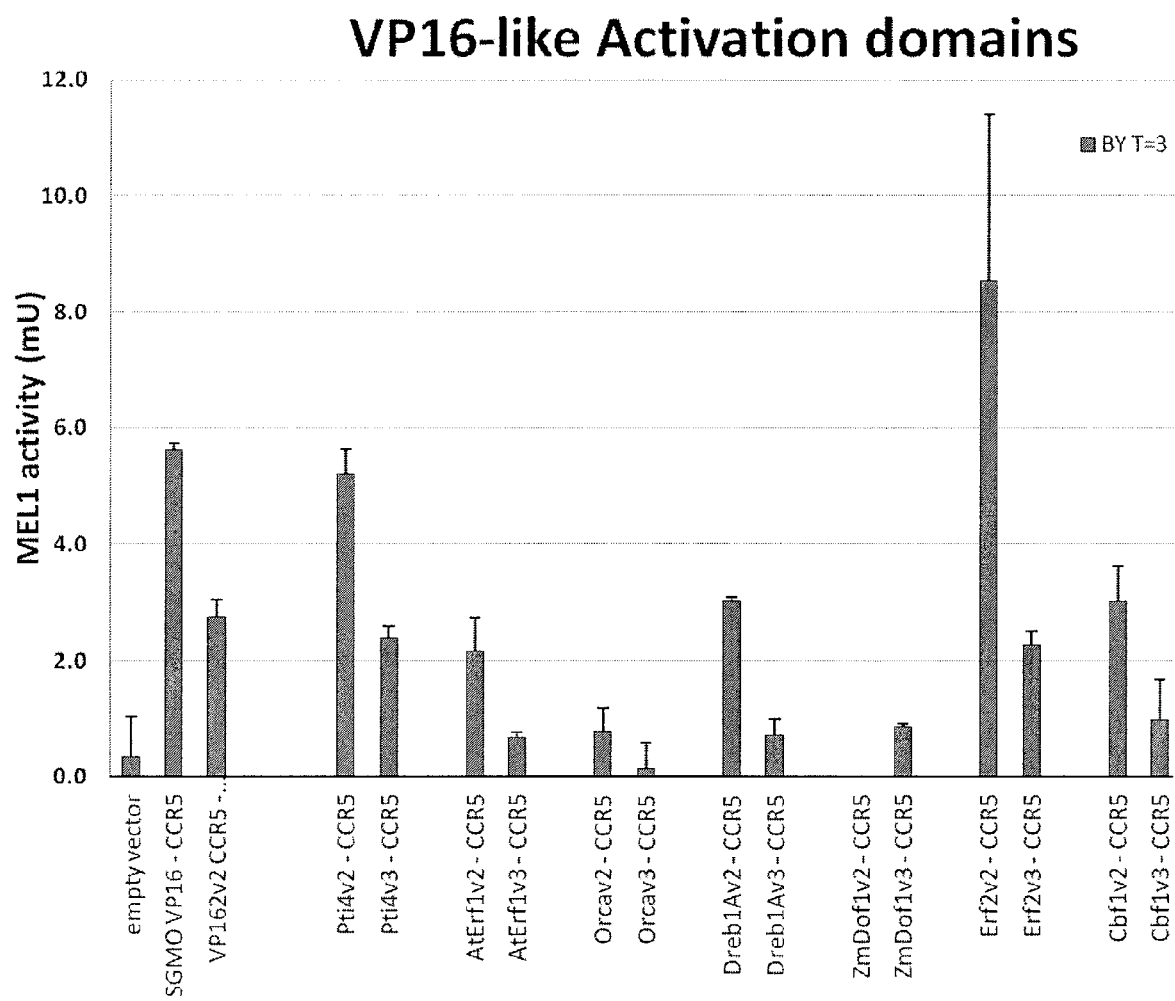
FIG. 11 includes a graphical illustration of the expression levels of the Mel1 reporter gene that resulted in yeast from activation by the different plant transactivation interaction motifs.

The expression level of the Mel1 reporter gene that resulted from activation by the different plant transactivation interaction motifs is shown in FIG. 11. The expression of the MEL1 protein that resulted from these different plant transactivation interaction motifs was compared to an empty vector control and the activation of Mel1 from subdomain II of the VP16 transactivation domain (SEQ ID NO:1) (VP16 (v2)-CCR5) and SGMO VP16 (SGMO VP16-CCR5).

The modified ERF2 (v2) plant transactivation interaction motif produced unexpectedly high levels of expression, as compared to the VP16 control. In addition, expression of Mel1 with this variant plant transactivation interaction motif resulted in an increase over the native version of the ERF2 (v3) plant transactivation interaction motif.

The modified PTI4 (v2) plant transactivation interaction motif expressed MEL1 protein at levels similar to the VP16 transactivation domain control. However, the modifications introduced into the PTI4 interaction motif resulted in significantly higher levels of Mel1 expression, as compared to the native PTI4 (v3) plant transactivation interaction motif.

The AtERF1(v3), AtERF1(v2), ORCA2(v3), ORCA2 (v2), DOF1(v3), DOF1(v2), DREB1A(v3), DREB1A(v2), CBF1(v3) and CBF1(v2) plant transactivation interaction motifs did not result in high levels of expression of Mel1 in the yeast assay, as compared to the VP16 controls. However, the AtERF1, DREB1A, and CBF1 plant transactivation interaction motifs did drive expression of Mel1 in yeast. Only the ORCA2 (v3) and DOF1 (v2) plant transactivation interaction motifs did not result in any expression of Mel1 in the yeast assay.

The levels of MEL1 produced by the plant transactivation domain for the modified variant (v2) plant transactivation interaction motifs were generally higher as compared to the native (v3) plant transactivation interaction motifs in the Mel1 yeast assay. The only modified plant transactivation interaction motif which did not drive expression of Mel1 in the yeast assay was the DOF1 (v2) interaction motif. This plant transactivation interaction motif did not produce any MEL1 expression in the yeast assay.

Example 4: Function of Interaction Motifs of the Plant Activation Domains in Tobacco Containing a Reporter Construct Comprising a Zinc Finger DNA Binding Domain Reporter Construct pDAB9897.

Eight tandem repeats of the Z6 DNA binding domain polynucleotide sequence (SEQ ID NO:67; Yokoi et al. (2007) *Mol Ther.* 15(11):1917-23) were synthesized de novo (IDT, Coralsville, Iowa) with SacH sites added to the 5' and 3' ends to facilitate cloning. The entire 8X-Z6 binding domain (SEQ ID NO:68) was subsequently cloned into a pre-existing Gateway® Entry vector containing desired plant expression elements. The 8X-Z6 binding sites were mobilized on a SacH fragment, and cloned immediately upstream of the *Arabidopsis thaliana* actin-2 promoter (AtAct2 promoter v2; An et al. (1996) *Plant J.* 10:107-21) using a unique SacH site found in the backbone vector. Subsequently, the gus gene (GUS; Jefferson (1989) *Nature* 342:837-8) was cloned into this vector under direct control of the *A. thaliana* actin-2 promoter using unique NcoI/SacI sites, with the ATG codon of the NcoI site forming the initation codon. An Atu ORF23 3'UTR (*Agrobacterium tumefaciens* open reading frame-23, 3'untranslated region; European Patent Application No. EP 222493 A1) was used to terminate transcription.

Figure 12:
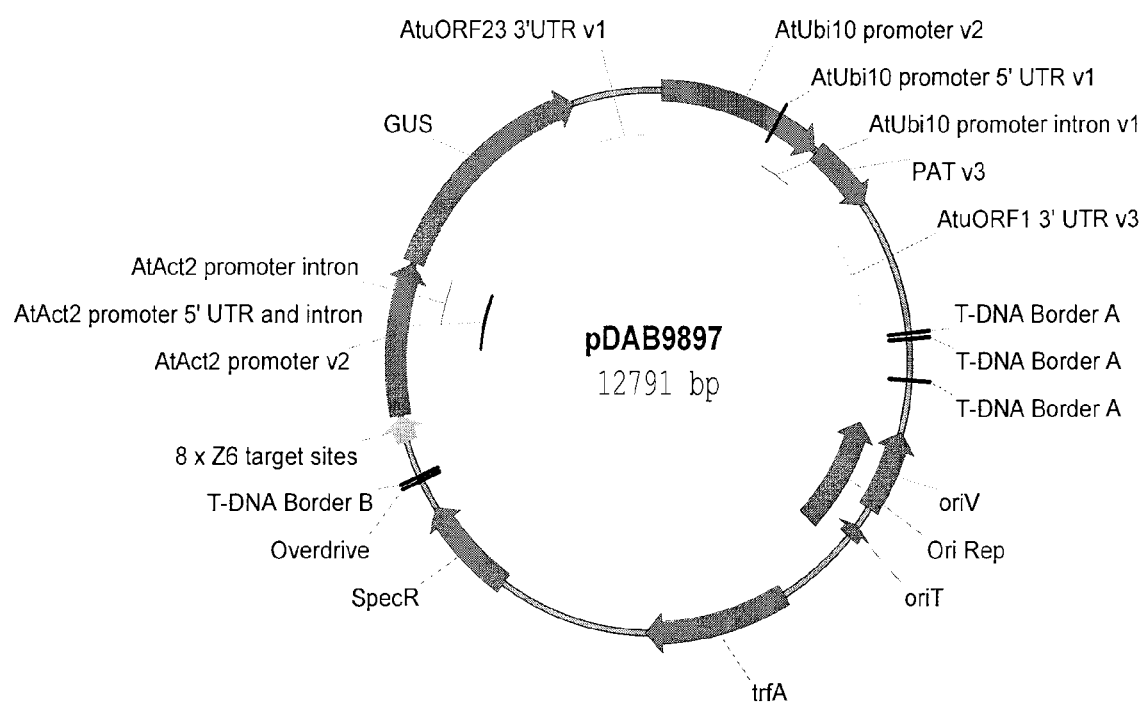
FIG. 12 includes a map of plasmid pDAB9897: Arabidopsis thaliana actin-2 promoter containing 8 tandem zinc finger (Z6) binding sites 548-749 base pairs upstream of transcriptional start site driving a gus reporter gene used for testing plant transactivation interaction motifs zinc finger fusion proteins. The binary vector also contains an A. thaliana ubiquitin-10 promoter driving a pat selectable marker for target reporter plant event production.

The final transformation vector, pDAB9897 (FIG. 12), was the result of a Gateway® ligation with a destination vector containing an *A. thaliana* ubiquitin-10 promoter (At Ubi10 Promoter v2 (Callis et al. (1990) *J. Biol. Chem.* 265:12486-93))::phosphinothricin acetyl transferase gene (pat v3 (Wohlleben et al. (1988) *Gene* 70:25-37))::*A. tumefaciens* open reading frame-1, 3'untranslated region (At-uORF1 3'UTR v3 (Huang et al. (1990) *J. Bacteriol.* 172:1814-22) selectable marker cassette for plant selection. The final transformation vector was confirmed via sequencing, and transformed into *A. tumefaciens* strain, LBA4404 (Invitrogen, Carlsbad, Calif.).

*Agrobacterium*-Mediated Transformation of Tobacco with pDAB9897.

To make transgenic reporter plant events, leaf discs (1 cm$^2$) cut from Petit Havana tobacco plants were incubated in an overnight culture of *A. tumefaciens* strain LBA4404 harboring plasmid pDAB9897, grown to OD$_{600}$~1.2 nm, blotted dry on sterile filter paper, and then placed onto MS medium (Phytotechnology Labs, Shawnee Mission, Kans.) and 30 g/L sucrose with the addition of 1 mg/L indoleacetic acid and 1 mg/L benzyamino purine in 60×20 mm dishes (5 discs per dish) sealed with Nescofilm® (Karlan Research Products Corporation, Cottonwood, Ariz.). Following 48 hours of co-cultivation, leaf discs were transferred to the same medium with 250 mg/L cephotaxime and 5 mg/L BASTA®. After 3-4 weeks, plantlets were transferred to MS medium with 250 mg/L cephotaxime and 10 mg/L BASTA® in PhytaTrays™ for an additional 2-3 weeks prior to leaf harvest and molecular analysis.

Copy Number and PTU Analysis of Reporter Events.

PCR DNA Isolation. Transgenic tobacco plant tissue was harvested from newly-grown plantlets and lyophilized (Labconco, Kansas City, Mo.) for at least 2 days in 96-well collection plates (Qiagen, Valencia, Calif.). DNA was then isolated using the DNEasy™ 96 well extraction kit (Qiagen), according to the manufacturer's instructions. A Model 2-96A Kleco™ tissue pulverizer (Garcia Manufacturing, Visalia, Calif.) was used for tissue disruption.

Southern DNA Isolation. Transgenic tobacco plant tissue was harvested from newly-grown plantlets and lyophilized (Labconco, Kansas City, Mo.) for at least 2 days in 2 mL conical tubes (Eppendorf). DNA was then isolated using the DNEasy™ Plant Mini extraction kit (Qiagen), according to the manufacturer's instructions. A Model 2-96A Kleco™ tissue pulverizer (Garcia Manufacturing) was used for tissue disruption.

DNA Quantification. Resulting genomic DNA was quantified using a Quant-iT™ PicoGreen® DNA assay kit (Molecular Probes, Invitrogen, Carlsbad, Calif.). Five pre-quantified DNA standards ranging from 20 ng/μL to 1.25 ng/μL (serially diluted) were used for standard curve generation. Samples were first diluted with 1:10 or 1:20 dilutions to be within the linear range of the assay, and concentrations of genomic DNA were determined according to the manufacturer's protocol. Fluorescence was then recorded using a Synergy2™ plate reader (Biotek, Winooski, Vt.). Genomic DNA concentration was estimated from a standard curve calculated from background fluorescence corrections. Using TE or water, DNA was then diluted to a common concentration of 10 ng/μL for PCR using a Biorobot3000™-automated liquid handler (Qiagen). DNA for Southern analysis was left undiluted.

Copy Number Estimation. Putative transgenic events were analyzed for integration complexity using a multiplexed DNA hydrolysis probe assay analogous to the TaqMan® assay (Applied Biosystems, Carlsbad, Calif.). The copy number of the transgene insert was estimated using sequence-specific primers and probes for both the pat transgene and an endogenous tobacco reference gene, pal (phenylalanine ammonium lyase; GenBank Accession No. AB008199). Assays for both genes were designed using LightCycler® Probe Design Software 2.0 (Roche Applied Science, Indianapolis, Ind.). Real time PCR for both genes was evaluated using the LightCycler®480 system (Roche Applied Science).

For amplification, LightCycler®480 Probes Master mix (Roche Applied Science) was prepared at 1× final concentration in a 10 μL volume multiplex reaction containing 0.4 μM of each primer and 0.2 μM of each probe. Table 1. A two-step amplification reaction was performed with an extension at 58° C. for 38 seconds with fluorescence acquisition. All samples were run in triplicate, and the averaged Ct values were used for analysis of each sample. Analysis of real time PCR data was performed using LightCycler® software (Roche Applied Science) via the relative quant module, and is based on the ΔΔCt method. A sample of gDNA from a single copy calibrator was included to normalize results. The single copy calibrator event was previously identified by Southern analysis, and was confirmed to have a single insert of the pat gene.

TABLE 1

Sequences of the primers and probes used in both the pat and pal hydrolysis probe (HP) assays. The fluorescent epitope of each probe was different, which allowed the assays to be run simultaneously as a multiplexed reaction.

| Primer | Nucleotide Sequence (5'-3') | Type |
|---|---|---|
| TQPATS | ACAAGAGTGGATTGATGATCTAGAGAGGT (SEQ ID NO: 69) | Primer |
| TQPATA | CTTTGATGCCTATGTGACACGTAAACAGT (SEQ ID NO: 70) | Primer |
| TQPATFQ | CY5-GGTGTTGTGGCTGGTATTGCTTACGC TGG-BHQ2 (SEQ ID NO: 71) | Cy5 Probe |
| TQPALS | TACTATGACTTGATGTTGTGTGGTGACTGA (SEQ ID NO: 72) | Primer |
| TQPALA | GAGCGGTCTAAATTCCGACCCTTATTTC (SEQ ID NO: 73) | Primer |
| TQPALFQ | 6FAM-AAACGATGGCAGGAGTGCCCTTTTT CTATCAAT-BHQ1 (SEQ ID NO: 74) | 6FAM Probe |

PTU PCR. Low copy events were subsequently screened by PCR for intact plant transcriptional units (PTU). Using the Blu636 (SEQ ID NO:75) and Blu637 (SEQ ID NO:76) primers, correct amplification resulted in a 3.7 kb product consisting of the Z6-Act2/GUS/AtORF23 PTU (3,771 bp). Phusion® GC Master Mix (New England Biolabs, Beverley, Mass.) was used with the following reaction conditions: 98° C. for 30 seconds, followed by 30 cycles of 98° C. for 10 seconds, 67° C. for 30 seconds, 72° C. for 2 minutes, and a final extension of 72° C. for 10 minutes. In addition to the PTU PCR reaction detailed above, amplification of an endogenous gene, chs (chalcone synthase; Genbank Accession No. FJ969391.1), was also included to confirm the quality of the genomic DNA templates. 3'CHS Forward (SEQ ID NO:77) and 3'CHS Reverse (SEQ ID NO:78) primers were included in the reaction, which produced a 350 bp amplification product. 20 µL reactions were used, with a final concentration of 0.5 µM for the transgene primers and 0.2 µM for the endogenous reference gene.

Southern Analysis. For each sample, 5 µg genomic DNA was thoroughly digested with the restriction enzyme, AseI (New England Biolabs), by incubation at 37° C. overnight. The digested DNA was concentrated by precipitation with Quick Precip™ Solution (Edge Biosystems, Gaithersburg, Md.), according to the manufacturer's suggested protocol. The genomic DNA was then resuspended in 25 µL water at 65° C. for 1 hour. Resuspended samples were loaded onto a 0.8% agarose gel prepared in 1×TAE buffer, and electrophoresed overnight at 1.1 V/cm in 1×TAE. The gel was immersed in denaturation buffer (0.2 M NaOH/0.6 M NaCl) for 30 minutes, followed by immersion in neutralization buffer (0.5 M Tris-HCl (pH 7.5)/1.5 M NaCl) for 30 minutes.

Transfer of DNA fragments to nylon membranes was performed by passively wicking 20×SSC buffer overnight through the gel onto treated Immobilon™-NY+ transfer membrane (Millipore, Billerica, Mass.) using a chromatography paper wick and paper towels. Following transfer, the membrane was briefly washed with 2×SSC, cross-linked with the Stratalinker® 1800 (Stratagene, LaJolla, Calif.), and vacuum baked at 80° C. for 3 hours.

Blots were incubated with pre-hybridization solution (PerfectHyb™ plus, Sigma-Aldrich) for 1 hour at 65° C. in glass roller bottles using a Robbins Scientific Model 400 hybridization incubator (Robbins Scientific, Sunnyvale, Calif.). Probes were prepared from a PCR fragment containing the entire coding sequence. The PCR amplicon was purified using Qiaex II® gel extraction kit (Qiagen), and labeled with [$\alpha^{32}$P]dCTP via the Random RT Prime-iT® labeling kit (Stratagene, La Jolla, Calif.). Blots were hybridized overnight at 65° C. with a denatured probe added directly to the pre-hybridization solution to approximately 2 million counts blot$^{-1}$ mL$^{-1}$. Following hybridization, blots were sequentially washed at 65° C. with 0.1×SSC/0.1% SDS for 40 minutes. Finally, the blots were exposed to storage phosphor imaging screens, and imaged using a Molecular Dynamics™ Storm™ 860 imaging system. True single copy integration events were confirmed by the identification of a single hybridizing band.

Generation of Homozygous $T_2$ Reporter Plants.

A total of 51 BASTA®-resistant plants were generated, of which 24 were found to be low-complexity (1-2 copies of pat) based on hydrolysis probe analysis of copy number. Of these low-complexity events, 18 displayed an intact PTU, as determined by PCR analysis. Following Southern blot analysis, two single-copy, intact PTU events were selected and grown to maturity in the greenhouse, where they were allowed to self-pollinate. $T_1$ seed was then collected, surface-sterilized (for 3 min in 20% bleach, followed by two sterile, distilled water rinses), and germinated on MS medium (Phytotechnology Labs, Shawnee Mission, Kans.) and 30 g/L sucrose in PhytaTrays™ (Sigma, St. Louis, Mo.). Following zygosity screening via pat copy number analysis, homozygous $T_1$ plants were selected, grown to maturity in the greenhouse, and allowed to self-pollinate. $T_2$ seed was then collected, surface-sterilized, and germinated as described previously, and used to generate reporter plants for plant transactivation testing.

Plant ZFP-Plant Transcription Activator Expression Constructs.

Plant ZFP-transcription activator constructs containing a variant or native plant transactivation interaction motif were constructed. Plant transactivation interaction motifs (both native and modified variants) flanked by the restriction enzyme sites BamHI/SacI for cloning were synthesized de novo (DNA2.0, Menlo Park, Calif.). The plant transactivation interaction motifs were mobilized on a BamHI/SacI fragment, and cloned immediately downstream of the Z6 Zinc Finger DNA binding domain (Yokoi et al. (2007), supra) using unique BamHI/SacI sites found in an existing Gateway® Entry backbone vector. Upon completion of this step, the ZFP-transcription activator constructs (containing a Z6 DNA Zinc Finger Protein binding domain fused to the plant transactivation interaction motif) were placed under the control of the constitutive Cassava Vein Mosaic Virus promoter (CsVMV promoter v2; Verdaguer et al. (1996) *Plant Mol. Biol.* 31:1129-39), and terminated with the ORF23 3'UTR from *A. tumefaciens*. Final transformation vectors (Table 2), resulted from a Gateway®-mediated ligation (Invitrogen, Carlsbad, Calif.) with a destination vector containing an *A. thaliana* ubiquitin-3 promoter (At Ubi3 promoter v2; Callis et al. (1995) *Genetics,* 139(2):921-39))/hygromycin phosphotransferase II (HPTII v1; Gritz et al. (1983) Gene 25(2-3):179-88)/*A. tumefaciens* open reading frame-24, 3' untranslated region (Atu ORF24 3'UTR v2) cassette used for plant selection.

TABLE 2

Plant ZFP-transcription activator constructs tested in tobacco. The sequence identifier provides the DNA sequence of the plant transactivation interaction motif that was fused to the Z6 Zinc Finger binding Protein and expressed in the binary vector.

Figure 13:
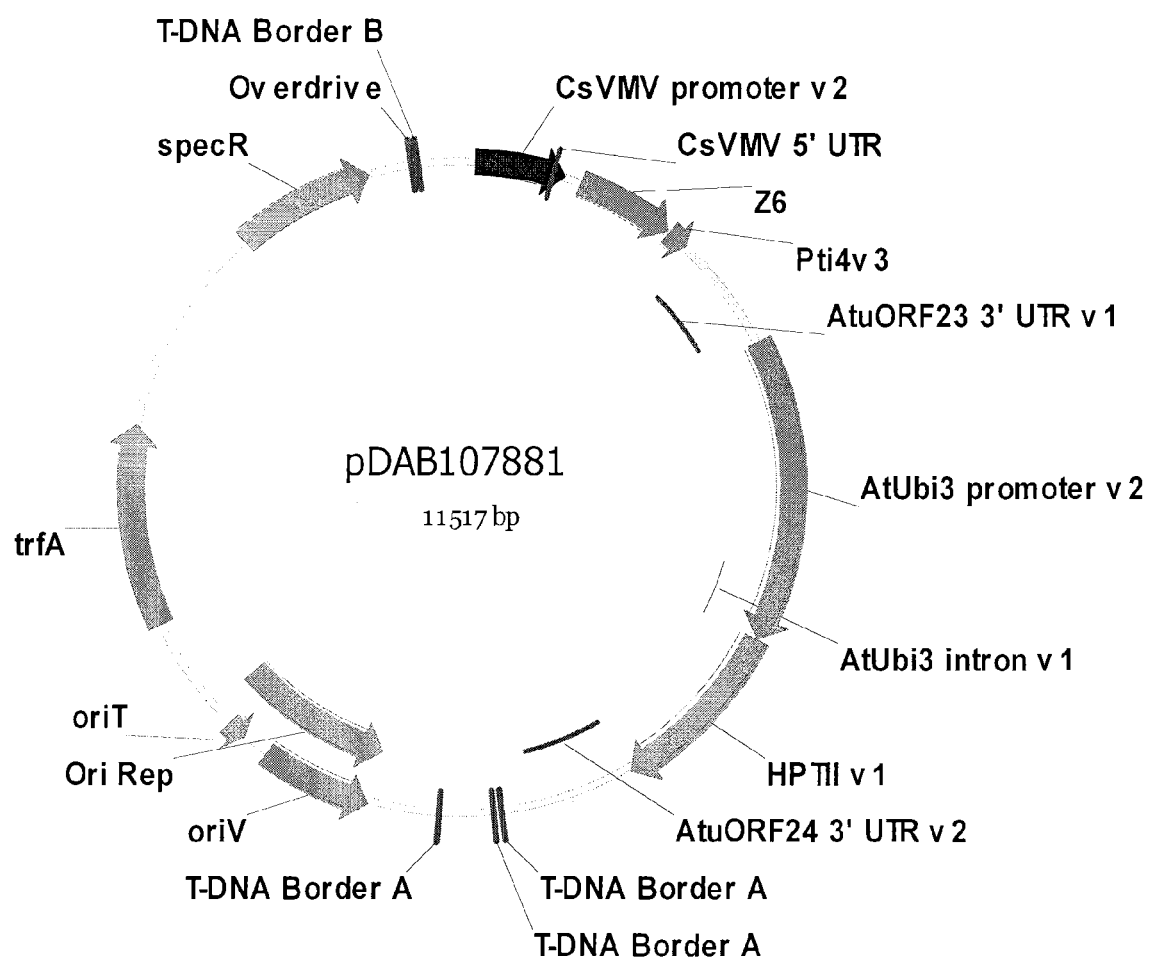
FIG. 13 includes a map of plasmid pDAB107881.
Figure 14:
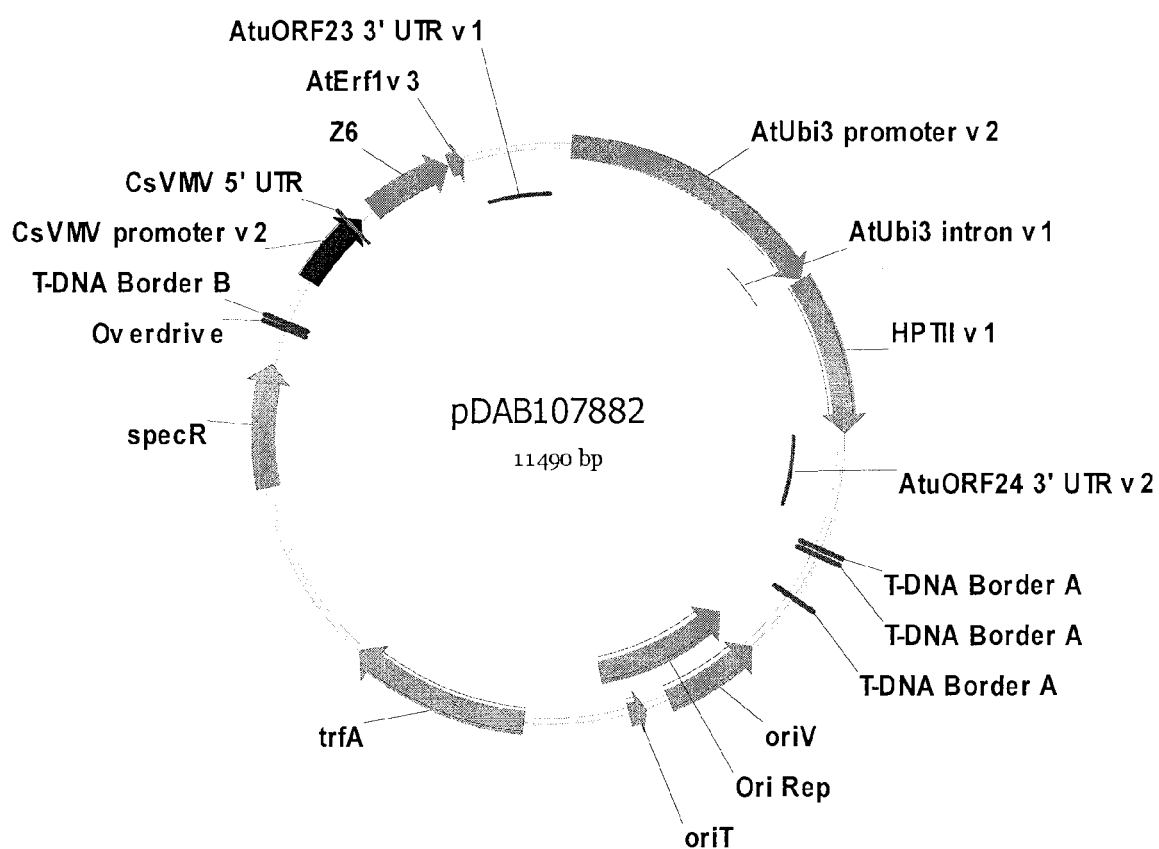
FIG. 14 includes a map of plasmid pDAB107882.
Figure 15:
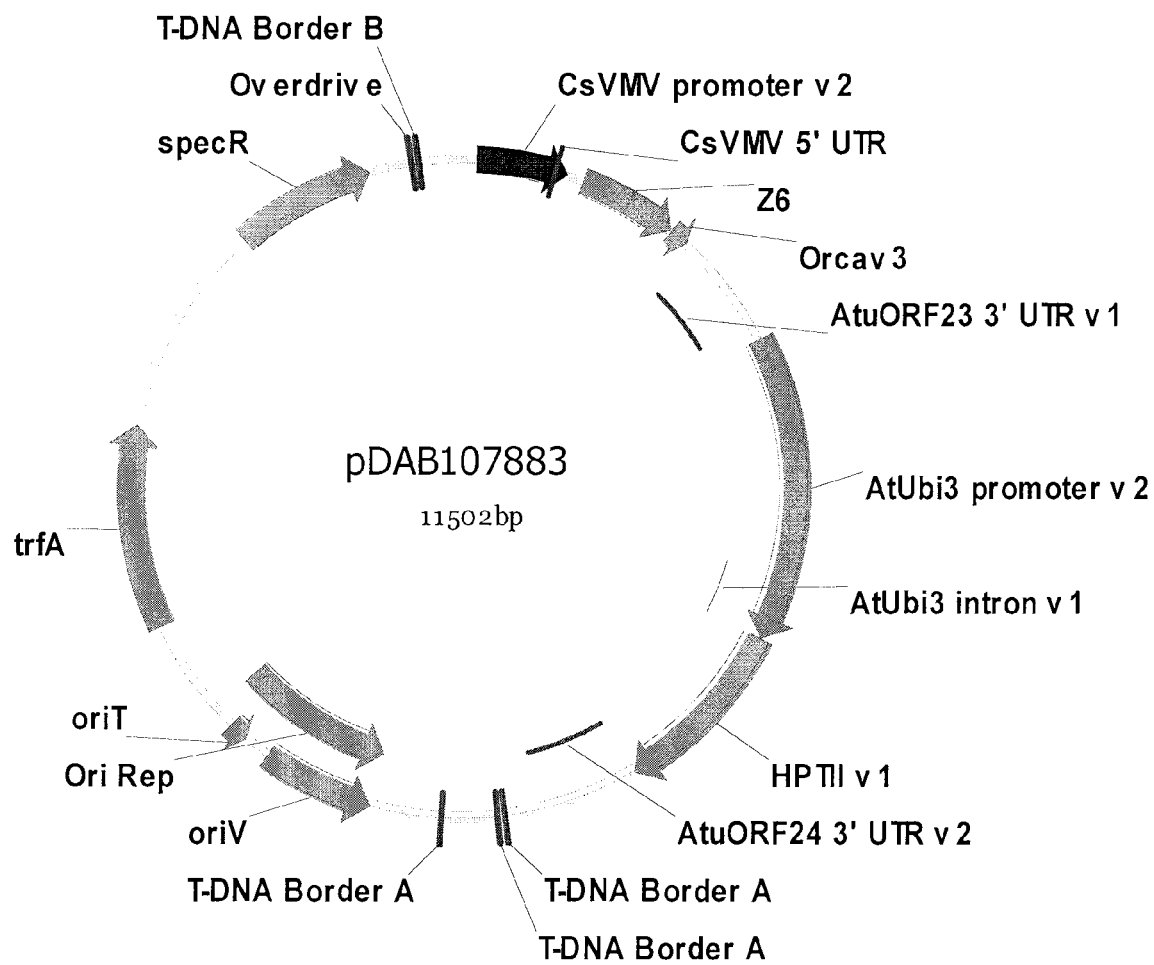
FIG. 15 includes a map of plasmid pDAB107883.
Figure 16:
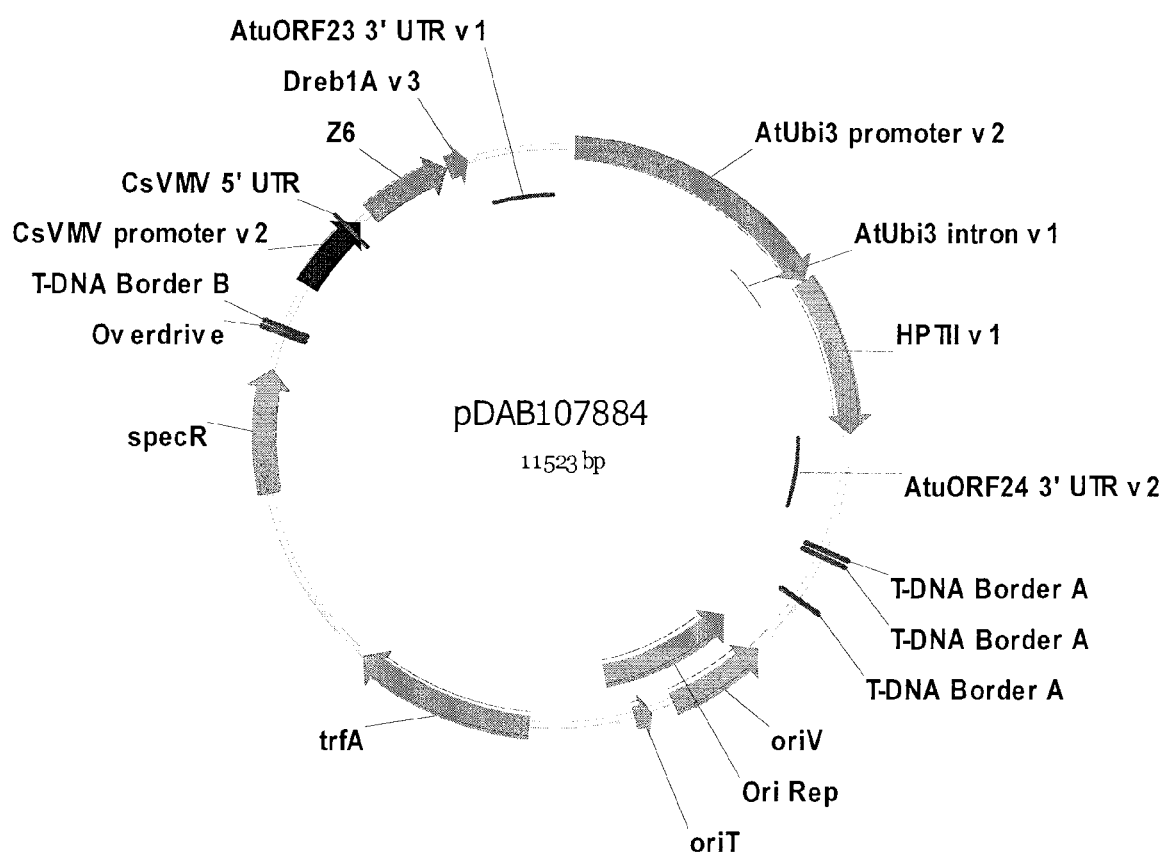
FIG. 16 includes a map of plasmid pDAB107884.
Figure 17:
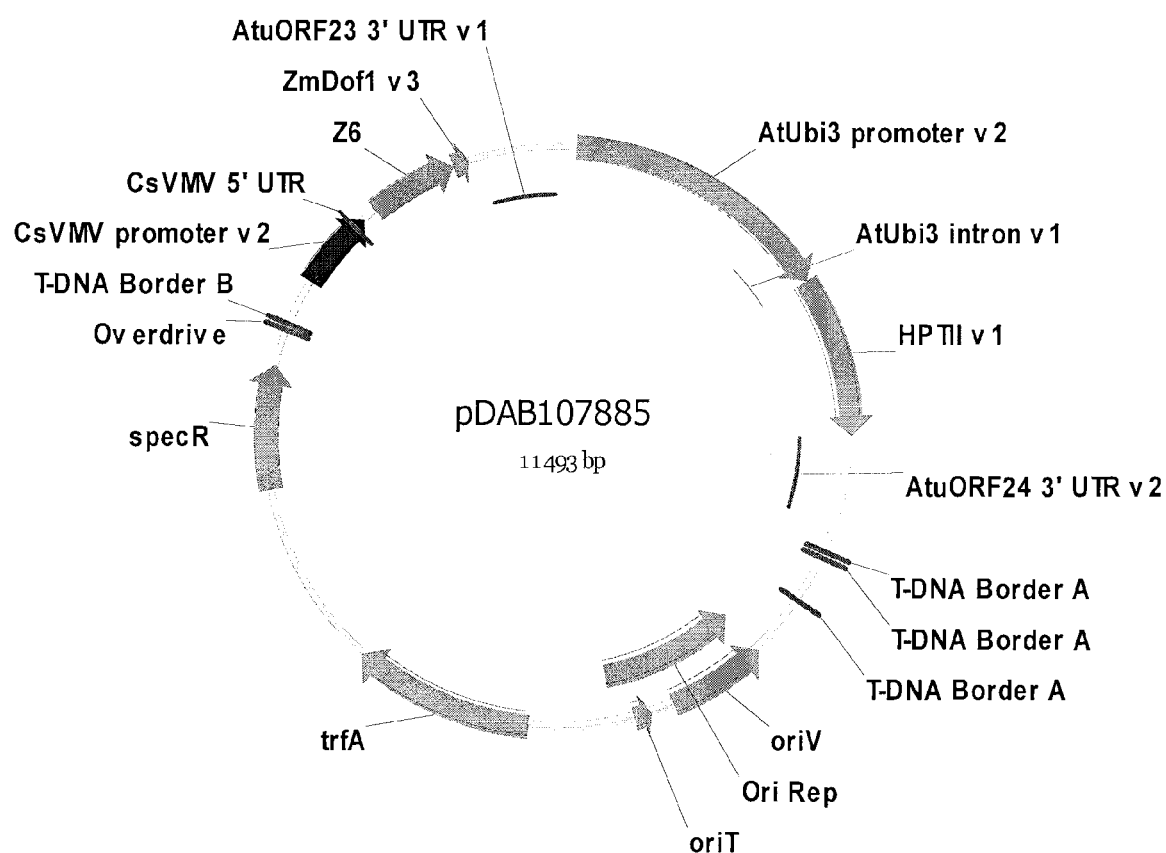
FIG. 17 includes a map of plasmid pDAB107885.
Figure 18:
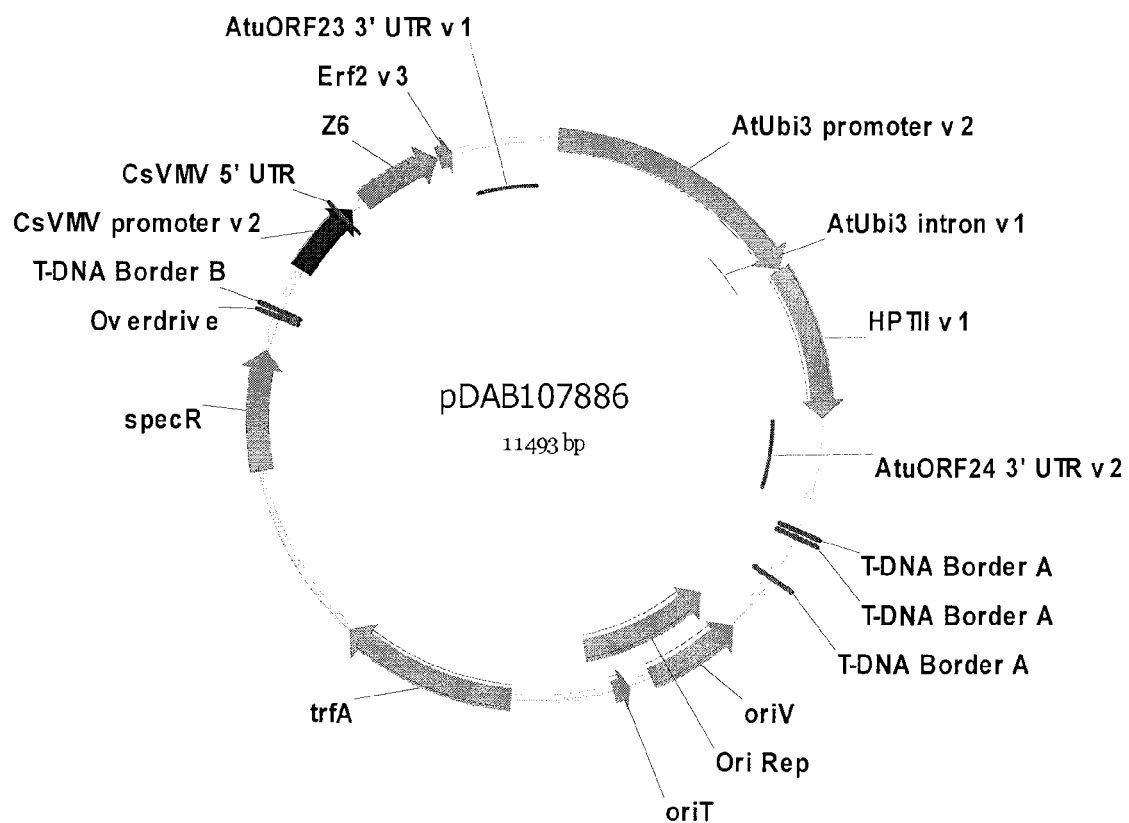
FIG. 18 includes a map of plasmid pDAB107886.
Figure 19:
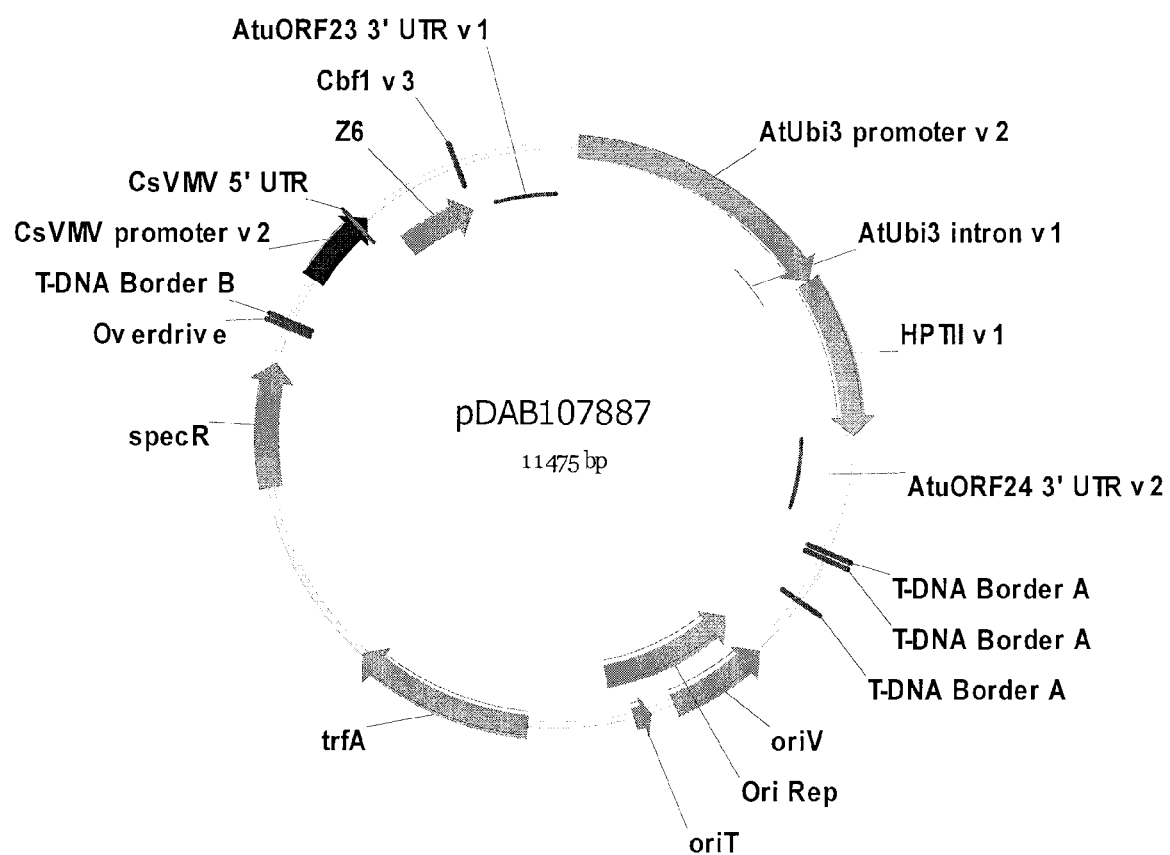
FIG. 19 includes a map of plasmid pDAB107887.
Figure 20:
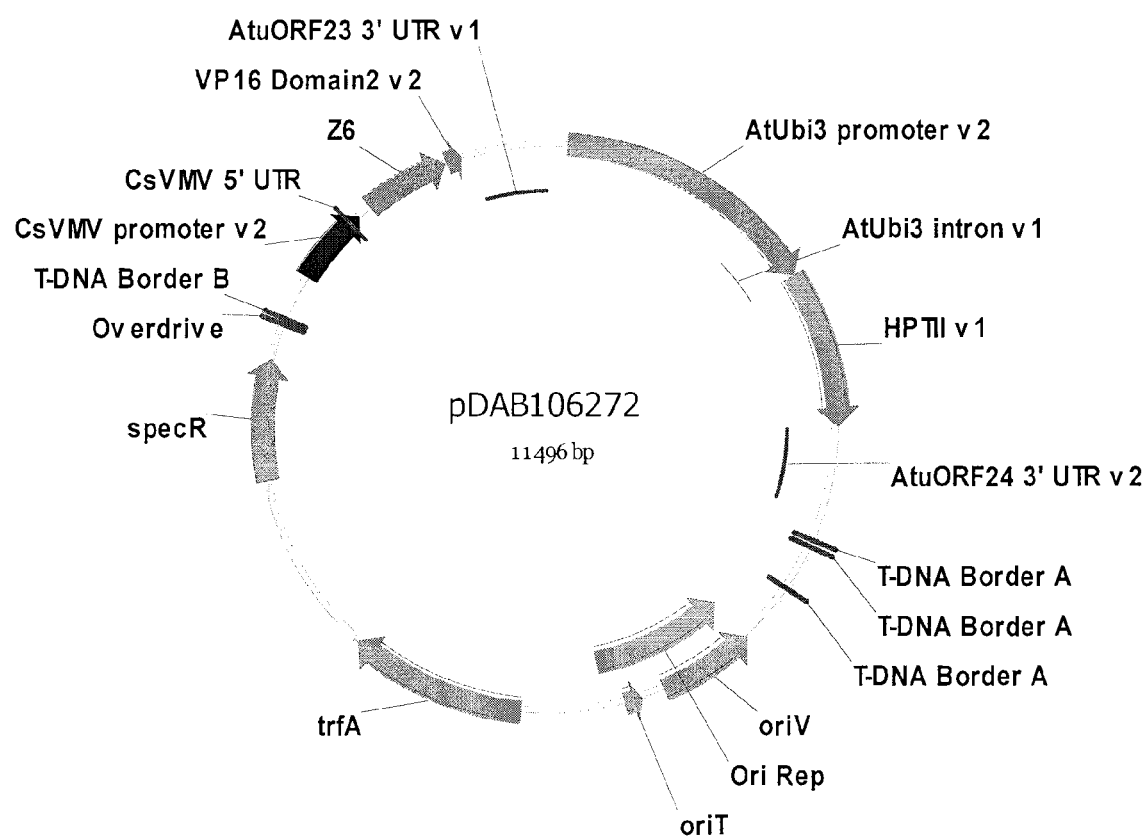
FIG. 20 includes a map of plasmid pDAB106272.
Figure 21:
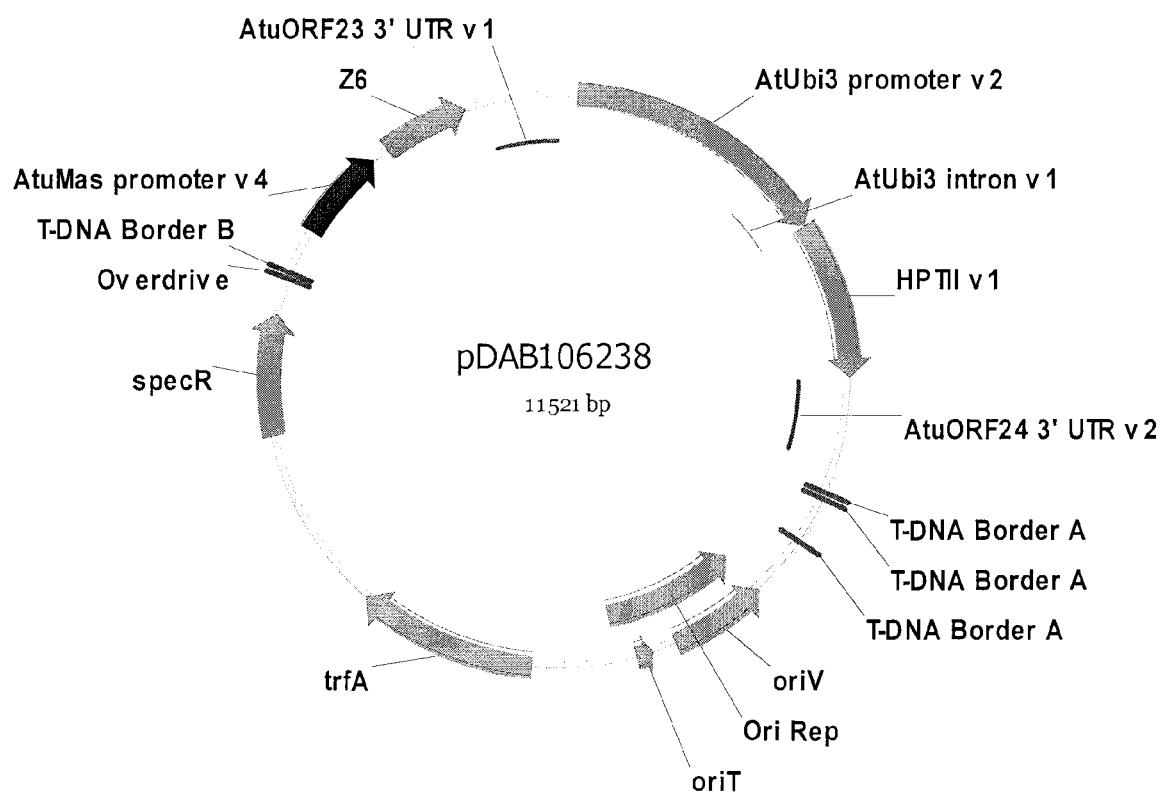
FIG. 21 includes a map of plasmid pDAB106238.
Figure 22:
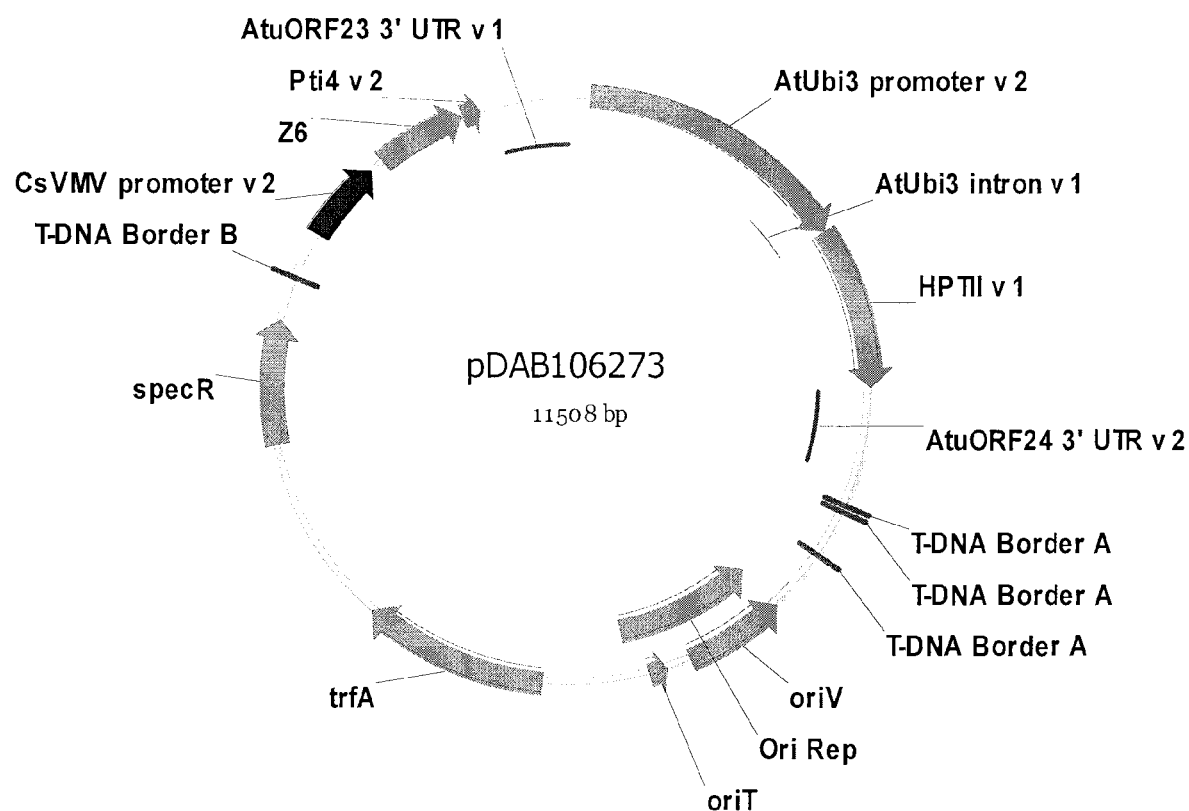
FIG. 22 includes a map of plasmid pDAB106273.
Figure 23:
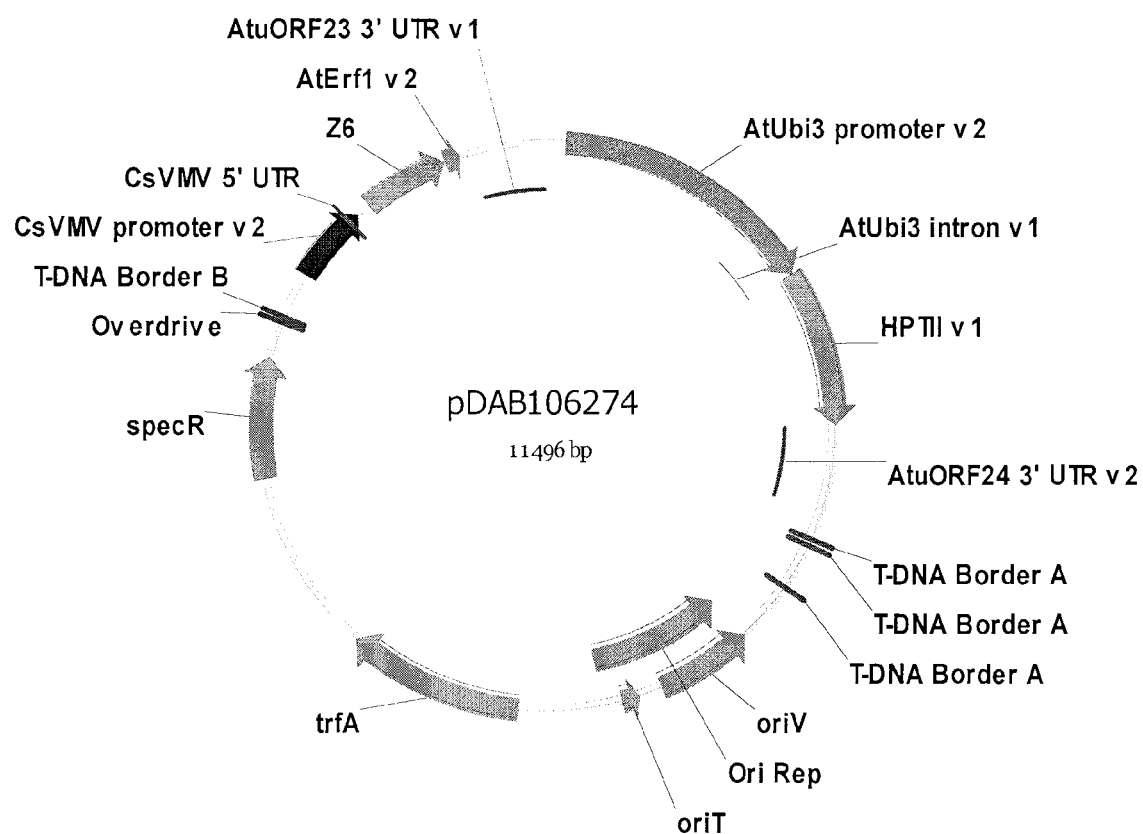
FIG. 23 includes a map of plasmid pDAB106274.
Figure 24:
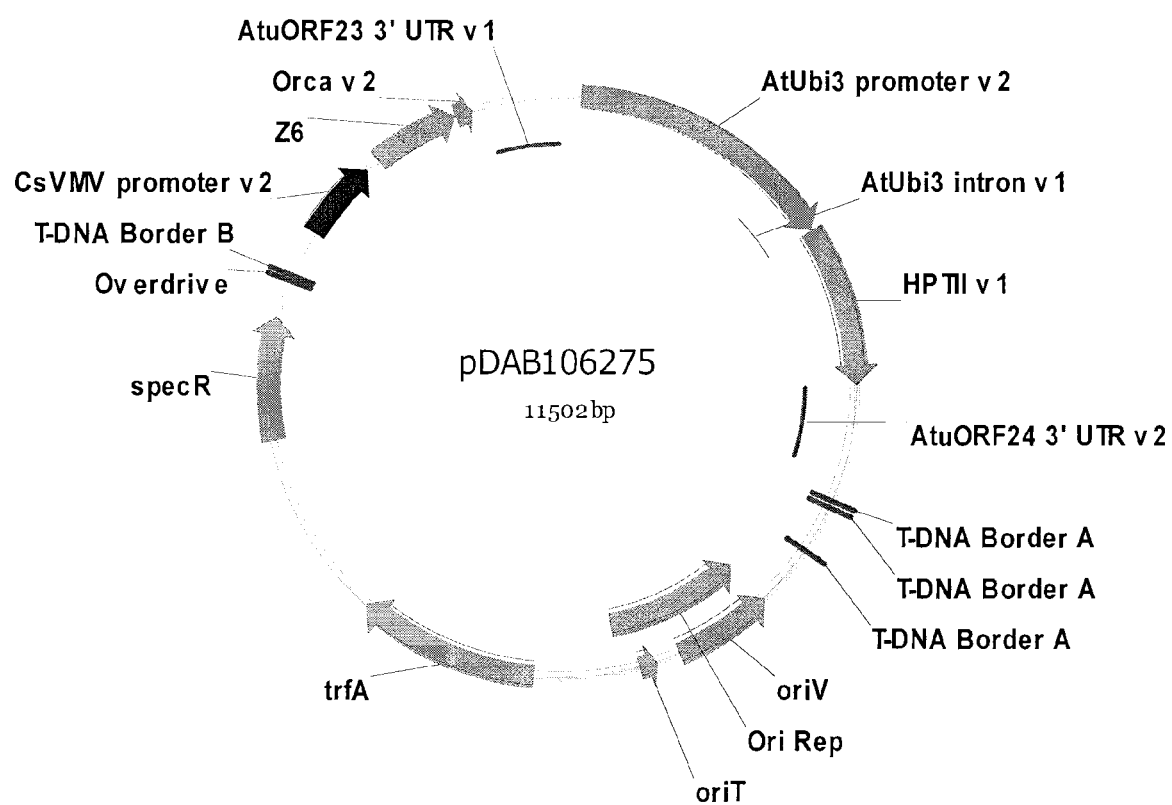
FIG. 24 includes a map of plasmid pDAB106275.
Figure 25:
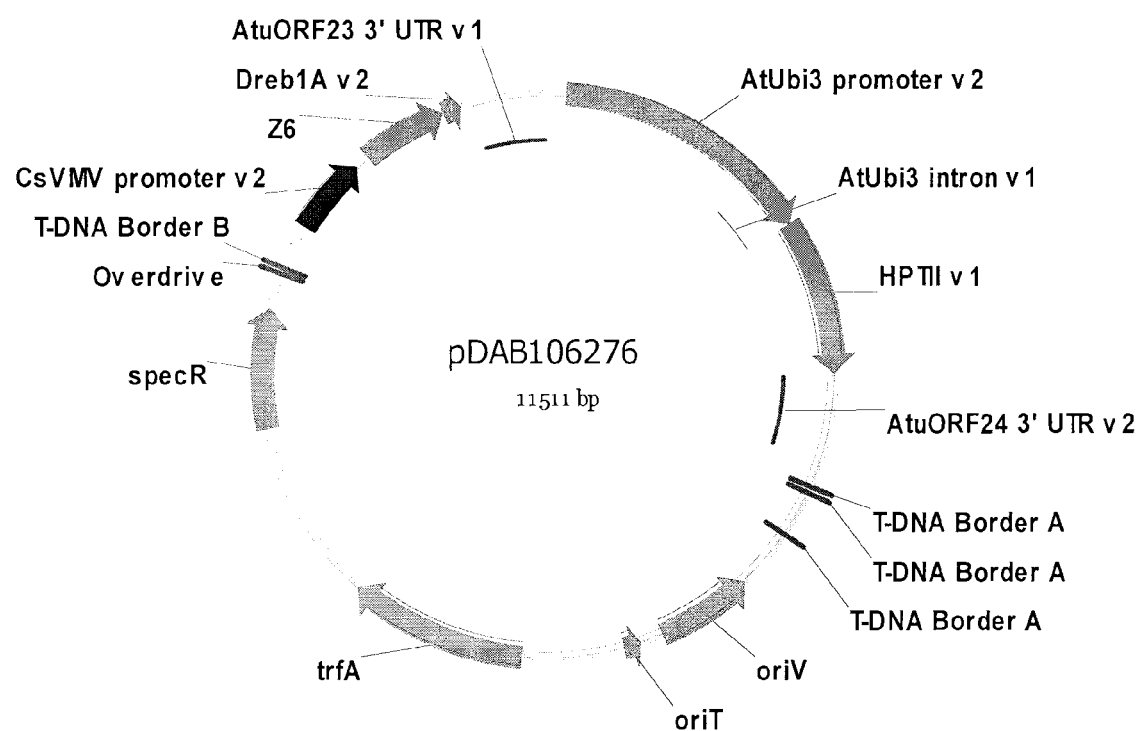
FIG. 25 includes a map of plasmid pDAB106276.
Figure 26:
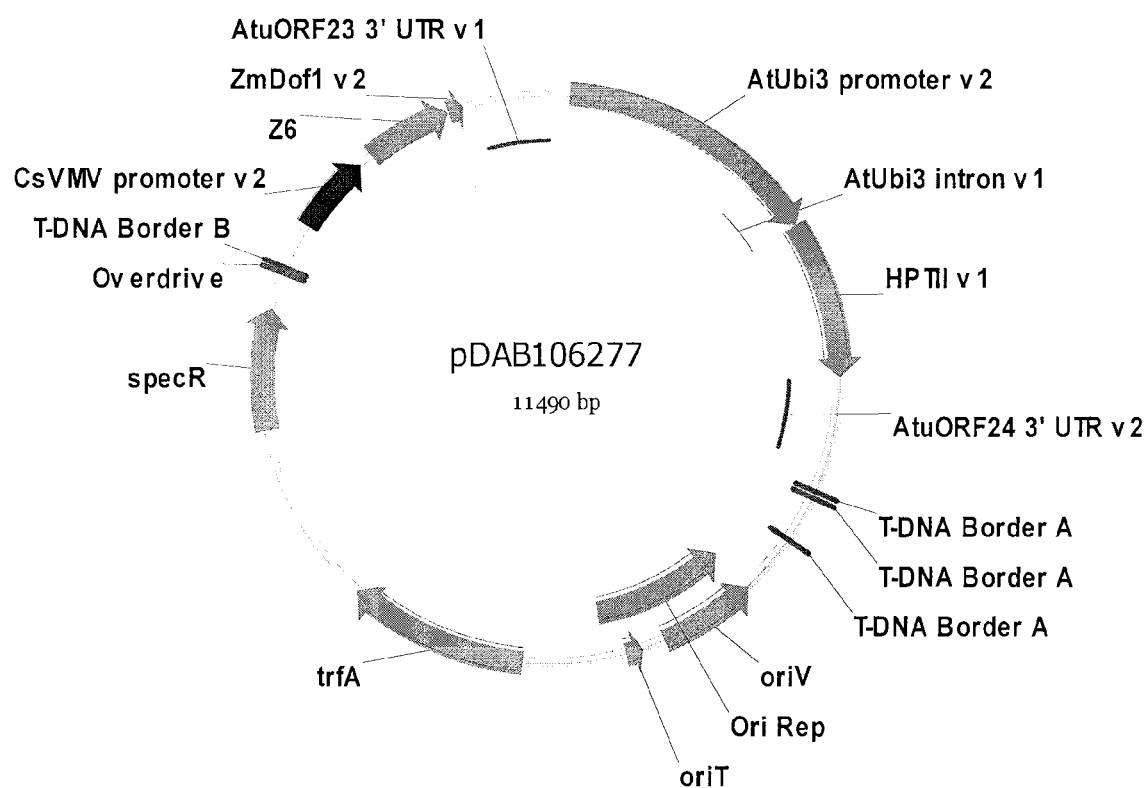
FIG. 26 includes a map of plasmid pDAB106277.
Figure 27:
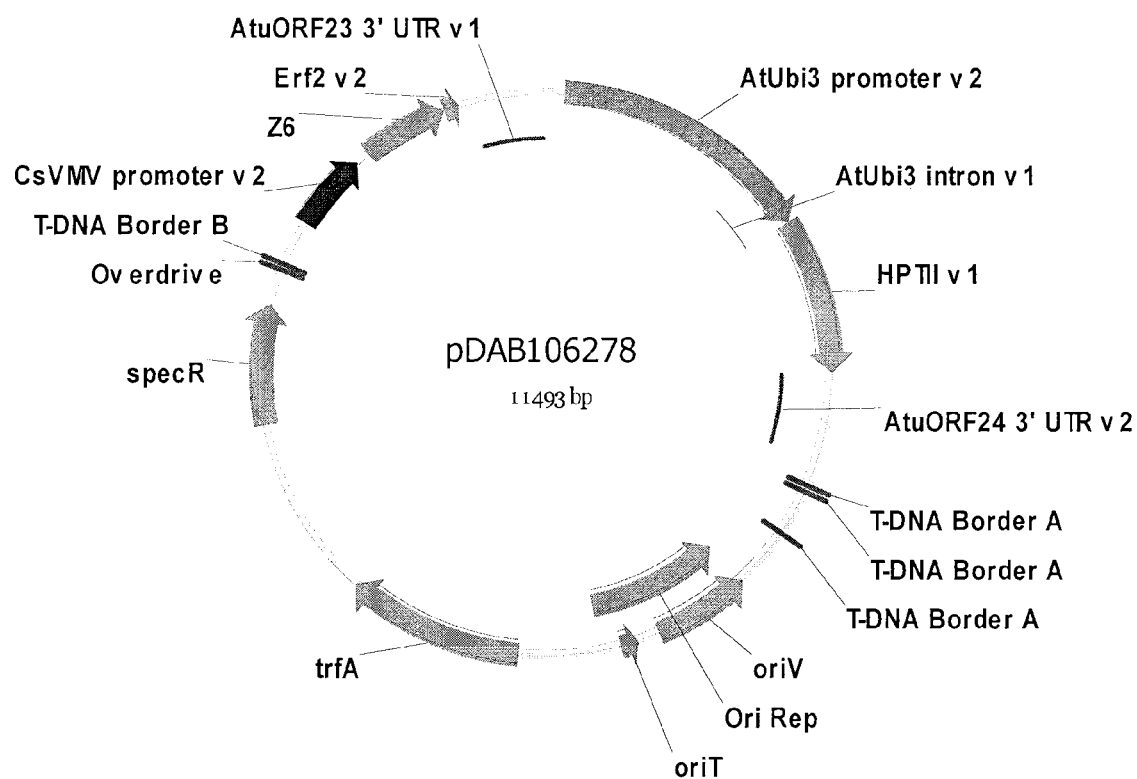
FIG. 27 includes a map of plasmid pDAB106278.
Figure 28:
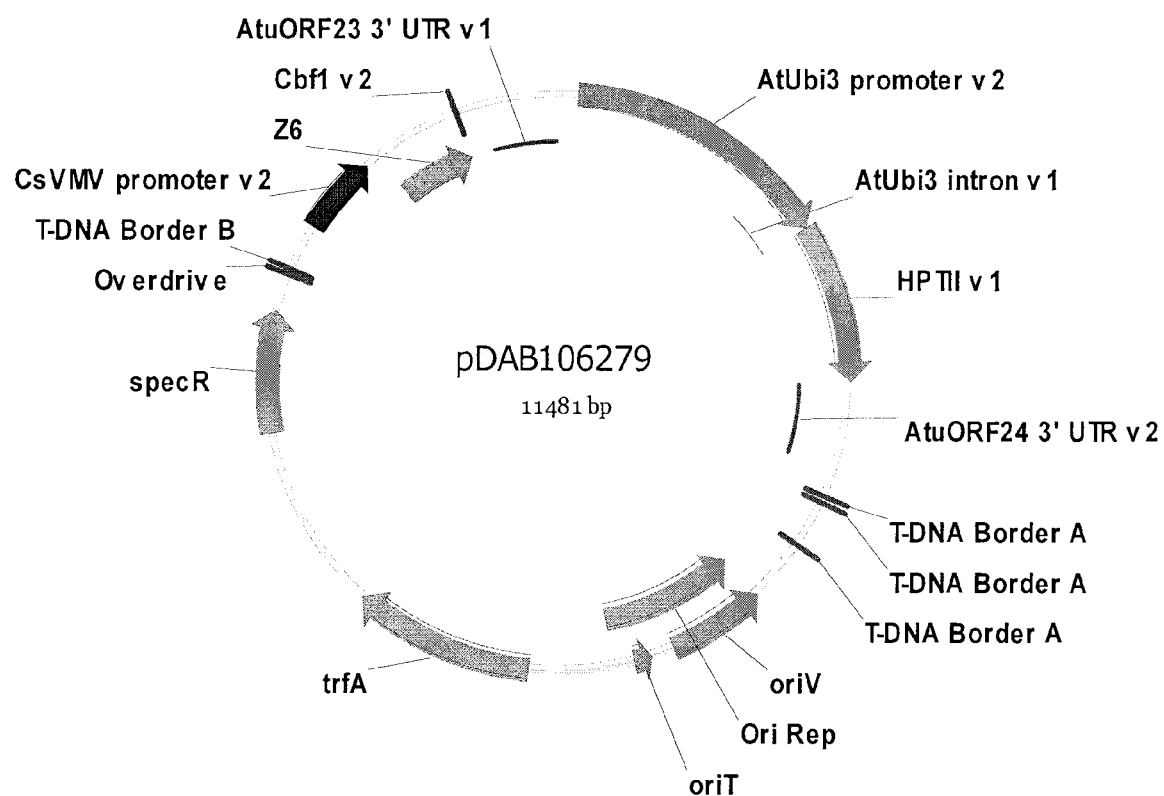
FIG. 28 includes a map of plasmid pDAB106279.

| Plant Transactivation Interaction Motif | Construct Number and Plant Transactivation Interaction Motif Sequence | | | |
|---|---|---|---|---|
| | Native | | Modified | |
| Pti4 | pDAB107881 | FIG. 13 SEQ ID NO: 81 | pDAB106273 | FIG. 22 SEQ ID NO: 88 |
| AtERF1 | pDAB107882 | FIG. 14 SEQ ID NO: 82 | pDAB106274 | FIG. 23 SEQ ID NO: 89 |
| ORCA2 | pDAB107883 | FIG. 15 SEQ ID NO: 83 | pDAB106275 | FIG. 24 SEQ ID NO: 90 |
| Dreb1a | pDAB107884 | FIG. 16 SEQ ID NO: 84 | pDAB106276 | FIG. 25 SEQ ID NO: 91 |
| Dof1 | pDAB107885 | FIG. 17 SEQ ID NO: 86 | pDAB106277 | FIG. 26 SEQ ID NO: 93 |
| ERF2 | pDAB107886 | FIG. 18 SEQ ID NO: 80 | pDAB106278 | FIG. 27 SEQ ID NO: 87 |
| Cbf1 | pDAB107887 | FIG. 19 SEQ ID NO: 85 | pDAB106279 | FIG. 28 SEQ ID NO: 92 |
| VP16 | pDAB106272 | FIG. 20 SEQ ID NO: 79 | — | — |
| Empty Vector - Zinc Finger Only (no transactivation interaction motif) | pDAB106238 | FIG. 21 | — | — |

The final binary vector was confirmed via DNA sequencing, and transformed into *A. tumefaciens* strain, LBA4404 (Invitrogen). In addition, a control vector pDAB106238 (FIG. 21), which contains the zinc finger binding domain and does not include an activator composed of the transactivation interaction motif, was included. In this construct, the zinc finger binding domain was placed under the control of the constitutive *A. tumefaciens* MAS promoter (AtuMas promoter v4; U.S. Pat. Nos. 5,001,060; 5,573,932 and 5,290,924), and terminated with the ORF23 3'UTR from *A. tumefaciens*. In addition, the vector contains the *A. thaliana* ubiquitin-3 promoter/hygromycin phosphotransferase II/*A. tumefaciens* open reading frame-24, 3' untranslated region cassette used for plant selection.

To produce plant events containing the plant ZFP-transcription activator constructs, leaf discs (1 cm²) cut from T₂ reporter tobacco plants were incubated in an overnight culture of *A. tumefaciens* strain, LBA4404 (Invitrogen, Carlsbad, Calif.), harboring one of the 16 plasmids listed in Table 2, grown to OD$_{600}$ ~1.2 nm, blotted dry on sterile filter paper, and then placed onto MS medium (Phytotechnology Labs, Shawnee Mission, Kans.) and 30 g/L sucrose with the addition of 1 mg/L indoleacetic acid and 1 mg/L benzyamino purine in 60×20 mm dishes (5 discs per dish) sealed with Nescofilm® (Karlan Research Products Corporation, Cottonwood, Ariz.). Following 48 hours of co-cultivation, leaf discs were transferred to the same medium with 250 mg/L cephotaxime and 10 mg/L hygromycin. After 3-4 weeks, plantlets were transferred to MS medium with 250 mg/L cephotaxime and 10 mg/L hygromycin in Phytalrays™ for an additional 2-3 weeks, followed by leaf harvest and gus expression analysis. A total of 20-30 plant events were generated for each of the 16 plant transcription activator constructs.

Gus Expression Analysis.

mRNA Isolation. Transgenic tobacco plant tissue was harvested from newly growing plantlets and flash frozen on dry ice in 96-well collection plates (Qiagen). RNA was then isolated using the RNEasy® 96-well extraction kit (Qiagen), according to the manufacturer's instructions. A Model 2-96A Kleco™ tissue pulverizer (Garcia Manufacturing) was used for tissue disruption.

RNA Quantification. Resulting mRNA was quantified using a NanoDrop™ 8000 spectrophotometer (Thermo Scientific, Wilmington, Del.). Each well was blanked with 4 µL RNase-free water prior to loading and quantify 4 µL of undiluted samples. mRNA concentration was estimated from NanoDrop™ 8000 software, using the standard RNA nucleic acid measurement method. mRNA was hand-diluted with RNase free water to ~83 ng/µL.

cDNA Preparation. cDNA was prepared from diluted mRNA using the Quantitect® RT kit (Qiagen, Carlsbad, Calif.), following the manufacturer's instructions. 1 µg total mRNA was used in each reaction. Upon completion, cDNA was stored at −20° C. until analysis was completed.

RT-PCR. Events selected on hygromycin were analyzed for gus gene transcript levels using two DNA hydrolysis probe assays, both of which are analogous to TaqMan® assays. Steady state levels of gus mRNA for each individual event were estimated using sequence-specific primers and probe. The mRNA was normalized using the steady state level of mRNA for an endogenous tobacco reference gene, BYEEF (Genbank Accession No. GI:927382). Assays for both genes were designed using LightCycler® Probe Design Software 2.0 (Roche Applied Science). Real time PCR for both genes was evaluated using the LightCycler® 480 system. For gus amplification, LightCycler® 480 Probes Master mix was prepared at 1× final concentration in a 10 µL volume multiplex reaction containing 0.4 µM of each primer and 0.2 µM probe. Table 3.

Figure 29:
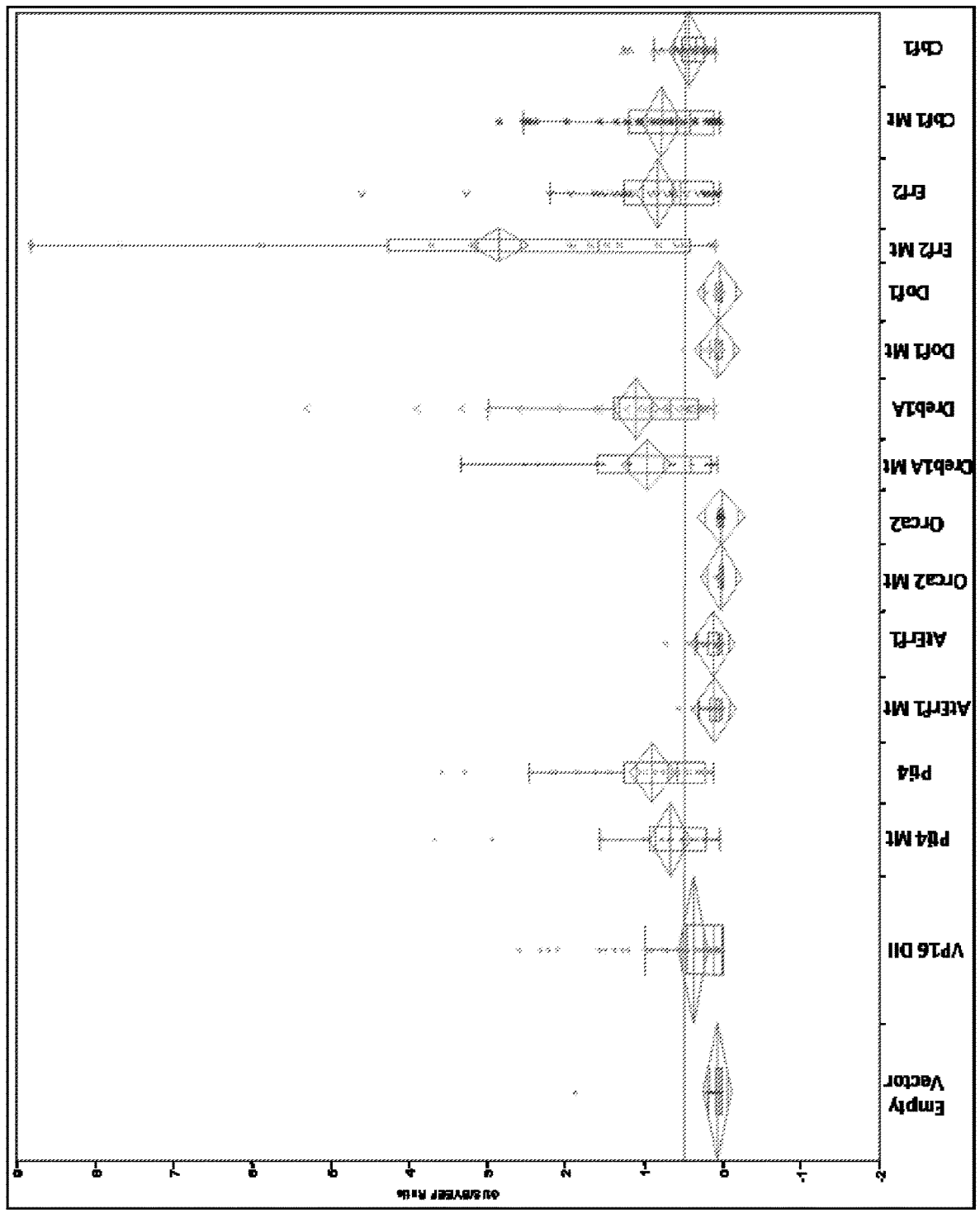
FIG. 29 includes a graphical representation of the mean and standard deviation (diamonds) and the quartiles (lines and boxes) of the gus transcript level normalized by endogenous gene expression level for the different plant transactivation interaction motif treatments. Activation of the gus reporter gene from different plant transactivation interaction motifs was compared to an empty vector control and the activation of the domain II subunit of the VP16 protein.

A two-step amplification reaction was performed with an extension at 56° C. for 40 seconds with fluorescence acquisition. All samples were run undiluted in triplicate, and the averaged Ct values were used for analysis of each sample. For BYEEF amplification, LightCycler® 480 Probes Master mix was prepared at 1× final concentration in a 10 µL volume multiplex reaction containing 0.25 µM of each primer (Table 3) and 0.1 µM UPL 119 probe (Roche Applied Science). A two-step amplification reaction was performed with an extension at 58° C. for 25 seconds with fluorescence acquisition. All samples were run diluted 1:10 in triplicate, and the averaged Ct values were used for analysis of each sample. Analysis of real time PCR data was performed using LightCycler® software using the relative quant module, and is based on the ΔΔCt method. Relative expression levels amongst the different plant transcription activator treatments were then compared. FIG. 29.

TABLE 3

Sequences of the primers and probes used in both the gus and BYEEF hydrolysis probe (HP) assays.

| Primer | Nucleotide Sequence (5'-3') | Type |
|---|---|---|
| TQGUSS | AGACAGAGTGTGATATCTACCC (SEQ ID NO: 75) | Primer |
| TQGUSA | CCATCAGCACGTTATCGAAT (SEQ ID NO: 76) | Primer |

TABLE 3-continued

Sequences of the primers and probes used in both the gus and BYEEF hydrolysis probe (HP) assays.

| Primer | Nucleotide Sequence (5'-3') | Type |
|---|---|---|
| TQGUSFQ | 6FAM-CACAAACCGTTCTACTTTACTG GCTT-BHQ1 (SEQ ID NO: 77) | 6FAM Probe |
| BYEEFU119F | AGGCTCCCACTTCAGGATG (SEQ ID NO: 78) | Primer |
| BYEEFU119R | CACGACCAACAGGGACAGTA (SEQ ID NO: 79) | Primer |

Results.

FIG. 29 shows the resulting ratio of gus transcript levels for the different plant transactivation interaction motifs, as normalized by BYEEF endogenous gene expression levels. The activation of the gus gene from the different plant transactivation interaction motifs was compared to an empty vector control, and the interaction motif of subdomain II of the VP16 transactivation domain. Several of the plant transactivation interaction motifs showed unexpectedly high levels of expression as compared to subdomain II of the VP16 transactivator. For instance, the PTI4, DREB1A, ERF2, and CBF1 plant transactivation interaction motifs expressed more gus mRNA than subdomain II of the VP16 transcription activation domain.

The levels of mRNA produced by the plant transactivation interaction motif for the modified variant (v2) as compared to the native version (v3) varied amongst the plant transactivation interaction motifs. The modified version of the ERF2 plant transactivation interaction motif produced significantly more gus mRNA than the ERF2 native sequence interaction motif. Likewise, the modified CBF1 plant transactivation interaction motif produced more mRNA than the CBF1 native sequence interaction motif. Conversely, the modifications introduced within the PTI4 and DREB1A transactivation interaction motif resulted in the production of lower gus mRNA levels, as compared to the native versions of PTI4 and DREB1A plant transactivation interaction motifs.

Example 5: Interaction Motif Function in Tobacco Containing a GAL4 Reporter Construct Tobacco Line Containing a Reporter Construct Comprised of a GAL4 Binding Domain.

Figure 30:
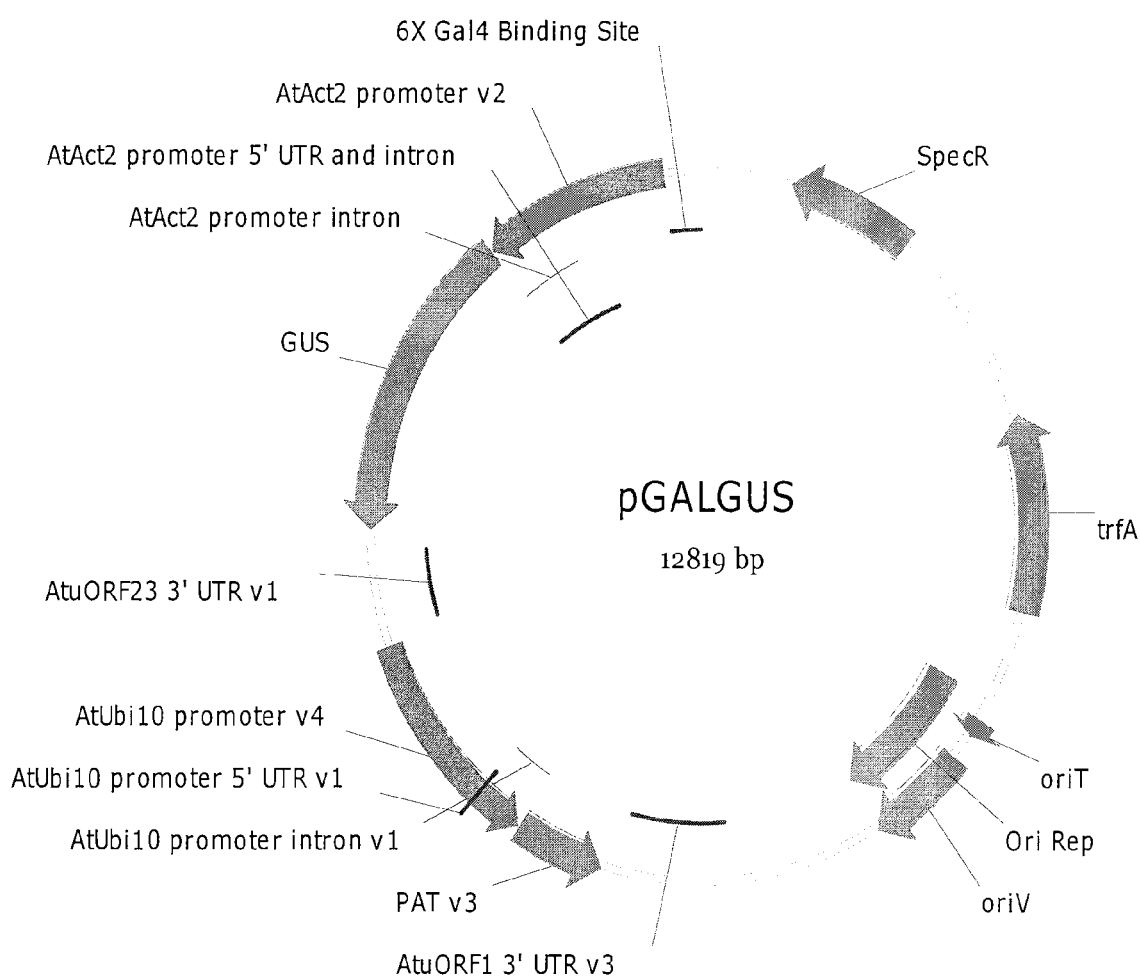
FIG. 30 includes a map of plasmid pGalGUS: Six tandem Gal4 binding sites fused to an *A. thaliana* actin-2 promoter driving a gus reporter gene are used for testing plant transactivation interaction motifs fused to the Gal4 binding protein. The binary vector also contains an *A. thaliana* ubiquitin-10 promoter driving a pat selectable marker for target reporter plant event production.

The reporter construct, pGalGUS, is built using the strategy described below. Six tandem repeats of the yeast GAL4 binding sequence and 23 bp spacer regions (as described in Baleja et al. (1997) *J. Biomol. NMR* 10:397-401) are synthesized de novo (IDT) with added SacII sites to facilitate cloning. The 6X Gal4 binding sites are mobilized on a SacII fragment, and are used to replace the Z6 binding sites from a pre-existing entry vector that is also digested with SacII. This cloning step places the GAL4 binding sites immediately upstream of the *Arabidopsis* Actin 2 promoter, which drives expression of the gus gene. The final transformation vector, pGalGUS (FIG. 30), results from a Gateway® Transformation reaction with a destination vector containing an *Arabidopsis* Ubiquitin10 promoter-pat gene expression cassette, which is used for plant selection. The final transformation vector is confirmed via sequencing, and transformed into *A. tumefaciens* strain, LBA4404 (Invitrogen).

*Agrobacterium*-Mediated Transformation of Tobacco with pGALGUS.

Transgenic reporter plants are made using the protocol described above. See "*Agrobacterium*-mediated transformation of tobacco with pDAB9897."

Copy Number and PTU Analysis of Reporter Events.

Low-complexity copy number, BASTA®-resistant transgenic plants are generated and identified based on TaqMan® copy number analysis. Of the low-complexity events, a subset displays an intact PTU, as determined by PCR analysis. These events are further analyzed via Southern blot analysis. Following Southern blot analysis, at least one single-copy, intact PTU event is selected and grown to maturity in a greenhouse, and is allowed to self-pollinate. $T_1$ seed is collected, surface sterilized, and germinated. Following zygosity screening via pat copy number analysis, homozygous $T_1$ plants are selected, grown to maturity in the greenhouse, and allowed to self-pollinate. $T_2$ seed is then collected, surface sterilized, and germinated (as described previously), and is used to generate reporter plants for activator testing.

Plant GAL4-Transcriptional Activator Expression Constructs.

Plant GAL4-transcription activator constructs containing a variant or native plant transactivation interaction motif are constructed. The plant ZFP-transcription activator expression constructs described in Example 4 ("Plant ZFP-Plant Transcription Activator Expression Constructs") are modified by inserting a GAL4 binding protein polynucleotide sequence in place of the Zinc Finger Binding Protein polynucleotide sequence. The hemicot plant-optimized GAL4 DNA binding domain polynucleotide sequence (Keegan et al. (1986) *Science* 231(4739):699-704) is inserted in place of the Zinc Finger Binding Protein polynucleotide sequence as an NcoI/BamHI fragment. Upon completion of this step, the GAL4-transcription activator construct is placed under the control of the constitutive Cassava Vein Mosaic Virus promoter, and terminated with the ORF23 3'UTR from *A. tumefaciens*. Final binary transformation vectors are completed, resulting from a Gateway® transformation with a destination vector containing an *Arabidopsis* Ubiquitin3-HptII cassette for plant selection. The final transformation vector is confirmed via sequencing, and transformed into *A. tumefaciens* strain, LBA4404 (Invitrogen).

To produce plant events containing a plant GAL4-transcription activator construct, the transient transformation protocol described in Example 4 is used. A total of 20-30 plant events are generated for each of the 16 GAL4-transcription activator constructs.

Gus Expression Analysis.

Events selected on hygromycin are analyzed for gus gene transcript levels using two DNA hydrolysis probe assays. Steady state levels of gus mRNA for each individual event are estimated using sequence specific primers and a probe. The mRNA for each event is normalized using the steady state level of mRNA for an endogenous tobacco reference gene, e.g., BYEEF. Assays for both genes are designed using the protocol described in Example 4. Analysis of real time PCR data is performed using LightCycler® software using the relative quant module, and is based on the ΔΔCt method. Relative expression levels for the different activator constructs are compared. The results indicate that plant transactivation interaction motifs and engineered variants of these plant transactivation interaction motifs can be used as transcriptional activators, and can be fused with a GAL4 binding protein for transcriptional activation of a gene.

Example 6: Interaction Motif Function in Tobacco Containing a TAL Reporter Construct Tobacco Line Containing a Reporter Construct Comprised of a TAL Binding Domain.

Figure 31:
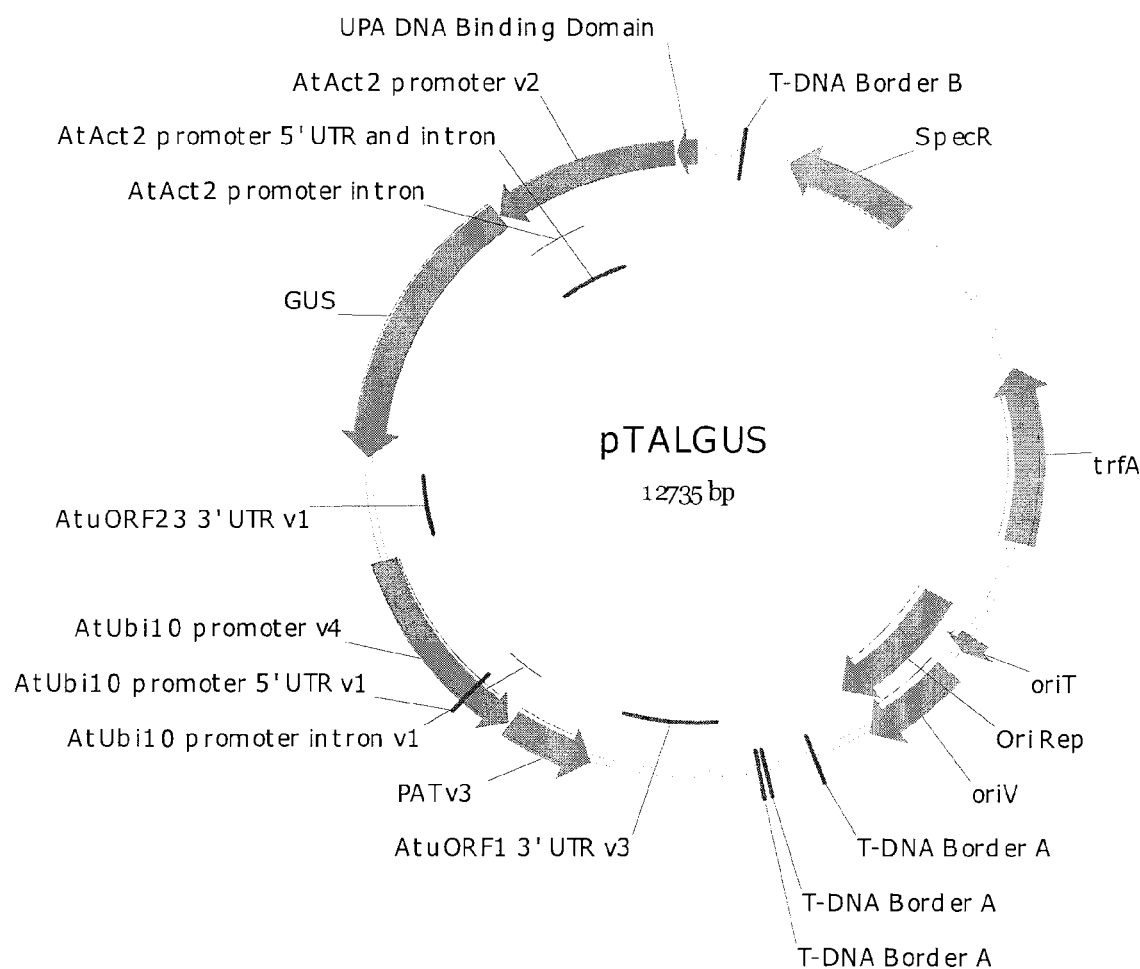
FIG. 31 includes a map of plasmid pTALGUS: Eight tandem UPA-Box consensus binding sites fused to an *A. thaliana* actin-2 promoter driving a gus reporter gene are used for testing plant transactivation interaction motifs fused to the TAL binding protein. The binary vector also contains an *A. thaliana* ubiquitin-10 promoter driving a pat selectable marker for target reporter plant event production.

The reporter construct, pTalGUS, is built using the strategy described below. Eight tandem repeats sequences (TATATAAACCTNNCCCTCT (SEQ ID NO:99)) taken from the consensus binding sequence of AVRBS3-inducible genes, and termed the UPA DNA binding domain (Kay et al. (2009) *Plant J.* 59(6):859-71), are synthesized de novo (IDT) with added SacII sites to facilitate cloning. The 8× UPA binding sites are mobilized on a SacII fragment, and are used to replace the Z6 binding sites from a pre-existing entry vector which is also digested with SacII. This cloning step places the UPA binding sites immediately upstream of the *Arabidopsis Actin* 2 promoter, which drives expression of the gus gene. The final transformation vector, pTalGUS (FIG. 31), results from a Gateway® Transformation reaction with a destination vector containing an *A. thaliana* Ubiquitin10 promoter/pat gene expression cassette, which is used for plant selection. The final transformation vector is confirmed via sequencing and transformed into *A. tumefaciens* strain, LBA4404 (Invitrogen).

Agrobacterium-Mediated Transformation of Tobacco with pTALGUS.

Transgenic reporter plants are made using the protocol described above. See "*Agrobacterium*-mediated transformation of tobacco with pDAB9897."

Copy Number and PTU Analysis of Reporter Events.

Low-complexity copy number, BASTA®-resistant, transgenic plants are generated and identified utilizing a TaqMan® copy number analysis. Of the low-complexity events, a subset displays an intact PTU, as determined by PCR analysis. These events are further analyzed via Southern blot analysis. Following Southern blot analysis, at least 1 single-copy, intact PTU event is selected and grown to maturity in a greenhouse, and is allowed to self-pollinate. $T_1$ seed is collected, surface sterilized, and germinated. Following zygosity screening via pat copy number analysis, homozygous $T_1$ plants are selected, grown to maturity in the greenhouse, and allowed to self-pollinate. $T_2$ seed is then collected, surface sterilized, and germinated (as described previously), and is used to generate reporter plants for activator testing.

Plant TAL-Transcriptional Activator Expression Constructs.

Plant TAL-transcription activator constructs containing a variant or native plant transactivation interaction motif are constructed. The plant ZFP-transcription activator expression constructs described in Example 4 are modified by inserting a TAL binding protein polynucleotide sequence in place of the Zinc Finger Binding Protein polynucleotide sequence. The 17.5 TAL repeats which are needed for DNA binding are synthesized de novo, and fused to a *Zea mays* Opaque-2 nuclear localization sequence (Van Eenennaam et al. (2004) *Metabolic Engineering* 6:101-8). The sequence of each domain utilizes different amino acids at the variable residues (12 and 13 position) to dictate DNA binding, as predicted for the UPA-box consensus sequence. Boch et al. (2009) *Science* 326(5959):1509-12. The hemicot plant-optimized TAL DNA binding domain polynucleotide sequence is inserted in place of the Zinc Finger Binding Protein polynucleotide sequence as an NcoI/BamHI fragment. Upon completion of this step, the TAL-transcription activator construct is placed under the control of the constitutive Cassava Vein Mosaic Virus promoter, and terminated with the ORF23 3'UTR from *A. tumefaciens*. Final transformation vectors are completed from a Gateway® transformation with a destination vector containing an *Arabidopsis* Ubiquitin 3-HptII cassette for plant selection. The final transformation vector is confirmed via sequencing and transformed into *A. tumefaciens* strain, LBA4404 (Invitrogen).

To produce plant events containing a plant TAL-transcription activator construct, the transient transformation protocol described in Example 4 is used. A total of 20-30 plant events are generated for each of the 16 TAL-transcription activator constructs.

Gus Expression Analysis.

Events selected on hygromycin are analyzed for gus gene transcript levels using two DNA hydrolysis probe assays. Steady state levels of gus mRNA for each individual event are estimated using sequence specific primers and a probe. The mRNA is normalized using the steady state level of mRNA for an endogenous tobacco reference gene, e.g., BYEEF. Assays for both genes are designed using the protocol described in Example 4. Analysis of real time PCR data is performed using LightCycler® software using the relative quant module, and is based on the ΔΔCt method. Relative expression levels for the different activator constructs are compared.

SEQUENCE LISTING

```
<160> NUMBER OF SEQ ID NOS: 127

<210> SEQ ID NO 1
<211> LENGTH: 34
<212> TYPE: PRT
<213> ORGANISM: herpes simplex virus

<400> SEQUENCE: 1

Gly Met Thr His Asp Pro Val Ser Tyr Gly Ala Leu Asp Val Asp
1               5                   10                  15

Phe Glu Phe Glu Gln Met Phe Thr Asp Ala Leu Gly Ile Asp Asp Phe
            20                  25                  30

Gly Gly
```

<210> SEQ ID NO 2
<211> LENGTH: 33
<212> TYPE: PRT
<213> ORGANISM: Arabidopsis thaliana

<400> SEQUENCE: 2

Asn Asp Ser Glu Asp Met Leu Val Tyr Gly Leu Leu Lys Asp Ala Phe
1               5                   10                  15

His Phe Asp Thr Ser Ser Ser Asp Leu Ser Cys Leu Phe Asp Phe Pro
            20                  25                  30

Ala

<210> SEQ ID NO 3
<211> LENGTH: 41
<212> TYPE: PRT
<213> ORGANISM: Solanum tuberosum

<400> SEQUENCE: 3

Cys Leu Thr Glu Thr Trp Gly Asp Leu Pro Lys Val Asp Asp Ser
1               5                   10                  15

Glu Asp Met Val Ile Tyr Gly Leu Leu Lys Asp Ala Leu Ser Val Gly
            20                  25                  30

Trp Ser Pro Phe Ser Phe Thr Ala Gly
        35                  40

<210> SEQ ID NO 4
<211> LENGTH: 32
<212> TYPE: PRT
<213> ORGANISM: Arabidopsis thaliana

<400> SEQUENCE: 4

Cys Phe Thr Glu Ser Trp Gly Asp Leu Pro Lys Glu Asn Asp Ser
1               5                   10                  15

Glu Asp Met Leu Val Tyr Gly Ile Leu Asn Asp Ala Phe His Gly Gly
            20                  25                  30

<210> SEQ ID NO 5
<211> LENGTH: 36
<212> TYPE: PRT
<213> ORGANISM: Catharanthus roseus

<400> SEQUENCE: 5

Phe Asn Glu Asn Cys Glu Glu Ile Ile Ser Pro Asn Tyr Ala Ser Glu
1               5                   10                  15

Asp Leu Ser Asp Ile Ile Leu Thr Asp Ile Phe Lys Asp Gln Asp Asn
            20                  25                  30

Tyr Glu Asp Glu
        35

<210> SEQ ID NO 6
<211> LENGTH: 43
<212> TYPE: PRT
<213> ORGANISM: Arabidopsis thaliana

<400> SEQUENCE: 6

Gly Phe Asp Met Glu Glu Thr Leu Val Glu Ala Ile Tyr Thr Ala Glu
1               5                   10                  15

Gln Ser Glu Asn Ala Phe Tyr Met His Asp Glu Ala Phe Glu Met
            20                  25                  30

Pro Ser Leu Leu Ala Asn Met Ala Glu Gly Met

<210> SEQ ID NO 7
<211> LENGTH: 27
<212> TYPE: PRT
<213> ORGANISM: Arabidopsis thaliana

<400> SEQUENCE: 7

Glu Gln Ser Glu Gly Ala Phe Tyr Met Asp Glu Glu Thr Met Phe Gly
1               5                   10                  15

Met Pro Thr Leu Leu Asp Asn Met Ala Glu Gly
            20                  25

<210> SEQ ID NO 8
<211> LENGTH: 33
<212> TYPE: PRT
<213> ORGANISM: Zea mays

<400> SEQUENCE: 8

Ser Ala Gly Lys Ala Val Leu Asp Asp Glu Asp Ser Phe Val Trp Pro
1               5                   10                  15

Ala Ala Ser Phe Asp Met Gly Ala Cys Trp Ala Gly Ala Gly Phe Ala
            20                  25                  30

Asp

<210> SEQ ID NO 9
<211> LENGTH: 11
<212> TYPE: PRT
<213> ORGANISM: herpes simplex virus

<400> SEQUENCE: 9

Asp Asp Phe Glu Phe Glu Gln Met Phe Thr Asp
1               5                   10

<210> SEQ ID NO 10
<211> LENGTH: 11
<212> TYPE: PRT
<213> ORGANISM: Arabidopsis thaliana

<400> SEQUENCE: 10

Asp Ala Phe His Phe Asp Thr Ser Ser Ser Asp
1               5                   10

<210> SEQ ID NO 11
<211> LENGTH: 14
<212> TYPE: PRT
<213> ORGANISM: Solanum tuberosum

<400> SEQUENCE: 11

Asp Asp Ser Glu Asp Met Val Ile Tyr Gly Leu Leu Lys Asp
1               5                   10

<210> SEQ ID NO 12
<211> LENGTH: 9
<212> TYPE: PRT
<213> ORGANISM: Arabidopsis thaliana

<400> SEQUENCE: 12

Glu Asn Asp Ser Glu Asp Met Leu Val
1               5

<210> SEQ ID NO 13
<211> LENGTH: 10

```
<212> TYPE: PRT
<213> ORGANISM: Catharanthus roseus

<400> SEQUENCE: 13

Glu Asp Leu Ser Asp Ile Ile Leu Thr Asp
1               5                   10

<210> SEQ ID NO 14
<211> LENGTH: 15
<212> TYPE: PRT
<213> ORGANISM: Arabidopsis thaliana

<400> SEQUENCE: 14

Glu Asn Ala Phe Tyr Met His Asp Glu Ala Met Phe Glu Met Pro
1               5                   10                  15

<210> SEQ ID NO 15
<211> LENGTH: 9
<212> TYPE: PRT
<213> ORGANISM: Arabidopsis thaliana

<400> SEQUENCE: 15

Asp Glu Glu Thr Met Phe Gly Met Pro
1               5

<210> SEQ ID NO 16
<211> LENGTH: 12
<212> TYPE: PRT
<213> ORGANISM: Zea mays

<400> SEQUENCE: 16

Glu Asp Ser Phe Val Trp Pro Ala Ala Ser Phe Asp
1               5                   10

<210> SEQ ID NO 17
<211> LENGTH: 11
<212> TYPE: PRT
<213> ORGANISM: Artificial
<220> FEATURE:
<223> OTHER INFORMATION: Variant TAD interaction motif vERF2_1
<220> FEATURE:
<221> NAME/KEY: MISC_FEATURE
<222> LOCATION: (4)..(4)
<223> OTHER INFORMATION: Xaa is Glu or His
<220> FEATURE:
<221> NAME/KEY: MISC_FEATURE
<222> LOCATION: (7)..(7)
<223> OTHER INFORMATION: Xaa is Gln or Thr
<220> FEATURE:
<221> NAME/KEY: MISC_FEATURE
<222> LOCATION: (8)..(8)
<223> OTHER INFORMATION: Xaa is Met or Ser
<220> FEATURE:
<221> NAME/KEY: MISC_FEATURE
<222> LOCATION: (10)..(10)
<223> OTHER INFORMATION: Xaa is Thr or Ser

<400> SEQUENCE: 17

Asp Asp Phe Xaa Phe Asp Xaa Xaa Phe Xaa Asp
1               5                   10

<210> SEQ ID NO 18
<211> LENGTH: 11
<212> TYPE: PRT
<213> ORGANISM: Artificial
<220> FEATURE:
<223> OTHER INFORMATION: Variant TAD interaction motif vERF2_2
<220> FEATURE:
<221> NAME/KEY: MISC_FEATURE
```

```
<222> LOCATION: (2)..(2)
<223> OTHER INFORMATION: Xaa is Asp or Ala
<220> FEATURE:
<221> NAME/KEY: MISC_FEATURE
<222> LOCATION: (4)..(4)
<223> OTHER INFORMATION: Xaa is Glu or His
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Gln or Thr
<220> FEATURE:
<221> NAME/KEY: MISC_FEATURE
<222> LOCATION: (8)..(8)
<223> OTHER INFORMATION: Xaa is Met or Ser
<220> FEATURE:
<221> NAME/KEY: MISC_FEATURE
<222> LOCATION: (10)..(10)
<223> OTHER INFORMATION: Xaa is Thr or Ser

<400> SEQUENCE: 18

Asp Xaa Phe Xaa Phe Xaa Xaa Xaa Phe Xaa Asp
1               5                   10

<210> SEQ ID NO 19
<211> LENGTH: 11
<212> TYPE: PRT
<213> ORGANISM: Artificial
<220> FEATURE:
<223> OTHER INFORMATION: Variant TAD interaction motif vERF2_3
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (4)..(4)
<223> OTHER INFORMATION: Xaa is Asp, Glu, or His
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Gln or Thr
<220> FEATURE:
<221> NAME/KEY: MISC_FEATURE
<222> LOCATION: (8)..(8)
<223> OTHER INFORMATION: Xaa is Ala, Val, Ile, Leu, or Met
<220> FEATURE:
<221> NAME/KEY: MISC_FEATURE
<222> LOCATION: (9)..(9)
<223> OTHER INFORMATION: Xaa is Phe, Trp, or Tyr
<220> FEATURE:
<221> NAME/KEY: MISC_FEATURE
<222> LOCATION: (10)..(10)
<223> OTHER INFORMATION: Xaa is Ser, Thr, Asn, Gln, Cys, Gly, or Pro

<400> SEQUENCE: 19

Asp Xaa Phe Xaa Phe Xaa Xaa Xaa Xaa Xaa Asp
1               5                   10

<210> SEQ ID NO 20
<211> LENGTH: 11
<212> TYPE: PRT
<213> ORGANISM: Artificial
<220> FEATURE:
<223> OTHER INFORMATION: Variant TAD interaction motif vERF2_4
<220> FEATURE:
<221> NAME/KEY: MISC_FEATURE
<222> LOCATION: (2)..(2)
```

```
<223> OTHER INFORMATION: Xaa is Asp, or Glu
<220> FEATURE:
<221> NAME/KEY: MISC_FEATURE
<222> LOCATION: (4)..(4)
<223> OTHER INFORMATION: Xaa is His, Arg, Lys, Asp, or Glu
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Ser, Thr, Asn, Gln, Cys, Gly, Tyr, or
      Pro
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (10)..(10)
<223> OTHER INFORMATION: Xaa is Ser, Thr, Asn, Gln, Cys, Gly, Tyr, or
      Pro

<400> SEQUENCE: 20

Asp Xaa Phe Xaa Phe Xaa Xaa Xaa Xaa Xaa Asp
1               5                   10

<210> SEQ ID NO 21
<211> LENGTH: 11
<212> TYPE: PRT
<213> ORGANISM: Artificial
<220> FEATURE:
<223> OTHER INFORMATION: Variant TAD interaction motif vERF2_5
<220> FEATURE:
<221> NAME/KEY: MISC_FEATURE
<222> LOCATION: (2)..(2)
<223> OTHER INFORMATION: Xaa is Ala, Asp, or Glu
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, Trp,
      or Ser
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, Trp,
      or Ser
<220> FEATURE:
<221> NAME/KEY: MISC_FEATURE
<222> LOCATION: (10)..(10)
<223> OTHER INFORMATION: Xaa is any amino acid

<400> SEQUENCE: 21

Asp Xaa Phe Xaa Phe Xaa Xaa Xaa Xaa Xaa Asp
1               5                   10
```

```
<210> SEQ ID NO 22
<211> LENGTH: 11
<212> TYPE: PRT
<213> ORGANISM: Artificial
<220> FEATURE:
<223> OTHER INFORMATION: Variant TAD interaction motif vERF2_6

<400> SEQUENCE: 22

Asp Asp Phe His Phe Glu Thr Met Phe Ser Asp
1               5                   10

<210> SEQ ID NO 23
<211> LENGTH: 14
<212> TYPE: PRT
<213> ORGANISM: Artificial
<220> FEATURE:
<223> OTHER INFORMATION: Variant TAD interaction motif vPTI_1
<220> FEATURE:
<221> NAME/KEY: MISC_FEATURE
<222> LOCATION: (3)..(3)
<223> OTHER INFORMATION: Xaa is Phe or Ser
<220> FEATURE:
<221> NAME/KEY: MISC_FEATURE
<222> LOCATION: (5)..(5)
<223> OTHER INFORMATION: Xaa is Asp or Glu
<220> FEATURE:
<221> NAME/KEY: MISC_FEATURE
<222> LOCATION: (6)..(6)
<223> OTHER INFORMATION: Xaa is Gln or Met
<220> FEATURE:
<221> NAME/KEY: MISC_FEATURE
<222> LOCATION: (7)..(7)
<223> OTHER INFORMATION: Xaa is Met or Val
<220> FEATURE:
<221> NAME/KEY: MISC_FEATURE
<222> LOCATION: (9)..(9)
<223> OTHER INFORMATION: Xaa is Phe or Tyr
<220> FEATURE:
<221> NAME/KEY: MISC_FEATURE
<222> LOCATION: (11)..(11)
<223> OTHER INFORMATION: Xaa is Thr or Leu

<400> SEQUENCE: 23

Asp Asp Xaa Glu Xaa Xaa Xaa Ile Xaa Gly Xaa Leu Lys Asp
1               5                   10

<210> SEQ ID NO 24
<211> LENGTH: 14
<212> TYPE: PRT
<213> ORGANISM: Artificial
<220> FEATURE:
<223> OTHER INFORMATION: Variant TAD interaction motif vPTI4_2
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Asp or Glu
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Ala, Val, Ile, Leu, or Met
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
```

```
<223> OTHER INFORMATION: Xaa is Phe, Trp, or Tyr
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid

<400> SEQUENCE: 24

Asp Asp Xaa Glu Xaa Xaa Xaa Xaa Xaa Xaa Xaa Xaa Asp
1               5                   10

<210> SEQ ID NO 25
<211> LENGTH: 11
<212> TYPE: PRT
<213> ORGANISM: Artificial
<220> FEATURE:
<223> OTHER INFORMATION: Variant TAD interaction motif vPTI4_3
<220> FEATURE:
<221> NAME/KEY: MISC_FEATURE
<222> LOCATION: (3)..(3)
<223> OTHER INFORMATION: Xaa is Phe or Ser
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Gln or Met
<220> FEATURE:
<221> NAME/KEY: MISC_FEATURE
<222> LOCATION: (8)..(8)
<223> OTHER INFORMATION: Xaa is Met or Val
<220> FEATURE:
<221> NAME/KEY: MISC_FEATURE
<222> LOCATION: (9)..(9)
<223> OTHER INFORMATION: Xaa is Phe or Tyr
<220> FEATURE:
<221> NAME/KEY: MISC_FEATURE
<222> LOCATION: (10)..(10)
<223> OTHER INFORMATION: Xaa is Thr or Leu

<400> SEQUENCE: 25

Asp Asp Xaa Glu Phe Xaa Xaa Xaa Xaa Xaa Asp
1               5                   10

<210> SEQ ID NO 26
<211> LENGTH: 11
<212> TYPE: PRT
<213> ORGANISM: Artificial
<220> FEATURE:
<223> OTHER INFORMATION: Variant TAD interaction motif vPTI4_4
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (6)..(6)
<223> OTHER INFORMATION: Xaa is Asp or Glu
```

```
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ala, Val, Ile, Leu, or Met
<220> FEATURE:
<221> NAME/KEY: MISC_FEATURE
<222> LOCATION: (9)..(9)
<223> OTHER INFORMATION: Xaa is Phe, Trp, or Tyr
<220> FEATURE:
<221> NAME/KEY: MISC_FEATURE
<222> LOCATION: (10)..(10)
<223> OTHER INFORMATION: Xaa is any amino acid

<400> SEQUENCE: 26

Asp Asp Xaa Glu Xaa Xaa Xaa Xaa Xaa Xaa Asp
1               5                   10

<210> SEQ ID NO 27
<211> LENGTH: 11
<212> TYPE: PRT
<213> ORGANISM: Artificial
<220> FEATURE:
<223> OTHER INFORMATION: Variant TAD interaction motif vPTI4_5
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Ala, Val, Ile, Leu, Met, Phe, Tyr, or
     Trp
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, or
     Trp
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, or
     Trp
<220> FEATURE:
<221> NAME/KEY: MISC_FEATURE
<222> LOCATION: (10)..(10)
<223> OTHER INFORMATION: Xaa is any amino acid

<400> SEQUENCE: 27

Asp Asp Xaa Glu Xaa Xaa Xaa Xaa Xaa Xaa Asp
1               5                   10

<210> SEQ ID NO 28
<211> LENGTH: 11
<212> TYPE: PRT
<213> ORGANISM: Artificial
<220> FEATURE:
<223> OTHER INFORMATION: Variant TAD interaction motif vPTI4_6

<400> SEQUENCE: 28

Asp Asp Phe Glu Phe Glu Met Met Phe Thr Asp
1               5                   10
```

```
<210> SEQ ID NO 29
<211> LENGTH: 9
<212> TYPE: PRT
<213> ORGANISM: Artificial
<220> FEATURE:
<223> OTHER INFORMATION: Variant TAD interaction motif vAtERF1_1
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (4)..(4)
<223> OTHER INFORMATION: Xaa is Phe or Ser
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Phe or Leu
<220> FEATURE:
<221> NAME/KEY: MISC_FEATURE
<222> LOCATION: (9)..(9)
<223> OTHER INFORMATION: Xaa is Thr or Val

<400> SEQUENCE: 29

Xaa Asn Asp Xaa Glu Xaa Met Xaa Xaa
1               5

<210> SEQ ID NO 30
<211> LENGTH: 9
<212> TYPE: PRT
<213> ORGANISM: Artificial
<220> FEATURE:
<223> OTHER INFORMATION: Variant TAD interaction motif vAtERF1_2
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (9)..(9)
<223> OTHER INFORMATION: Xaa is any amino acid

<400> SEQUENCE: 30

Xaa Xaa Asp Xaa Glu Xaa Met Xaa Xaa
1               5

<210> SEQ ID NO 31
<211> LENGTH: 11
<212> TYPE: PRT
<213> ORGANISM: Artificial
<220> FEATURE:
<223> OTHER INFORMATION: Variant TAD interaction motif vAtERF1_3
<220> FEATURE:
```

<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is Phe or Ser
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (9)..(9)
<223> OTHER INFORMATION: Xaa is Phe or Leu
<220> FEATURE:
<221> NAME/KEY: MISC_FEATURE
<222> LOCATION: (10)..(10)
<223> OTHER INFORMATION: Xaa is Thr or Val

<400> SEQUENCE: 31

Xaa Asp Xaa Glu Phe Xaa Gln Met Xaa Xaa Asp
1               5                   10

<210> SEQ ID NO 32
<211> LENGTH: 11
<212> TYPE: PRT
<213> ORGANISM: Artificial
<220> FEATURE:
<223> OTHER INFORMATION: Variant TAD interaction motif vAtERF1_4
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Ser, Thr, Asn, Gln, Cys, Gly, Tyr, or
      Pro
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Asp or Glu

<400> SEQUENCE: 32

Xaa Asp Xaa Glu Xaa Xaa Xaa Met Xaa Xaa Xaa
1               5                   10

<210> SEQ ID NO 33
<211> LENGTH: 11
<212> TYPE: PRT
<213> ORGANISM: Artificial
<220> FEATURE:
<223> OTHER INFORMATION: Variant TAD interaction motif vAtERF1_5

```
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (6)..(6)
<223> OTHER INFORMATION: Xaa is Asp, Glu, His, Arg, or Lys
<220> FEATURE:
<221> NAME/KEY: MISC_FEATURE
<222> LOCATION: (7)..(7)
<223> OTHER INFORMATION: Xaa is Ser, Thr, Asn, Gln, Cys, Gly, Tyr, or
      Pro
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Asp or Glu

<400> SEQUENCE: 33

Xaa Asp Xaa Glu Xaa Xaa Xaa Met Xaa Xaa Xaa
1               5                   10

<210> SEQ ID NO 34
<211> LENGTH: 11
<212> TYPE: PRT
<213> ORGANISM: Artificial
<220> FEATURE:
<223> OTHER INFORMATION: Variant TAD interaction motif vAtERF1_6

<400> SEQUENCE: 34

Glu Asn Asp Phe Glu Phe Glu Met Phe Thr Asp
1               5                   10

<210> SEQ ID NO 35
<211> LENGTH: 10
<212> TYPE: PRT
<213> ORGANISM: Artificial
<220> FEATURE:
<223> OTHER INFORMATION: Variant TAD interaction motif vORCA2_1
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is Phe or Leu
<220> FEATURE:
<221> NAME/KEY: MISC_FEATURE
<222> LOCATION: (4)..(4)
<223> OTHER INFORMATION: Xaa is Glu or Ser
<220> FEATURE:
<221> NAME/KEY: MISC_FEATURE
<222> LOCATION: (5)..(5)
<223> OTHER INFORMATION: Xaa is Phe or Asp
<220> FEATURE:
<221> NAME/KEY: MISC_FEATURE
```

```
<222> LOCATION: (6)..(6)
<223> OTHER INFORMATION: Xaa is Glu or Ile
<220> FEATURE:
<221> NAME/KEY: MISC_FEATURE
<222> LOCATION: (7)..(7)
<223> OTHER INFORMATION: Xaa is Met or Ile
<220> FEATURE:
<221> NAME/KEY: MISC_FEATURE
<222> LOCATION: (8)..(8)
<223> OTHER INFORMATION: Xaa is Phe or Leu

<400> SEQUENCE: 35

Xaa Asp Xaa Xaa Xaa Xaa Xaa Xaa Thr Asp
1               5                   10

<210> SEQ ID NO 36
<211> LENGTH: 10
<212> TYPE: PRT
<213> ORGANISM: Artificial
<220> FEATURE:
<223> OTHER INFORMATION: Variant TAD interaction motif vORCA2_2
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, or
      Trp

<400> SEQUENCE: 36

Xaa Asp Xaa Xaa Xaa Xaa Xaa Xaa Thr Asp
1               5                   10

<210> SEQ ID NO 37
<211> LENGTH: 11
<212> TYPE: PRT
<213> ORGANISM: Artificial
<220> FEATURE:
<223> OTHER INFORMATION: Variant TAD interaction motif vORCA2_3
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is Phe or Leu
<220> FEATURE:
<221> NAME/KEY: MISC_FEATURE
<222> LOCATION: (4)..(4)
<223> OTHER INFORMATION: Xaa is Glu or Ser
```

```
<220> FEATURE:
<221> NAME/KEY: MISC_FEATURE
<222> LOCATION: (5)..(5)
<223> OTHER INFORMATION: Xaa is Phe or Asp
<220> FEATURE:
<221> NAME/KEY: MISC_FEATURE
<222> LOCATION: (6)..(6)
<223> OTHER INFORMATION: Xaa is Glu or Ile
<220> FEATURE:
<221> NAME/KEY: MISC_FEATURE
<222> LOCATION: (8)..(8)
<223> OTHER INFORMATION: Xaa is Met or Ile
<220> FEATURE:
<221> NAME/KEY: MISC_FEATURE
<222> LOCATION: (9)..(9)
<223> OTHER INFORMATION: Xaa is Phe or Leu

<400> SEQUENCE: 37

Xaa Asp Xaa Xaa Xaa Xaa Gln Xaa Xaa Thr Asp
1               5                   10

<210> SEQ ID NO 38
<211> LENGTH: 11
<212> TYPE: PRT
<213> ORGANISM: Artificial
<220> FEATURE:
<223> OTHER INFORMATION: Variant TAD interaction motif vORCA2_4
<220> FEATURE:
<221> NAME/KEY: MISC_FEATURE
<222> LOCATION: (1)..(1)
<223> OTHER INFORMATION: Xaa is His, Arg, Lys, Asp, or Glu
<220> FEATURE:
<221> NAME/KEY: MISC_FEATURE
<222> LOCATION: (3)..(3)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (4)..(4)
<223> OTHER INFORMATION: Xaa is Ser, Thr, Asn, Gln, Cys, Gly, Pro, Arg,
      His, Lys, Asp, or Glu
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Ser, Thr, Asn, Gln, Cys, Gly, Pro, Arg,
      His, Lys, Asp, or Glu
<220> FEATURE:
<221> NAME/KEY: MISC_FEATURE
<222> LOCATION: (8)..(8)
<223> OTHER INFORMATION: Xaa is Ala, Val, Ile, Leu, or Met
<220> FEATURE:
<221> NAME/KEY: MISC_FEATURE
<222> LOCATION: (9)..(9)
<223> OTHER INFORMATION: Xaa is Phe, Trp, or Tyr

<400> SEQUENCE: 38

Xaa Asp Xaa Xaa Xaa Xaa Xaa Xaa Xaa Thr Asp
1               5                   10

<210> SEQ ID NO 39
<211> LENGTH: 11
<212> TYPE: PRT
<213> ORGANISM: Artificial
<220> FEATURE:
<223> OTHER INFORMATION: Variant TAD interaction motif vORCA2_5
<220> FEATURE:
<221> NAME/KEY: MISC_FEATURE
```

```
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, or
      Trp

<400> SEQUENCE: 39

Xaa Asp Xaa Xaa Xaa Xaa Xaa Xaa Xaa Thr Asp
1               5                   10

<210> SEQ ID NO 40
<211> LENGTH: 10
<212> TYPE: PRT
<213> ORGANISM: Artificial
<220> FEATURE:
<223> OTHER INFORMATION: Variant TAD interaction motif vORCA2_6

<400> SEQUENCE: 40

Glu Asp Phe Asp Leu Glu Met Leu Thr Asp
1               5                   10

<210> SEQ ID NO 41
<211> LENGTH: 15
<212> TYPE: PRT
<213> ORGANISM: Artificial
<220> FEATURE:
<223> OTHER INFORMATION: Variant TAD interaction motif vDREB1A_1
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (10)..(10)
<223> OTHER INFORMATION: Xaa is Gln or Ala
<220> FEATURE:
<221> NAME/KEY: MISC_FEATURE
<222> LOCATION: (14)..(14)
<223> OTHER INFORMATION: Xaa is Thr or Met
```

-continued

```
<220> FEATURE:
<221> NAME/KEY: MISC_FEATURE
<222> LOCATION: (15)..(15)
<223> OTHER INFORMATION: Xaa is Asp or Glu

<400> SEQUENCE: 41

Xaa Xaa Ala Phe Xaa Met His Asp Glu Xaa Met Phe Glu Xaa Xaa
1               5                   10                  15

<210> SEQ ID NO 42
<211> LENGTH: 15
<212> TYPE: PRT
<213> ORGANISM: Artificial
<220> FEATURE:
<223> OTHER INFORMATION: Variant TAD interaction motif vDREB1A_2
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Asn, His, Arg, Lys, Asp, or Glu
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Tyr, or Trp
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Pro, His, Arg, Lys, Asp, or Glu

<400> SEQUENCE: 42

Xaa Xaa Xaa Phe Xaa Xaa Xaa Xaa Glu Xaa Met Phe Xaa Xaa Xaa
1               5                   10                  15

<210> SEQ ID NO 43
<211> LENGTH: 11
<212> TYPE: PRT
<213> ORGANISM: Artificial
<220> FEATURE:
<223> OTHER INFORMATION: Variant TAD interaction motif vDREB1A_3
<220> FEATURE:
<221> NAME/KEY: MISC_FEATURE
<222> LOCATION: (1)..(1)
<223> OTHER INFORMATION: Xaa is Asp or Glu
<220> FE

```
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(7)
<223> OTHER INFORMATION: Xaa is Gln or Ala
<220> FEATURE:
<221> NAME/KEY: MISC_FEATURE
<222> LOCATION: (10)..(10)
<223> OTHER INFORMATION: Xaa is Thr or Met
<220> FEATURE:
<221> NAME/KEY: MISC_FEATURE
<222> LOCATION: (11)..(11)
<223> OTHER INFORMATION: Xaa is Asp or Glu

<400> SEQUENCE: 43

Xaa Xaa Phe Glu Xaa Glu Xaa Met Phe Xaa Xaa
 1               5                  10

<210> SEQ ID NO 44
<211> LENGTH: 11
<212> TYPE: PRT
<213> ORGANISM: Artificial
<220> FEATURE:
<223> OTHER INFORMATION: Variant TAD interaction motif vDREB1A_4
<220> FEATURE:
<221> NAME/KEY: MISC_FEATURE
<222> LOCATION: (1)..(1)
<223> OTHER INFORMATION: Xaa is His, Arg, Lys, Asp, or Glu
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(7)
<223> OTHER INFORMATION: Xaa is Ser, Thr, Asn, Gln, Cys, Gly, Pro, Ala,
      Val, Leu, Ile, Phe, Tyr, Trp, or Met
<220> FEATURE:
<221> NAME/KEY: MISC_FEATURE
<222> LOCATION: (10)..(10)
<223> OTHER INFORMATION: Xaa is Ser, Thr, Asn, Gln, Cys, Gly, Pro, Ala,
      Val, Leu, Ile, Phe, Tyr, Trp, or Met
<220> FEATURE:
<221> NAME/KEY: MISC_FEATURE
<222> LOCATION: (11)..(11)
<223> OTHER INFORMATION: Xaa is Asp or Glu

<400> SEQUENCE: 44

Xaa Xaa Phe Xaa Xaa Glu Xaa Met Phe Xaa Xaa
 1               5                  10

<210> SEQ ID NO 45
<211> LENGTH: 11
<212> TYPE: PRT
<213> ORGANISM: Artificial
<220> FEATURE:
<223> OTHER INFORMATION: Variant TAD interaction motif vDREB1A_5
<220> FEATURE:
<221> NAME/KEY: MISC_FEATURE
<222> LOCATION: (1)..(1)
<223> OTHER INFORMATION: Xaa is any amino acid
```

```
<220> FEATURE:
<221> NAME/KEY: MISC_FEATURE
<222> LOCATION: (2)..(2)
<223> OTHER INFORMATION: Xaa is Asp, Glu, or Asn
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Tyr, or Trp
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Asp, Glu, or Pro

<400> SEQUENCE: 45

Xaa Xaa Phe Xaa Xaa Glu Xaa Met Phe Xaa Xaa
1               5                   10

<210> SEQ ID NO 46
<211> LENGTH: 11
<212> TYPE: PRT
<213> ORGANISM: Artificial
<220> FEATURE:
<223> OTHER INFORMATION: Variant TAD interaction motif vDREB1A_7

<400> SEQUENCE: 46

Glu Asp Phe Glu Phe Glu Ala Met Phe Met Asp
1               5                   10

<210> SEQ ID NO 47
<211> LENGTH: 9
<212> TYPE: PRT
<213> ORGANISM: Artificial
<220> FEATURE:
<223> OTHER INFORMATION: Variant TAD interaction motif vCBF1_1
<220> FEATURE:
<221> NAME/KEY: MISC_FEATURE
<222> LOCATION: (4)..(4)
<223> OTHER INFORMATION: Xaa is Gln or Thr
<220> FEATURE:
<221> NAME/KEY: MISC_FEATURE
<222> LOCATION: (8)..(8)
<223> OTHER INFORMATION: Xaa is Thr or Met
<220> FEATURE:
<221> NAME/KEY: MISC_FEATURE
<222> LOCATION: (9)..(9)
<223> OTHER INFORMATION: Xaa is Asp or Glu

<400> SEQUENCE: 47

Asp Glu Glu Xaa Met Phe Gly Xaa Xaa
1               5

<210> SEQ ID NO 48
<211> LENGTH: 9
<212> TYPE: PRT
<213> ORGANISM: Artificial
<220> FEATURE:
<223> OTHER INFORMATION: Variant TAD interaction motif vCBF1_2
<220> FEATURE:
<221> NAME/KEY: MISC_FEATURE
<222> LOCATION: (4)..(4)
<223> OTHER INFORMATION: Xaa is any amino acid
```

<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Asp, Glu, or Pro

<400> SEQUENCE: 48

Asp Glu Glu Xaa Met Phe Xaa Xaa Xaa
1               5

<210> SEQ ID NO 49
<211> LENGTH: 11
<212> TYPE: PRT
<213> ORGANISM: Artificial
<220> FEATURE:
<223> OTHER INFORMATION: Variant TAD interaction motif vCBF1_3
<220> FEATURE:
<221> NAME/KEY: MISC_FEATURE
<222> LOCATION: (7)..(7)
<223> OTHER INFORMATION: Xaa is Gln or Thr
<220> FEATURE:
<221> NAME/KEY: MISC_FEATURE
<222> LOCATION: (10)..(10)
<223> OTHER INFORMATION: Xaa is Thr or Met
<220> FEATURE:
<221> NAME/KEY: MISC_FEATURE
<222> LOCATION: (11)..(11)
<223> OTHER INFORMATION: Xaa is Asp or Glu

<400> SEQUENCE: 49

Asp Asp Phe Glu Phe Glu Xaa Met Phe Xaa Xaa
1               5                   10

<210> SEQ ID NO 50
<211> LENGTH: 11
<212> TYPE: PRT
<213> ORGANISM: Artificial
<220> FEATURE:
<223> OTHER INFORMATION: Variant TAD interaction motif vCBF1_4
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is Phe, Trp, or Tyr
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (7)..(7)
<223> OTHER INFORMATION: Xaa is Ser, Thr, Asn, Gln, Cys, Gly, or Tyr
<220> FEATURE:
<221> NAME/KEY: MISC_FEATURE
<222> LOCATION: (10)..(10)
<223> OTHER INFORMATION: Xaa is Ser, Thr, Asn, Gln, Cys, Gly, Pro, Ala,
      Val, Leu, Ile, Phe, Trp, Tyr, or Met
<220> FEATURE:
<221> NAME/KEY: MISC_FEATURE
<222> LOCATION: (11)..(11)
<223> OTHER INFORMATION: Xaa is Asp or Glu

<400> SEQUENCE: 50

Asp Xaa Xaa Glu Xaa Glu Xaa Met Phe Xaa Xaa

```
<210> SEQ ID NO 51
<211> LENGTH: 11
<212> TYPE: PRT
<213> ORGANISM: Artificial
<220> FEATURE:
<223> OTHER INFORMATION: Variant TAD interaction motif vCBF_5
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Asp, Glu, or Pro

<400> SEQUENCE: 51

Asp Xaa Xaa Glu Xaa Glu Xaa Met Phe Xaa Xaa
1               5                   10

<210> SEQ ID NO 52
<211> LENGTH: 11
<212> TYPE: PRT
<213> ORGANISM: Artificial
<220> FEATURE:
<223> OTHER INFORMATION: Variant TAD interaction motif vCBF1_6

<400> SEQUENCE: 52

Asp Asp Phe Glu Phe Glu Thr Met Phe Met Asp
1               5                   10

<210> SEQ ID NO 53
<211> LENGTH: 12
<212> TYPE: PRT
<213> ORGANISM: Artificial
<220> FEATURE:
<223> OTHER INFORMATION: Variant TAD interaction motif vDOF1_1
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Glu or Val
<220> FEATURE:
<221> NAME/KEY: MISC_FEATURE
<222> LOCATION: (6)..(6)
<223> OTHER INFORMATION: Xaa is Phe or Trp
<220> FEATURE:
<221> NAME/KEY: MISC_FEATURE
<222> LOCATION: (7)..(7)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Gln or Ala
```

```
<220> FEATURE:
<221> NAME/KEY: MISC_FEATURE
<222> LOCATION: (9)..(9)
<223> OTHER INFORMATION: Xaa is Met or Ala

<400> SEQUENCE: 53

Xaa Asp Ser Phe Xaa Xaa Xaa Xaa Xaa Ser Phe Asp
 1               5                  10

<210> SEQ ID NO 54
<211> LENGTH: 12
<212> TYPE: PRT
<213> ORGANISM: Artificial
<220> FEATURE:
<223> OTHER INFORMATION: Variant TAD interaction motif vDOF1_2
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Phe, Trp, or Tyr
<220> FEATURE:
<221> NAME/KEY: MISC_FEATURE
<222> LOCATION: (7)..(7)
<223> OTHER INFORMATION: Xaa is Asp, Glu, or Pro
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (10)..(10)
<223> OTHER INFORMATION: Xaa is any amino acid

<400> SEQUENCE: 54

Xaa Asp Xaa Phe Xaa Xaa Xaa Xaa Xaa Xaa Phe Asp
 1               5                  10

<210> SEQ ID NO 55
<211> LENGTH: 11
<212> TYPE: PRT
<213> ORGANISM: Artificial
<220> FEATURE:
<223> OTHER INFORMATION: Variant TAD interaction motif vDOF1_3
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (4)..(4)
<223> OTHER INFORMATION: Xaa is Glu or Val
<220> FEATURE:
<221> NAME/KEY: MISC_FEATURE
<222> LOCATION: (5)..(5)
<223> OTHER INFORMATION: Xaa is Phe or Trp
<220> FEATURE:
<221> NAME/KEY: MISC_FEATURE
<222> LOCATION: (6)..(6)
<223> OTHER INFORMATION: Xaa is Asp or Glu
```

```
<220> FEATURE:
<221> NAME/KEY: MISC_FEATURE
<222> LOCATION: (7)..(7)
<223> OTHER INFORMATION: Xaa is Gln or Ala
<220> FEATURE:
<221> NAME/KEY: MISC_FEATURE
<222> LOCATION: (8)..(8)
<223> OTHER INFORMATION: Xaa is Met or Ala

<400> SEQUENCE: 55

Xaa Asp Phe Xaa Xaa Xaa Xaa Xaa Phe Thr Asp
1               5                   10

<210> SEQ ID NO 56
<211> LENGTH: 11
<212> TYPE: PRT
<213> ORGANISM: Artificial
<220> FEATURE:
<223> OTHER INFORMATION: Variant TAD interaction motif vDOF1_4
<220> FEATURE:
<221> NAME/KEY: MISC_FEATURE
<222> LOCATION: (1)..(1)
<223> OTHER INFORMATION: Xaa is His, Arg, Lys, Asp, or Glu
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ala, Val, Ile, Leu, or Met
<220> FEATURE:
<221> NAME/KEY: MISC_FEATURE
<222> LOCATION: (10)..(10)
<223> OTHER INFORMATION: Xaa is Ser, Thr, Asn, Gln, Cys, Gly, Pro, or
      Tyr

<400> SEQUENCE: 56

Xaa Asp Phe Xaa Xaa Xaa Xaa Xaa Phe Xaa Asp
1               5                   10

<210> SEQ ID NO 57
<211> LENGTH: 11
<212> TYPE: PRT
<213> ORGANISM: Artificial
<220> FEATURE:
<223> OTHER INFORMATION: Variant TAD interaction motif vDOF1_5
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (6)..(6)
<223> OTHER INFORMATION: Xaa is Asp, Glu, or Pro
```

```
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ala, Val, Ile, Leu, Met, Phe, Tyr, or
      Trp
<220> FEATURE:
<221> NAME/KEY: MISC_FEATURE
<222> LOCATION: (10)..(10)
<223> OTHER INFORMATION: Xaa is any amino acid

<400> SEQUENCE: 57

Xaa Asp Phe Xaa Xaa Xaa Xaa Xaa Phe Xaa Asp
1               5                   10

<210> SEQ ID NO 58
<211> LENGTH: 11
<212> TYPE: PRT
<213> ORGANISM: Artificial
<220> FEATURE:
<223> OTHER INFORMATION: Variant TAD interaction motif vDOF1_6

<400> SEQUENCE: 58

Glu Asp Phe Glu Phe Glu Ala Met Phe Thr Asp
1               5                   10

<210> SEQ ID NO 59
<211> LENGTH: 60
<212> TYPE: DNA
<213> ORGANISM: Artificial
<220> FEATURE:
<223> OTHER INFORMATION: Primer KanMX-For

<400> SEQUENCE: 59
aagaaactag tggatccgct agcttaatta aagatctggt accgtttagc ttgcctcgtc     60

<210> SEQ ID NO 60
<211> LENGTH: 30
<212> TYPE: DNA
<213> ORGANISM: Artificial
<220> FEATURE:
<223> OTHER INFORMATION: Primer KanMX-Rev

<400> SEQUENCE: 60
aagaaggaat tcagagctcg ttttcgacac                                     30

<210> SEQ ID NO 61
<211> LENGTH: 15
<212> TYPE: DNA
<213> ORGANISM: Artificial
<220> FEATURE:
<223> OTHER INFORMATION: Primer HO-For

<400> SEQUENCE: 61
ttgcccgaat tcctg                                                     15

<210> SEQ ID NO 62
<211> LENGTH: 27
<212> TYPE: DNA
<213> ORGANISM: Artificial
<220> FEATURE:
<223> OTHER INFORMATION: Primer HO-Rev

<400> SEQUENCE: 62
aagaagacta gtcgtacgac gccattt                                        27
```

<210> SEQ ID NO 63
<211> LENGTH: 33
<212> TYPE: DNA
<213> ORGANISM: Artificial
<220> FEATURE:
<223> OTHER INFORMATION: Primer MEL1-For

<400> SEQUENCE: 63
acggaacggg taccaagaag aaaggaagac atg         33

<210> SEQ ID NO 64
<211> LENGTH: 18
<212> TYPE: DNA
<213> ORGANISM: Artificial
<220> FEATURE:
<223> OTHER INFORMATION: Primer MEL1-Rev

<400> SEQUENCE: 64
ctaaagggaa caaaagct                          18

<210> SEQ ID NO 65
<211> LENGTH: 28
<212> TYPE: DNA
<213> ORGANISM: Artificial
<220> FEATURE:
<223> OTHER INFORMATION: Primer HAS-For-F1

<400> SEQUENCE: 65
tagattggga tcctgggggg cgcggaac               28

<210> SEQ ID NO 66
<211> LENGTH: 33
<212> TYPE: DNA
<213> ORGANISM: Artificial
<220> FEATURE:
<223> OTHER INFORMATION: Primer HAS-For-R1

<400> SEQUENCE: 66
tagattgtta attaatggtc atcctcatcc tgc         33

<210> SEQ ID NO 67
<211> LENGTH: 21
<212> TYPE: DNA
<213> ORGANISM: Artificial
<220> FEATURE:
<223> OTHER INFORMATION: Z6 sequence

<400> SEQUENCE: 67
tgtggtggga gaggagggtg g                      21

<210> SEQ ID NO 68
<211> LENGTH: 201
<212> TYPE: DNA
<213> ORGANISM: Artificial
<220> FEATURE:
<223> OTHER INFORMATION: 8x Z6 repeated sequence

<400> SEQUENCE: 68
ggtgtggtgg gagaggaggg tgggagtgtg gtgggagagg agggtggctc tgtggtggga    60
gaggagggtg gagatgtggt gggagaggag ggtggtcttg tggtgggaga ggagggtggg   120
gatgtggtgg gagaggaggg tggccttgtg gtgggagagg agggtggagg tgtggtggga   180
gaggagggtg gcttaagccg c                                             201

```
<210> SEQ ID NO 69
<211> LENGTH: 29
<212> TYPE: DNA
<213> ORGANISM: Artificial
<220> FEATURE:
<223> OTHER INFORMATION: Primer TQPATS

<400> SEQUENCE: 69
acaagagtgg attgatgatc tagagaggt                                29

<210> SEQ ID NO 70
<211> LENGTH: 29
<212> TYPE: DNA
<213> ORGANISM: Artificial
<220> FEATURE:
<223> OTHER INFORMATION: Primer TQPATA

<400> SEQUENCE: 70
ctttgatgcc tatgtgacac gtaaacagt                                29

<210> SEQ ID NO 71
<211> LENGTH: 29
<212> TYPE: DNA
<213> ORGANISM: Artificial
<220> FEATURE:
<223> OTHER INFORMATION: Primer TQPATFQ

<400> SEQUENCE: 71
ggtgttgtgg ctggtattgc ttacgctgg                                29

<210> SEQ ID NO 72
<211> LENGTH: 30
<212> TYPE: DNA
<213> ORGANISM: Artificial
<220> FEATURE:
<223> OTHER INFORMATION: Primer TQPALS

<400> SEQUENCE: 72
tactatgact tgatgttgtg tggtgactga                               30

<210> SEQ ID NO 73
<211> LENGTH: 28
<212> TYPE: DNA
<213> ORGANISM: Artificial
<220> FEATURE:
<223> OTHER INFORMATION: Primer TQPALA

<400> SEQUENCE: 73
gagcggtcta aattccgacc cttatttc                                 28

<210> SEQ ID NO 74
<211> LENGTH: 33
<212> TYPE: DNA
<213> ORGANISM: Artificial
<220> FEATURE:
<223> OTHER INFORMATION: 6FAM probe TQPALFQ

<400> SEQUENCE: 74
aaacgatggc aggagtgccc ttttctatc aat                            33

<210> SEQ ID NO 75
<211> LENGTH: 19
<212> TYPE: DNA
<213> ORGANISM: Artificial
<220> FEATURE:
<223> OTHER INFORMATION: Primer Blu636
```

-continued

<400> SEQUENCE: 75
gagaggaggg tggagatgt                                                19

<210> SEQ ID NO 76
<211> LENGTH: 19
<212> TYPE: DNA
<213> ORGANISM: Artificial
<220> FEATURE:
<223> OTHER INFORMATION: Primer Blu637

<400> SEQUENCE: 76
accttggact cccatgttg                                                19

<210> SEQ ID NO 77
<211> LENGTH: 21
<212> TYPE: DNA
<213> ORGANISM: Artificial
<220> FEATURE:
<223> OTHER INFORMATION: Primer 3'CHS forward

<400> SEQUENCE: 77
ctgatccaat tccagaggtc g                                             21

<210> SEQ ID NO 78
<211> LENGTH: 24
<212> TYPE: DNA
<213> ORGANISM: Artificial
<220> FEATURE:
<223> OTHER INFORMATION: Primer 3'CHS reverse

<400> SEQUENCE: 78
acacacaagc actagacatg ttgc                                          24

<210> SEQ ID NO 79
<211> LENGTH: 102
<212> TYPE: DNA
<213> ORGANISM: Artificial
<220> FEATURE:
<223> OTHER INFORMATION: Synthetic sequence encoding VP16 TAD
      interaction motif fused to Z6 DNA binding motif

<400> SEQUENCE: 79
ggcatgaccc atgatcctgt gtcttatgga gccttggatg ttgatgactt tgagtttgag    60
cagatgttca cagatgcact gggcatcgat gactttggtg ga                     102

<210> SEQ ID NO 80
<211> LENGTH: 99
<212> TYPE: DNA
<213> ORGANISM: Artificial
<220> FEATURE:
<223> OTHER INFORMATION: Synthetic sequence encoding ERF2 TAD
      interaction motif fused to Z6 DNA binding motif

<400> SEQUENCE: 80
aatgactctg aggacatgct ggtgtatggt ttgctcaagg atgcctttca ctttgacacc    60
tccagctcag acctctcctg cctctttgac ttcccagcc                          99

<210> SEQ ID NO 81
<211> LENGTH: 123
<212> TYPE: DNA
<213> ORGANISM: Artificial
<220> FEATURE:
<223> OTHER INFORMATION: Synthetic sequence encoding PTI4 TAD
      interaction motif fused to Z6 DNA binding motif

```
<400> SEQUENCE: 81
tgcctgacag aaacttgggg agacttgcct ctcaaggttg atgactctga ggacatggtg    60
atctatggtc tgttgaagga tgcactctca gtggggtggt ccccattctc tttcacggct   120
ggt                                                                 123

<210> SEQ ID NO 82
<211> LENGTH: 96
<212> TYPE: DNA
<213> ORGANISM: Artificial
<220> FEATURE:
<223> OTHER INFORMATION: Synthetic sequence encoding AtERF1 TAD
      interaction motif fused to Z6 DNA binding motif

<400> SEQUENCE: 82
tgcttcacgg aatcctgggg agaccttcct ttgaaggaga atgactctga ggacatgttg    60
gtgtacggaa tcctcaatga tgcttttcat ggtggc                             96

<210> SEQ ID NO 83
<211> LENGTH: 108
<212> TYPE: DNA
<213> ORGANISM: Artificial
<220> FEATURE:
<223> OTHER INFORMATION: Synthetic sequence encoding ORCA2 TAD
      interaction motif fused to Z6 DNA binding motif

<400> SEQUENCE: 83
ttcaatgaga attgtgaaga aatcatctct ccaaactacg catcagagga cttgtctgac    60
atcatcttga cggacatctt caaggaccaa gacaactatg aggatgag                108

<210> SEQ ID NO 84
<211> LENGTH: 129
<212> TYPE: DNA
<213> ORGANISM: Artificial
<220> FEATURE:
<223> OTHER INFORMATION: Synthetic sequence encoding DREB1A TAD
      interaction motif fused to Z6 DNA binding motif

<400> SEQUENCE: 84
ggctttgaca tggaagaaac attggtggag gccatctaca ctgctgaaca gagcgagaat    60
gccttctaca tgcatgatga ggcaatgttt gagatgccat ctcttctggc caacatggct   120
gagggaatg                                                           129

<210> SEQ ID NO 85
<211> LENGTH: 81
<212> TYPE: DNA
<213> ORGANISM: Artificial
<220> FEATURE:
<223> OTHER INFORMATION: Synthetic sequence encoding CBF1 TAD
      interaction motif fused to Z6 DNA binding motif

<400> SEQUENCE: 85
gaacagtcag aaggtgcttt ctacatggat gaagagacca tgtttgggat gccaaccctt    60
ctggataaca tggcagaggg a                                             81

<210> SEQ ID NO 86
<211> LENGTH: 99
<212> TYPE: DNA
<213> ORGANISM: Artificial
<220> FEATURE:
<223> OTHER INFORMATION: Synthetic sequence encoding DOF1 TAD
      interaction motif fused to Z6 DNA binding motif
```

<400> SEQUENCE: 86
tcagctggga aggcagtctt ggatgatgag gacagctttg tttggcctgc tgcatccttt    60
gacatgggtg cctgctgggc tggagctggc tttgctgac                          99

<210> SEQ ID NO 87
<211> LENGTH: 99
<212> TYPE: DNA
<213> ORGANISM: Artificial
<220> FEATURE:
<223> OTHER INFORMATION: Synthetic sequence encoding exemplary variant
      ERF2 TAD interaction motif fused to Z6 DNA binding motif

<400> SEQUENCE: 87
aatgactctg aggacatgct ggtgtatggt ttgctcaagg atgatttcca ctttgagaca    60
atgttctcag acctgtcctg cctctttgac ttcccagcc                          99

<210> SEQ ID NO 88
<211> LENGTH: 114
<212> TYPE: DNA
<213> ORGANISM: Artificial
<220> FEATURE:
<223> OTHER INFORMATION: Synthetic sequence encoding exemplary variant
      PTI4 TAD interaction motif fused to Z6 DNA binding motif

<400> SEQUENCE: 88
tgcctgacag aaacttgggg agacttgcct ctcaaggttg atgactttga gtttgagatg    60
atgttcacag atgcactctc agtggggtgg tccccattct ctttcacggc tggt         114

<210> SEQ ID NO 89
<211> LENGTH: 102
<212> TYPE: DNA
<213> ORGANISM: Artificial
<220> FEATURE:
<223> OTHER INFORMATION: Synthetic sequence encoding exemplary variant
      AtERF1 TAD interaction motif fused to Z6 DNA binding motif

<400> SEQUENCE: 89
tgcttcacgg aatcctgggg agaccttcct ttgaaggaga atgactttga gtttgaaatg    60
ttcacagatt acggaatcct caatgatgct tttcatggtg gc                      102

<210> SEQ ID NO 90
<211> LENGTH: 108
<212> TYPE: DNA
<213> ORGANISM: Artificial
<220> FEATURE:
<223> OTHER INFORMATION: Synthetic sequence encoding exemplary variant
      ORCA2 TAD interaction motif fused to Z6 DNA binding motif

<400> SEQUENCE: 90
ttcaatgaga attgtgaaga aatcatctct ccaaactacg catcagagga ctttgatctt    60
gagatgttga cggacatctt caaggaccaa gacaactatg aggatgag                108

<210> SEQ ID NO 91
<211> LENGTH: 117
<212> TYPE: DNA
<213> ORGANISM: Artificial
<220> FEATURE:
<223> OTHER INFORMATION: Synthetic sequence encoding exemplary variant
      DREB1A TAD interaction motif fused to Z6 DNA binding motif

<400> SEQUENCE: 91
ggctttgaca tggaagaaac attggtggag gccatctaca ctgctgaaca gagcgaggac    60
tttgagtttg aagcaatgtt catggattct cttctggcca acatggctga gggaatg        117

<210> SEQ ID NO 92
<211> LENGTH: 87
<212> TYPE: DNA
<213> ORGANISM: Artificial
<220> FEATURE:
<223> OTHER INFORMATION: Synthetic sequence encoding exemplary variant
      CBF1 TAD interaction motif fused to Z6 DNA binding motif

<400> SEQUENCE: 92
gaacagtcag aaggtgcttt ctacatggat gactttgagt tcgagacaat gttcatggac        60
acccttctgg ataacatggc agaggga        87

<210> SEQ ID NO 93
<211> LENGTH: 96
<212> TYPE: DNA
<213> ORGANISM: Artificial
<220> FEATURE:
<223> OTHER INFORMATION: Synthetic sequence encoding exemplary variant
      DOF1 TAD interaction motif fused to Z6 DNA binding motif

<400> SEQUENCE: 93
tcagctggga aggcagtctt ggatgatgag gactttgagt ttgaagccat gttcacggac        60
atgggtgcct gctgggctgg agctggcttt gctgac        96

<210> SEQ ID NO 94
<211> LENGTH: 22
<212> TYPE: DNA
<213> ORGANISM: Artificial
<220> FEATURE:
<223> OTHER INFORMATION: Primer TQGUSS

<400> SEQUENCE: 94
agacagagtg tgatatctac cc        22

<210> SEQ ID NO 95
<211> LENGTH: 20
<212> TYPE: DNA
<213> ORGANISM: Artificial
<220> FEATURE:
<223> OTHER INFORMATION: Primer TQGUSA

<400> SEQUENCE: 95
ccatcagcac gttatcgaat        20

<210> SEQ ID NO 96
<211> LENGTH: 26
<212> TYPE: DNA
<213> ORGANISM: Artificial
<220> FEATURE:
<223> OTHER INFORMATION: 6FAM probe TQGUSFQ

<400> SEQUENCE: 96
cacaaaccgt tctactttac tggctt        26

<210> SEQ ID NO 97
<211> LENGTH: 19
<212> TYPE: DNA
<213> ORGANISM: Artificial
<220> FEATURE:
<223> OTHER INFORMATION: Primer BYEEFU119F

<400> SEQUENCE: 97

```
aggctcccac ttcaggatg                                                        19
```

<210> SEQ ID NO 98
<211> LENGTH: 20
<212> TYPE: DNA
<213> ORGANISM: Artificial
<220> FEATURE:
<223> OTHER INFORMATION: Primer BYEEFU119R

<400> SEQUENCE: 98

```
cacgaccaac agggacagta                                                       20
```

<210> SEQ ID NO 99
<211> LENGTH: 19
<212> TYPE: DNA
<213> ORGANISM: Artificial
<220> FEATURE:
<223> OTHER INFORMATION: UPA DNA binding domain
<220> FEATURE:
<221> NAME/KEY: misc_feature
<222> LOCATION: (12)..(13)
<223> OTHER INFORMATION: n is a, c, g, or t

<400> SEQUENCE: 99

```
tatataaacc tnnccctct                                                        19
```

<210> SEQ ID NO 100
<211> LENGTH: 34
<212> TYPE: PRT
<213> ORGANISM: Artificial
<220> FEATURE:
<223> OTHER INFORMATION: Exemplary synthetic TAD comprising a ERF2 plant
      TAD interaction motif

<400> SEQUENCE: 100

```
Gly Met Thr His Asp Pro Val Ser Tyr Gly Ala Leu Asp Val Asp Ala
1               5                   10                  15

Phe His Phe Asp Thr Ser Ser Ser Asp Ala Leu Gly Ile Asp Asp Phe
            20                  25                  30

Gly Gly
```

<210> SEQ ID NO 101
<211> LENGTH: 37
<212> TYPE: PRT
<213> ORGANISM: Artificial
<220> FEATURE:
<223> OTHER INFORMATION: Exemplary synthetic TAD comprising a PTI4 plant
      TAD interaction motif

<400> SEQUENCE: 101

```
Gly Met Thr His Asp Pro Val Ser Tyr Gly Ala Leu Asp Val Asp Asp
1               5                   10                  15

Ser Glu Asp Met Val Ile Tyr Gly Leu Leu Lys Asp Ala Leu Gly Ile
            20                  25                  30

Asp Asp Phe Gly Gly
        35
```

<210> SEQ ID NO 102
<211> LENGTH: 32
<212> TYPE: PRT
<213> ORGANISM: Artificial
<220> FEATURE:
<223> OTHER INFORMATION: Exemplary synthetic TAD comprising a AtERF1
      plant TAD interaction motif

<400> SEQUENCE: 102

-continued

Gly Met Thr His Asp Pro Val Ser Tyr Gly Ala Leu Asp Val Glu Asn
1               5                   10                  15

Asp Ser Glu Asp Met Leu Val Ala Leu Gly Ile Asp Asp Phe Gly Gly
                20                  25                  30

<210> SEQ ID NO 103
<211> LENGTH: 33
<212> TYPE: PRT
<213> ORGANISM: Artificial
<220> FEATURE:
<223> OTHER INFORMATION: Exemplary synthetic TAD comprising a ORCA2
      plant TAD interaction motif

<400> SEQUENCE: 103

Gly Met Thr His Asp Pro Val Ser Tyr Gly Ala Leu Asp Val Glu Asp
1               5                   10                  15

Leu Ser Asp Ile Ile Leu Thr Asp Ala Leu Gly Ile Asp Asp Phe Gly
                20                  25                  30

Gly

<210> SEQ ID NO 104
<211> LENGTH: 38
<212> TYPE: PRT
<213> ORGANISM: Artificial
<220> FEATURE:
<223> OTHER INFORMATION: Exemplary synthetic TAD comprising a DREB1A
      plant TAD interaction motif

<400> SEQUENCE: 104

Gly Met Thr His Asp Pro Val Ser Tyr Gly Ala Leu Asp Val Glu Asn
1               5                   10                  15

Ala Phe Tyr Met His Asp Glu Ala Met Phe Glu Met Pro Ala Leu Gly
                20                  25                  30

Ile Asp Asp Phe Gly Gly
        35

<210> SEQ ID NO 105
<211> LENGTH: 32
<212> TYPE: PRT
<213> ORGANISM: Artificial
<220> FEATURE:
<223> OTHER INFORMATION: Exemplary synthetic TAD comprising a CBF1 plant
      TAD interaction motif

<400> SEQUENCE: 105

Gly Met Thr His Asp Pro Val Ser Tyr Gly Ala Leu Asp Val Asp Glu
1               5                   10                  15

Glu Thr Met Phe Gly Met Pro Ala Leu Gly Ile Asp Asp Phe Gly Gly
                20                  25                  30

<210> SEQ ID NO 106
<211> LENGTH: 35
<212> TYPE: PRT
<213> ORGANISM: Artificial
<220> FEATURE:
<223> OTHER INFORMATION: Exemplary synthetic TAD comprising a DOF1 plant
      TAD interaction motif

<400> SEQUENCE: 106

Gly Met Thr His Asp Pro Val Ser Tyr Gly Ala Leu Asp Val Glu Asp
1               5                   10                  15

Ser Phe Val Trp Pro Ala Ala Ser Phe Asp Ala Leu Gly Ile Asp Asp
                20                  25                  30

Phe Gly Gly
            35

<210> SEQ ID NO 107
<211> LENGTH: 34
<212> TYPE: PRT
<213> ORGANISM: Artificial
<220> FEATURE:
<223> OTHER INFORMATION: Exemplary synthetic TAD comprising a variant
      ERF2 TAD interaction motif

<400> SEQUENCE: 107

Gly Met Thr His Asp Pro Val Ser Tyr Gly Ala Leu Asp Val Asp Asp
1               5                   10                  15

Phe His Phe Glu Thr Met Phe Ser Asp Ala Leu Gly Ile Asp Asp Phe
            20                  25                  30

Gly Gly

<210> SEQ ID NO 108
<211> LENGTH: 33
<212> TYPE: PRT
<213> ORGANISM: Artificial
<220> FEATURE:
<223> OTHER INFORMATION: Exemplary synthetic TAD comprising a variant
      ERF2 TAD interaction motif

<400> SEQUENCE: 108

Asn Asp Ser Glu Asp Met Leu Val Tyr Gly Leu Leu Lys Asp Asp Phe
1               5                   10                  15

His Phe Glu Thr Met Phe Ser Asp Leu Ser Cys Leu Phe Asp Phe Pro
            20                  25                  30

Ala

<210> SEQ ID NO 109
<211> LENGTH: 34
<212> TYPE: PRT
<213> ORGANISM: Artificial
<220> FEATURE:
<223> OTHER INFORMATION: Exemplary synthetic TAD comprising a variant
      PTI4 TAD interaction motif

<400> SEQUENCE: 109

Gly Met Thr His Asp Pro Val Ser Tyr Gly Ala Leu Asp Val Asp Asp
1               5                   10                  15

Phe Glu Phe Glu Met Met Phe Thr Asp Ala Leu Gly Ile Asp Asp Phe
            20                  25                  30

Gly Gly

<210> SEQ ID NO 110
<211> LENGTH: 38
<212> TYPE: PRT
<213> ORGANISM: Artificial
<220> FEATURE:
<223> OTHER INFORMATION: Exemplary synthetic TAD comprising a variant
      PTI4 TAD interaction motif

<400> SEQUENCE: 110

Cys Leu Thr Glu Thr Trp Gly Asp Leu Pro Leu Lys Val Asp Asp Phe
1               5                   10                  15

Glu Phe Glu Met Met Phe Thr Asp Ala Leu Ser Val Gly Trp Ser Pro
            20                  25                  30

Phe Ser Phe Thr Ala Gly

```
<210> SEQ ID NO 111
<211> LENGTH: 34
<212> TYPE: PRT
<213> ORGANISM: Artificial
<220> FEATURE:
<223> OTHER INFORMATION: Exemplary synthetic TAD comprising a variant
      AtERF1 TAD interaction motif

<400> SEQUENCE: 111

Gly Met Thr His Asp Pro Val Ser Tyr Gly Ala Leu Asp Val Glu Asn
1               5                   10                  15

Asp Phe Glu Phe Glu Met Phe Thr Asp Ala Leu Gly Ile Asp Asp Phe
            20                  25                  30

Gly Gly

<210> SEQ ID NO 112
<211> LENGTH: 34
<212> TYPE: PRT
<213> ORGANISM: Artificial
<220> FEATURE:
<223> OTHER INFORMATION: Exemplary synthetic TAD comprising a variant
      AtERF1 TAD interaction motif

<400> SEQUENCE: 112

Cys Phe Thr Glu Ser Trp Gly Asp Leu Pro Leu Lys Glu Asn Asp Phe
1               5                   10                  15

Glu Phe Glu Met Phe Thr Asp Tyr Gly Ile Leu Asn Asp Ala Phe His
            20                  25                  30

Gly Gly

<210> SEQ ID NO 113
<211> LENGTH: 33
<212> TYPE: PRT
<213> ORGANISM: Artificial
<220> FEATURE:
<223> OTHER INFORMATION: Exemplary synthetic TAD comprising a variant
      ORCA2 TAD interaction motif

<400> SEQUENCE: 113

Gly Met Thr His Asp Pro Val Ser Tyr Gly Ala Leu Asp Val Glu Asp
1               5                   10                  15

Phe Asp Leu Glu Met Leu Thr Asp Ala Leu Gly Ile Asp Asp Phe Gly
            20                  25                  30

Gly

<210> SEQ ID NO 114
<211> LENGTH: 36
<212> TYPE: PRT
<213> ORGANISM: Artificial
<220> FEATURE:
<223> OTHER INFORMATION: Exemplary synthetic TAD comprising a variant
      ORCA2 TAD interaction motif

<400> SEQUENCE: 114

Phe Asn Glu Asn Cys Glu Glu Ile Ile Ser Pro Asn Tyr Ala Ser Glu
1               5                   10                  15

Asp Phe Asp Leu Glu Met Leu Thr Asp Ile Phe Lys Asp Gln Asp Asn
            20                  25                  30

Tyr Glu Asp Glu
            35
```

<210> SEQ ID NO 115
<211> LENGTH: 34
<212> TYPE: PRT
<213> ORGANISM: Artificial
<220> FEATURE:
<223> OTHER INFORMATION: Exemplary synthetic TAD comprising a variant
      DREB1A TAD interaction motif

<400> SEQUENCE: 115

Gly Met Thr His Asp Pro Val Ser Tyr Gly Ala Leu Asp Val Glu Asp
1               5                   10                  15

Phe Glu Phe Glu Ala Met Phe Met Asp Ala Leu Gly Ile Asp Asp Phe
            20                  25                  30

Gly Gly

<210> SEQ ID NO 116
<211> LENGTH: 39
<212> TYPE: PRT
<213> ORGANISM: Artificial
<220> FEATURE:
<223> OTHER INFORMATION: Exemplary synthetic TAD comprising a variant
      DREB1A TAD interaction motif

<400> SEQUENCE: 116

Gly Phe Asp Met Glu Glu Thr Leu Val Glu Ala Ile Tyr Thr Ala Glu
1               5                   10                  15

Gln Ser Glu Asp Phe Glu Phe Glu Ala Met Phe Met Asp Ser Leu Leu
            20                  25                  30

Ala Asn Met Ala Glu Gly Met
        35

<210> SEQ ID NO 117
<211> LENGTH: 34
<212> TYPE: PRT
<213> ORGANISM: Artificial
<220> FEATURE:
<223> OTHER INFORMATION: Exemplary synthetic TAD comprising a variant
      CBF1 TAD interaction motif

<400> SEQUENCE: 117

Gly Met Thr His Asp Pro Val Ser Tyr Gly Ala Leu Asp Val Asp Asp
1               5                   10                  15

Phe Glu Phe Glu Thr Met Phe Met Asp Ala Leu Gly Ile Asp Asp Phe
            20                  25                  30

Gly Gly

<210> SEQ ID NO 118
<211> LENGTH: 29
<212> TYPE: PRT
<213> ORGANISM: Artificial
<220> FEATURE:
<223> OTHER INFORMATION: Exemplary synthetic TAD comprising a variant
      CBF1 TAD interaction motif

<400> SEQUENCE: 118

Glu Gln Ser Glu Gly Ala Phe Tyr Met Asp Asp Phe Glu Phe Glu Thr
1               5                   10                  15

Met Phe Met Asp Thr Leu Leu Asp Asn Met Ala Glu Gly
            20                  25

<210> SEQ ID NO 119
<211> LENGTH: 34
<212> TYPE: PRT

```
<213> ORGANISM: Artificial
<220> FEATURE:
<223> OTHER INFORMATION: Exemplary synthetic TAD comprising a variant
      DOF1 TAD interaction motif

<400> SEQUENCE: 119

Gly Met Thr His Asp Pro Val Ser Tyr Gly Ala Leu Asp Val Glu Asp
1               5                   10                  15

Phe Glu Phe Glu Ala Met Phe Thr Asp Ala Leu Gly Ile Asp Asp Phe
                20                  25                  30

Gly Gly

<210> SEQ ID NO 120
<211> LENGTH: 32
<212> TYPE: PRT
<213> ORGANISM: Artificial
<220> FEATURE:
<223> OTHER INFORMATION: Exemplary synthetic TAD comprising a variant
      DOF1 TAD interaction motif

<400> SEQUENCE: 120

Ser Ala Gly Lys Ala Val Leu Asp Asp Glu Asp Phe Glu Phe Glu Ala
1               5                   10                  15

Met Phe Thr Asp Met Gly Ala Cys Trp Ala Gly Ala Gly Phe Ala Asp
                20                  25                  30

<210> SEQ ID NO 121
<211> LENGTH: 11
<212> TYPE: PRT
<213> ORGANISM: Artificial
<220> FEATURE:
<223> OTHER INFORMATION: Variant TAD interaction motif vERF2_7
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Ala, Val, Ile, Leu, or Met
<220> FEATURE:
<221> NAME/KEY: MISC_FEATURE
<222> LOCATION: (9)..(9)
<223> OTHER INFORMATION: Xaa is Phe, Trp, or Tyr

<400> SEQUENCE: 121

Asp Xaa Phe His Phe Xaa Thr Xaa Xaa Ser Asp
1               5                   10

<210> SEQ ID NO 122
<211> LENGTH: 11
<212> TYPE: PRT
<213> ORGANISM: Artificial
<220> FEATURE:
<223> OTHER INFORMATION: Variant TAD interaction motif vPTI4_7
<220> FEATURE:
<221> NAME/KEY: MISC_FEATURE
<222> LOCATION: (3)..(3)
<223> OTHER INFORMATION: Xaa is Phe or Ser
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (6)..(6)
```

```
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Ala, Val, Ile, Leu, or Met
<220> FEATURE:
<221> NAME/KEY: MISC_FEATURE
<222> LOCATION: (9)..(9)
<223> OTHER INFORMATION: Xaa is Phe, Trp, or Tyr
<220> FEATURE:
<221> NAME/KEY: MISC_FEATURE
<222> LOCATION: (10)..(10)
<223> OTHER INFORMATION: Xaa is Thr or Leu

<400> SEQUENCE: 122

Asp Asp Xaa Glu Xaa Xaa Met Xaa Xaa Xaa Asp
1               5                   10

<210> SEQ ID NO 123
<211> LENGTH: 11
<212> TYPE: PRT
<213> ORGANISM: Artificial
<220> FEATURE:
<223> OTHER INFORMATION: Variant TAD interaction motif vAtERF1_7
<220> FEATURE:
<221> NAME/KEY: MISC_FEATURE
<222> LOCATION: (4)..(4)
<223> OTHER INFORMATION: Xaa is Phe or Ser
<220> FEATURE:
<221> NAME/KEY: MISC_FEATURE
<222> LOCATION: (6)..(6)
<223> OTHER INFORMATION: Xaa is Phe, Trp, or Tyr
<220> FEATURE:
<221> NAME/KEY: MISC_FEATURE
<222> LOCATION: (7)..(7)
<223> OTHER INFORMATION: Xaa is Asp or Glu
<220> FEATURE:
<221> NAME/KEY: MISC_FEATURE
<222> LOCATION: (9)..(9)
<223> OTHER INFORMATION: Xaa is Phe, Trp, Tyr, or Leu
<220> FEATURE:
<221> NAME/KEY: MISC_FEATURE
<222> LOCATION: (10)..(10)
<223> OTHER INFORMATION: Xaa is Thr or Val
<220> FEATURE:
<221> NAME/KEY: MISC_FEATURE
<222> LOCATION: (11)..(11)
<223> OTHER INFORMATION: Xaa is Asp or Glu

<400> SEQUENCE: 123

Glu Asn Asp Xaa Glu Xaa Xaa Met Xaa Xaa Xaa
1               5                   10

<210> SEQ ID NO 124
<211> LENGTH: 10
<212> TYPE: PRT
<213> ORGANISM: Artificial
<220> FEATURE:
<223> OTHER INFORMATION: Variant TAD interaction motif vORCA2_7
<220> FEATURE:
<221> NAME/KEY: MISC_FEATURE
<222> LOCATION: (3)..(3)
<223> OTHER INFORMATION: Xaa is Phe or Leu
<220> FEATURE:
<221> NAME/KEY: MISC_FEATURE
<222> LOCATION: (4)..(4)
<223> OTHER INFORMATION: Xaa is Phe, Tyr, Trp, or Asp
<220> FEATURE:
<221> NAME/KEY: MISC_FEATURE
<222> LOCATION: (5)..(5)
<223> OTHER INFORMATION: Xaa is Asp, Glu, Ile, or Leu
<220> FEATURE:
<221> NAME/KEY: MISC_FEATURE
<222> LOCATION: (6)..(6)
<223> OTHER INFORMATION: Xaa is Gln or Glu
```

```
<220> FEATURE:
<221> NAME/KEY: MISC_FEATURE
<222> LOCATION: (7)..(7)
<223> OTHER INFORMATION: Xaa is Ala, Val, Ile, Leu, or Met
<220> FEATURE:
<221> NAME/KEY: MISC_FEATURE
<222> LOCATION: (8)..(8)
<223> OTHER INFORMATION: Xaa is Phe, Tyr, Trp, or Leu

<400> SEQUENCE: 124

Glu Asp Xaa Xaa Xaa Xaa Xaa Xaa Thr Asp
1               5                   10

<210> SEQ ID NO 125
<211> LENGTH: 11
<212> TYPE: PRT
<213> ORGANISM: Artificial
<220> FEATURE:
<223> OTHER INFORMATION: Variant TAD interaction motif vDREB1A_7
<220> FEATURE:
<221> NAME/KEY: MISC_FEATURE
<222> LOCATION: (2)..(2)
<223> OTHER INFORMATION: Xaa is Asp, Glu, or Asn
<220> FEATURE:
<221> NAME/KEY: MISC_FEATURE
<222> LOCATION: (5)..(5)
<223> OTHER INFORMATION: Xaa is Phe, Tyr, or Trp
<220> FEATURE:
<221> NAME/KEY: MISC_FEATURE
<222> LOCATION: (11)..(11)
<223> OTHER INFORMATION: Xaa is Asp, Glu, or Pro

<400> SEQUENCE: 125

Glu Xaa Phe Glu Xaa Glu Ala Met Phe Met Xaa
1               5                   10

<210> SEQ ID NO 126
<211> LENGTH: 11
<212> TYPE: PRT
<213> ORGANISM: Artificial
<220> FEATURE:
<223> OTHER INFORMATION: Variant TAD interaction motif vCBF1_7
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Phe, Trp, or Tyr
<220> FEATURE:
<221> NAME/KEY: MISC_FEATURE
<222> LOCATION: (11)..(11)
<223> OTHER INFORMATION: Xaa is Asp, Glu, or Pro

<400> SEQUENCE: 126

Asp Xaa Phe Glu Xaa Glu Thr Met Phe Met Xaa
1               5                   10

<210> SEQ ID NO 127
<211> LENGTH: 11
<212> TYPE: PRT
<213> ORGANISM: Artificial
<220> FEATURE:
<223> OTHER INFORMATION: Variant TAD interaction motif vDOF1_7
<220> FEATURE:
<221> NAME/KEY: MISC_FEATURE
<222> LOCATION: (4)..(4)
<223> OTHER INFORMATION: Xaa is Glu or Val
<220> FEATURE:
<221> NAME/KEY: MISC_FEATURE
<222> LOCATION: (5)..(5)
<223> OTHER INFORMATION: Xaa is Phe, Trp, or Tyr
```

```
<220> FEATURE:
<221> NAME/KEY: MISC_FEATURE
<222> LOCATION: (6)..(6)
<223> OTHER INFORMATION: Xaa is Asp, Glu, or Pro
<220> FEATURE:
<221> NAME/KEY: MISC_FEATURE
<222> LOCATION: (8)..(8)
<223> OTHER INFORMATION: Xaa is Ala, Val, Ile, Leu, or Met

<400> SEQUENCE: 127

Glu Asp Phe Xaa Xaa Xaa Ala Xaa Phe Thr Asp
1               5                   10
```

What is claimed is:

1. A synthetic transcriptional activator fusion protein comprising:
   a single DNA-binding peptide; and
   a heterologous transactivation domain comprising the interaction motif peptide of SEQ ID NO:52.

2. The synthetic transcriptional activator fusion protein of claim 1, wherein the DNA-binding peptide is selected from the group consisting of a zinc finger DNA-binding domain; a consensus binding sequence from a AVRBS3-inducible gene or synthetic binding sequence engineered therefrom; TAL; LexA; a Tet repressor; LacR; and a steroid hormone receptor.

3. The synthetic transcriptional activator fusion protein of claim 2, wherein the DNA-binding peptide is a zinc finger DNA-binding domain.

4. The synthetic transcriptional activator fusion protein of claim 1, wherein the transactivation domain comprises an amino acid sequence that is at least 80% identical to SEQ ID NO:117 or SEQ ID NO:118.

5. The synthetic transcriptional activator fusion protein of claim 1, wherein the transactivation domain comprises an amino acid sequence that is at least 95% identical to SEQ ID NO:117 or SEQ ID NO:118.

6. The synthetic transcriptional activator fusion protein of claim 1, wherein the transactivation domain comprises SEQ ID NO:117 or SEQ ID NO:118.

7. A nucleic acid molecule comprising a polynucleotide encoding the synthetic transcriptional activator fusion protein of claim 1, the polynucleotide comprising:
   a first nucleotide sequence encoding the DNA-binding peptide; and,
   a second nucleotide sequence encoding the heterologous transactivation domain, wherein the first and second nucleotide sequences are expressed from the nucleic acid molecule in frame and in a single transcript.

8. The nucleic acid molecule of claim 7, wherein the first and second nucleotide sequences are separated by a third nucleotide sequence in the polynucleotide.

9. The nucleic acid molecule of claim 7, wherein the polynucleotide is operably linked to a gene regulatory element.

10. A vector comprising the nucleic acid molecule of claim 7.

11. The nucleic acid molecule of claim 9, wherein the gene regulatory element is a promoter that is functional in a plant cell.

12. A host cell comprising the nucleic acid molecule of claim 7.

13. The host cell of claim 12, wherein the host cell is a plant cell or a yeast cell.

14. A plant cell comprising the nucleic acid molecule of claim 11.

15. The plant cell of claim 14, wherein the polynucleotide and gene regulatory element are integrated into the genome of the cell.

16. A transgenic plant material comprising the nucleic acid molecule of claim 7.

17. The transgenic plant material of claim 16, wherein the plant material is a plant cell, plant cell culture, plant tissue, plant tissue culture, plant part, plant commodity product, or whole plant.

18. The transgenic plant material of claim 17, wherein the plant material is a plant cell, plant cell culture, plant tissue, plant tissue culture, plant part, or whole plant.

19. A method for increasing the expression of a polynucleotide of interest in a host cell, the method comprising:
   introducing the nucleic acid molecule of claim 7 into a host cell comprising the polynucleotide of interest, wherein the polynucleotide of interest is operably linked to a second polynucleotide that binds specifically to the DNA-binding peptide, thereby increasing the expression of the polynucleotide of interest.

20. The method according to claim 19, wherein the host cell is a plant cell.

21. The method according to claim 20, wherein introducing the nucleic acid molecule into the host cell comprises crossing a plant comprising the polynucleotide encoding the synthetic transcriptional activator fusion protein with a plant comprising the host cell.

22. The method according to claim 20, wherein the introducing into the host cell a nucleic acid molecule comprises transforming said host cell with the nucleic acid molecule encoding the synthetic transcriptional activator protein.

23. The nucleic acid molecule of claim 7, further comprising a promoter and a 3' UTR.

* * * * *